(12) United States Patent
Shalon et al.

(10) Patent No.: US 8,540,780 B2
(45) Date of Patent: *Sep. 24, 2013

(54) DEVICES AND METHODS FOR ALTERING EATING BEHAVIOR

(75) Inventors: Tidhar Shalon, Palo Alto, CA (US); Guy Kotlizky, Kfar-Shemaryahu (IL)

(73) Assignee: SVIP 2 LLC., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/411,696

(22) Filed: Mar. 5, 2012

(65) Prior Publication Data

US 2012/0165855 A1 Jun. 28, 2012

Related U.S. Application Data

(63) Continuation of application No. 12/310,359, filed as application No. PCT/IL2007/001047 on Aug. 22, 2007, now Pat. No. 8,142,513.

(60) Provisional application No. 60/924,867, filed on Jun. 4, 2007, provisional application No. 60/860,806, filed on Nov. 24, 2006, provisional application No. 60/839,413, filed on Aug. 23, 2006.

(51) Int. Cl.
*A61F 2/04* (2013.01)
*A61F 2/00* (2006.01)

(52) U.S. Cl.
USPC .................................. 623/23.65; 600/37

(58) Field of Classification Search
USPC ............... 623/23.65–23.7; 128/898; 607/40; 606/108; 600/37
See application file for complete search history.

(56) References Cited

U.S. PATENT DOCUMENTS

| | | | |
|---|---|---|---|
| 4,878,905 A | 11/1989 | Blass | |
| 5,156,641 A | 10/1992 | White | |
| 5,185,005 A | 2/1993 | Ballantyne | |
| 5,234,454 A | 8/1993 | Bangs | |
| 6,231,589 B1 | 5/2001 | Wessman et al. | |
| 6,254,570 B1 | 7/2001 | Rutner et al. | |
| 6,264,700 B1 | 7/2001 | Kilcoyne et al. | |
| 6,746,460 B2 | 6/2004 | Gannoe et al. | |
| 6,754,536 B2 | 6/2004 | Swoyer et al. | |
| 6,971,395 B2 | 12/2005 | Edwards et al. | |
| 7,316,716 B2 | 1/2008 | Egan | |
| 7,430,450 B2 * | 9/2008 | Imran | 607/133 |
| 8,142,513 B2 * | 3/2012 | Shalon et al. | 623/23.65 |
| 2002/0103424 A1 | 8/2002 | Swoyer et al. | |

(Continued)

FOREIGN PATENT DOCUMENTS

| | | |
|---|---|---|
| WO | WO 2005/009288 | 2/2005 |
| WO | WO 2008/003097 | 1/2008 |

(Continued)

OTHER PUBLICATIONS

English Summary of Notice of Rejection Dated May 22, 2012 From the Japanese Patent Office Re. Application No. 2009-525171.

(Continued)

*Primary Examiner* — Suzette J Gherbi

(57) ABSTRACT

A device for modifying an eating behavior of a subject is provided. The device includes a device body which is attachable to GI tract tissue of a subject and functions in altering an eating behavior thereof.

12 Claims, 37 Drawing Sheets
(13 of 37 Drawing Sheet(s) Filed in Color)

(56) References Cited

U.S. PATENT DOCUMENTS

| | | | |
|---|---|---|---|
| 2003/0018367 A1 | 1/2003 | DiLorenzo | |
| 2003/0208183 A1 | 11/2003 | Whalen et al. | |
| 2004/0030347 A1 | 2/2004 | Gannoe et al. | |
| 2004/0185083 A1 | 9/2004 | Dionne et al. | |
| 2005/0177181 A1 | 8/2005 | Kagan et al. | |
| 2005/0283246 A1 | 12/2005 | Cauthen, III et al. | |
| 2006/0020278 A1 | 1/2006 | Burnett et al. | |
| 2006/0079944 A1* | 4/2006 | Imran | 607/40 |
| 2006/0282127 A1 | 12/2006 | Zealear | |
| 2007/0021736 A1 | 1/2007 | Johnson | |
| 2007/0080188 A1 | 4/2007 | Spence et al. | |
| 2007/0162085 A1 | 7/2007 | DiLorenzo | |
| 2007/0246052 A1 | 10/2007 | Hegde et al. | |
| 2007/0250020 A1 | 10/2007 | Kim et al. | |
| 2008/0004598 A1 | 1/2008 | Gilbert | |
| 2008/0091247 A1 | 4/2008 | Muller et al. | |
| 2008/0221599 A1 | 9/2008 | Starksen | |
| 2009/0187230 A1 | 7/2009 | DiLorenzo | |
| 2009/0247992 A1 | 10/2009 | Shalon et al. | |
| 2010/0305656 A1 | 12/2010 | Imran et al. | |

FOREIGN PATENT DOCUMENTS

| | | |
|---|---|---|
| WO | WO 2008/023374 | 2/2008 |
| WO | WO 2008/132745 | 11/2008 |
| WO | WO 2008/149347 | 12/2008 |
| WO | WO 2009/072115 | 6/2009 |
| WO | WO 2009/147670 | 12/2009 |

OTHER PUBLICATIONS

Office Action Dated Mar. 25, 2012 From the Israel Patent Office Re. Application No. 197198 and Its Translation Into English.
Examiner's Report Dated Mar. 21, 2012 From the Australian Government, IP Australia Re. Application No. 2007287201.
Notice of Allowance Dated Aug. 3, 2012 From the US Patent and Trademark Office Re. U.S. Appl. No. 12/451,850.
Communication Pursuant to Article 70(2) and 70a(2) EPC Dated Nov. 17, 2011 From the European Patent Office Re. Application No. 0978014.6.
International Preliminary Report on Patentability Dated Apr. 9, 2009 From the International Bureau of WIPO Re.: Application No. PCT/IL2007/001047.
International Preliminary Report on Patentability Dated Dec. 16, 2010 From the International Bureau of WIPO Re. Application No. PCT/IL2009/000551.
International Preliminary Report on Patentability Dated Jan. 28, 2010 From the International Bureau of WIPO Re.: Application No. PCT/IL2008/000749.
International Search Report and the Written Opinion Dated Oct. 13, 2009 From the International Searching Authority Re.: Application No. PCT/IL09/00551.
International Search Report Dated Jul. 3, 2008 From the International Searching Authority Re.: Application No. PCT/IL07/01047.
International Search Report. Dated Nov. 13, 2008 From the International Searching Authority Re.: Application No. PCT/IL08/00749.
Notice of Allowance Dated Nov. 18, 2011 From the US Patent and Trademark Office Re. U.S. Appl. No. 12/310,359.
Office Action Dated Jan. 12, 2011 From the Israel Patent Office Re. Application No. 197198 and Its Translation Into English.
Official Action Dated Apr. 18, 2011 From the US Patent and Trademark Office Re. U.S. Appl. No. 12/310,359.
Response Dated Jun. 21, 2011 to Official Action of Apr. 18, 2011 From the US Patent and Trademark Office Re. U.S. Appl. No. 12/310,359.
Response Dated Mar. 24, 2011 to Office Action Dated Jan. 12, 2011 From the Israel Patent Office Re. Application No. 197198.
Restriction Official Action Dated Feb. 8, 2012 From the US Patent and Trademark Office Re. U.S. Appl. No. 12/451,850.
Supplementary European Search Report and the European Search Opinion Dated Oct. 31, 2011 From the European Patent Office Re. Application No. 09758014.6.
Written Opinion Dated Jul. 3, 2008 From the International Searching Authority Re.: Application No. PCT/IL07/01047.
Written Opinion Dated Nov. 13, 2008 From the International Searching Authority Re.: Application No. PCT/IL08/00749.
Official Action Dated Mar. 14, 2012 From the US Patent and Trademark Office Re. U.S. Appl. No. 12/451,850.
Requisition by the Examiner Dated May 1, 2013 From the Canadian Intellectual Property Office Re. Application No. 2,661,191.

* cited by examiner

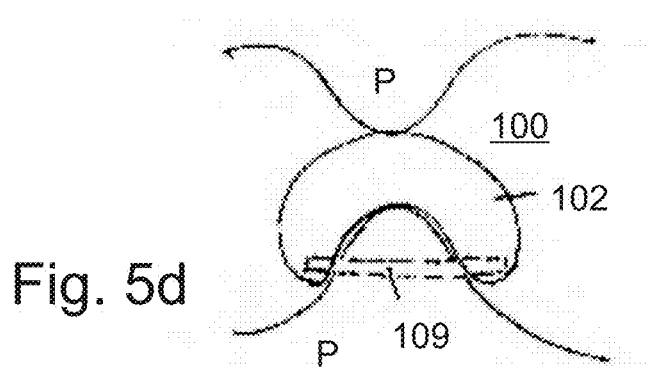
Fig. 5d
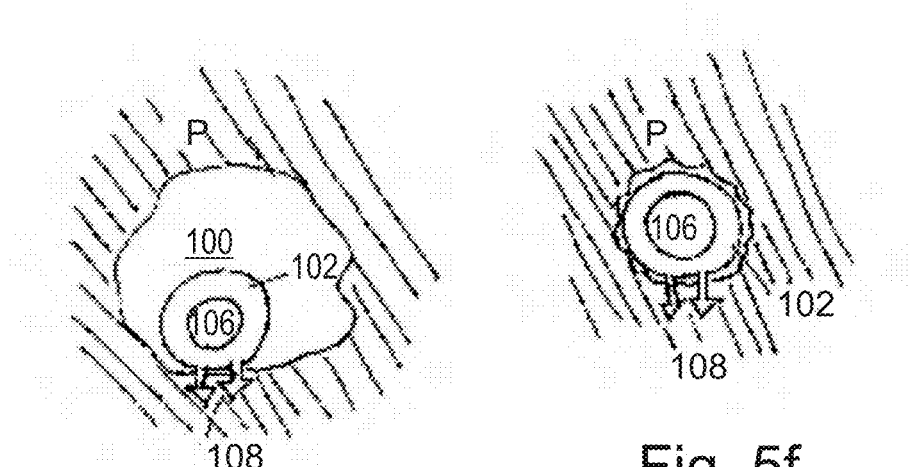
Fig. 5e
Fig. 5f
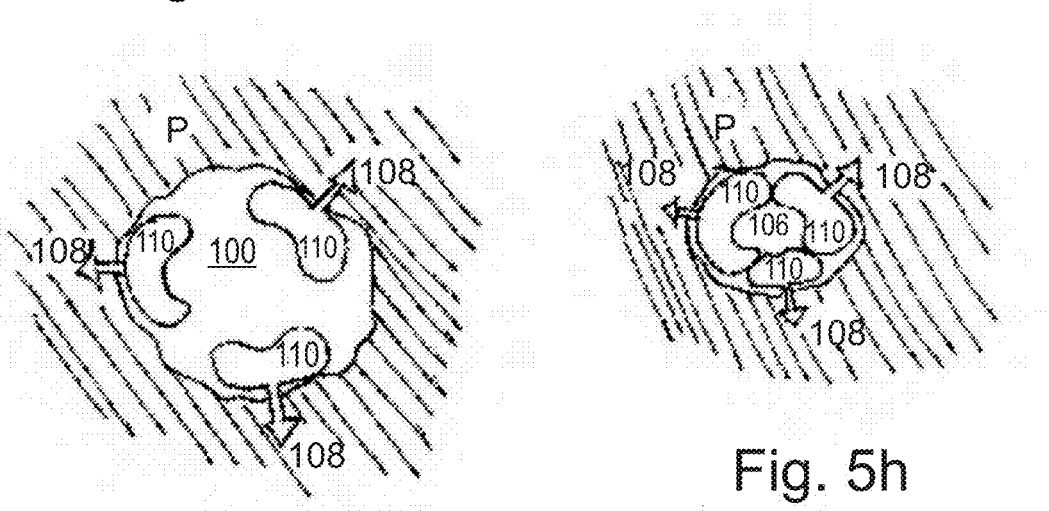
Fig. 5g
Fig. 5h

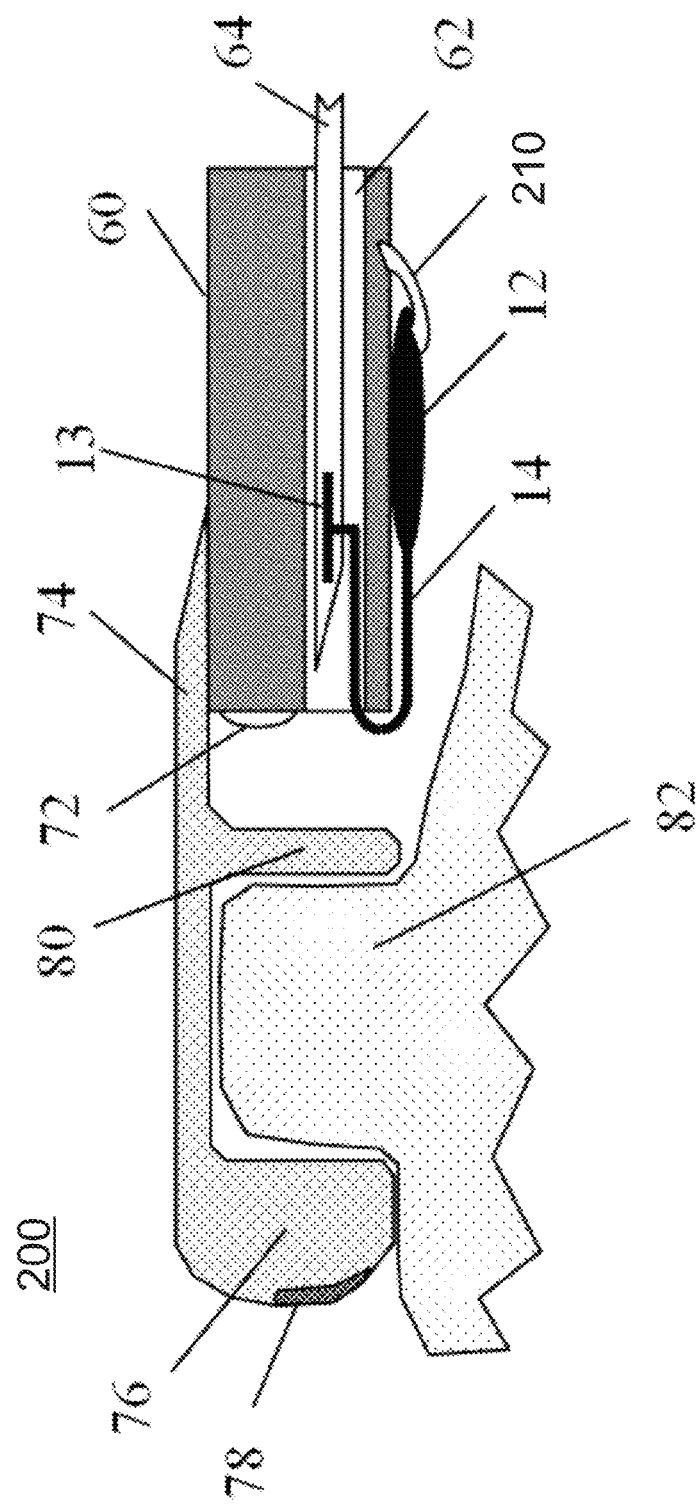

DEVICES AND METHODS FOR ALTERING EATING BEHAVIOR

RELATED APPLICATIONS

This Application is a Continuation of U.S. patent application Ser. No. 12/310,359 filed on Feb. 23, 2009, which is a National Phase of PCT Patent Application No. PCT/IL2007/001047 having International filing date of Aug. 22, 2007, which claims the benefit of priority of U.S. Provisional Patent Application Nos. 60/924,867 filed on Jun. 4, 2007, 60/860,806 filed on Nov. 24, 2006 and 60/839,413 filed on Aug. 23, 2006. The contents of the above Applications are all incorporated herein by reference.

FIELD AND BACKGROUND OF THE INVENTION

The present invention relates to devices and methods which can be used to alter an eating behavior of a subject.

During the past 20 years, obesity among adults has risen significantly in the United States. The latest data from the National Center for Health Statistics show that 30 percent of U.S. adults 20 years of age and older—over 60 million people—are obese. Obesity requires long-term management; the goal of treatment is weight loss to improve, prevent occurrence of, or eliminate related health problems.

Numerous approaches for the treatment of obesity are known in the art, including drug treatment, surgical procedures and implantable devices.

Drugs for treatment of obesity fall into three general categories, appetite altering drugs such as dexfenfluramine or sibutramine which suppresses appetite by altering neurotransmitter release or uptake in the brain; metabolism-changing drugs such as Orlistat which prevents the action of lipases (enzymes that break down fat) produced in the pancreas; and drugs that increase energy output ('thermogenic' drugs) such as ephedrine and caffeine which stimulate weight loss by reducing appetite and perhaps by stimulating the body to produce more heat.

Although these drugs offer useful therapeutic effects, there remains a need for more effective obesity treatment drugs. Such a need will fuel tremendous commercial opportunity and so in the future drugs which target gastrointestinal or brain receptors for satiety, or block/mimic the action of satiety altering hormones and substances (such as ghrelin, CCK, PYY, obestatin, leptin, glucagons, neuropeptide Y and the like) might make their way to the market.

Two forms of surgery have been recommended by government consensus panels that can be performed to treat severe obesity. Both are for people with severe cases of obesity, over 100 lbs above ideal body weight (e.g., BMI>40 kg/m$^2$), who have not had effective weight loss with diet, exercise or drugs.

Gastroplasty involves surgically reducing the size of the stomach, thus limiting food intake. Vertical band gastroplasty (VBG) is successful in more than 85% of patients, and weight loss is maintained over prolonged time periods (Barclay Obes Surg. 2004 November-December; 14(10):1415-8). Gastric bypass surgery (e.g. Roux en Y) creates a small stomach pouch and connects this pouch to the second portion of the intestines. Gastric bypass surgery can initially result in substantial weight loss, and approximately 80 percent of patients remain at least 10 percent below their preoperative body weight for 10 years after surgery. The efficacy of the procedure is probably due to the increased sense of fullness with a reduced gastric volume and the symptoms of "dumping" associated with the passage of gastric contents into the intestines, which act as deterrents to eating (Rosenbaum et al. Obesity NEJM Volume 337:396-407 Aug. 7, 1997 Number 6). Although gastric bypass surgery is highly effective, it carries a risk of morbidly and it is more extensive and difficult to perform than gastroplasty.

Numerous devices for altering satiety are also known in the art. Some devices restrict stomach size or food intake via bands [e.g. lap band et al. MJA 2005; 183 (6): 310-314] or space occupying elements [e.g. intra-stomach balloons—Obes Surg. 2005 September; 15(8):1161-4]. Others alter stomach or pyloric muscle activity via neuronal or muscular implanted electrodes (Shikora, Journal of gastrointestinal surgery Volume 8, Issue 4, Pages 408-412; Xu et al. Gastroenterology 2005; 128:43-50).

Although numerous treatment approaches are available at present, the most effective approach with the best long term effects is restricted to the treatment of severely obese people and in addition it requires complicated surgery which can lead to severe complications or death.

There is thus a widely recognized need for, and it would be highly advantageous to have, an eating behavior altering device and method devoid of the above limitations.

SUMMARY OF THE INVENTION

According to one aspect of the present invention there is provided a device for modifying an eating behavior of a subject comprising a device body attachable to tissue of a stomach, the device body being capable of intermittently contacting a wall region of a duodenum and/or the pylorus and/or the antrum when attached to the tissue of the stomach.

According to further features in preferred embodiments of the invention described below, the device is sized and configured so as to not have any substantial effect on flow through the antrum and the duodenum.

According to still further features in the described preferred embodiments the tissue of the stomach is a body of the stomach, the antrum or the pylorus.

According to still further features in the described preferred embodiments the device further comprises a tether attached to the device body, the tether being attachable to the tissue of the stomach.

According to still further features in the described preferred embodiments the tissue of the stomach is a body of the stomach, the antrum or the pylorus.

According to still further features in the described preferred embodiments an end of the tether is designed for anchoring in or through the tissue of the antrum or the pylorus.

According to still further features in the described preferred embodiments the tether is designed for anchoring in or through the tissue of the stomach.

According to still further features in the described preferred embodiments the tether is an elastic tether.

According to still further features in the described preferred embodiments the tether is sized and configured such that the device body is capable of moving between the antrum and the duodenum when the tether is attached to the tissue of the stomach.

According to still further features in the described preferred embodiments the device body is cylindrical, e.g. egg shaped.

According to still further features in the described preferred embodiments the device body includes at least one protrusion and/or concavity.

According to still further features in the described preferred embodiments the device body is less than 4 cm³ in volume.

According to still further features in the described preferred embodiments a surface area of the device body is less than 15 cm².

According to still further features in the described preferred embodiments the tether is attachable through the tissue via a t-bar anchor.

According to still further features in the described preferred embodiments the device further includes a washer element for preventing erosion of the t-bar anchor into the tissue of the stomach.

According to another aspect of the present invention there is provided a device for modifying an eating behavior of a subject comprising: (a) a device body; and (b) a tether having a first end attached to the device body and a second end being anchorable to tissue in a stomach, the tether being sized and configured such that the device body is capable of contacting tissue of a duodenum when the second end of the tether is anchored to tissue of the stomach.

According to still further features in the described preferred embodiments the device body is sized and configured so as to not substantially obstruct food flow through the antrum and the pylorus.

According to still further features in the described preferred embodiments the tether is an inelastic tether.

According to still further features in the described preferred embodiments the tether is an elastic tether.

According to still further features in the described preferred embodiments the tether is sized and configured such that the device body is capable of moving between an antrum and the duodenum when the tether is attached to the tissue of the stomach.

According to still further features in the described preferred embodiments the device body is cylindrical.

According to still further features in the described preferred embodiments the device body includes at least one protrusion and/or concavity.

According to still further features in the described preferred embodiments the device body is less than 4 cm³ in volume.

According to still further features in the described preferred embodiments a surface area of the device body is less than 15 cm².

According to still further features in the described preferred embodiments the second end is anchorable to the tissue of the stomach via in or through tissue anchoring.

According to still further features in the described preferred embodiments the tissue of the stomach is a body of the stomach, an antrum or a pylorus.

According to yet another aspect of the present invention there is provided an implantable device comprising a device body attached to at least one tissue anchor, the tissue anchor comprising a tissue anchoring element attached to a tether having elastic properties.

According to still another aspect of the present invention there is provided a device for modifying an eating behavior of a subject comprising a device body attachable to a tissue of a GI tract, the device body being capable of intermittently contacting a wall region of a duodenum, a pylorus and/or an antrum when attached to the tissue of the GI tract.

According to still further features in the described preferred embodiments the device body is attached to the tissue of the GI tract through a tether.

According to still further features in the described preferred embodiments an end of the tether is anchored in or through the tissue of the GI tract.

According to still another aspect of the present invention there is provided a method of inducing early satiety in a subject comprising attaching a device to a tissue of the antrum or pylorus of a subject in need, the device being configured so as to intermittently contact a wall region of a duodenum and/or the pylorus and/or the antrum.

According to still another aspect of the present invention there is provided a system for modifying an eating behavior of a subject comprising: (a) a delivery apparatus being capable of anchoring a tether in or through GI tract tissue; and (b) a device including a device body attached to the tether, the device being capable of altering the eating behavior of the subject when anchored to the GI tract tissue.

According to still further features in the described preferred embodiments the apparatus includes a vacuum chamber for suctioning a volume of the GI tract tissue.

According to still further features in the described preferred embodiments the apparatus further includes a tissue piercing element capable of piercing in or through the volume of the GI tract tissue.

The present invention successfully addresses the shortcomings of the presently to known configurations by providing devices and methods which can be used to effectively alter an eating behavior of a subject using a safe, minimally invasive procedure.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1:
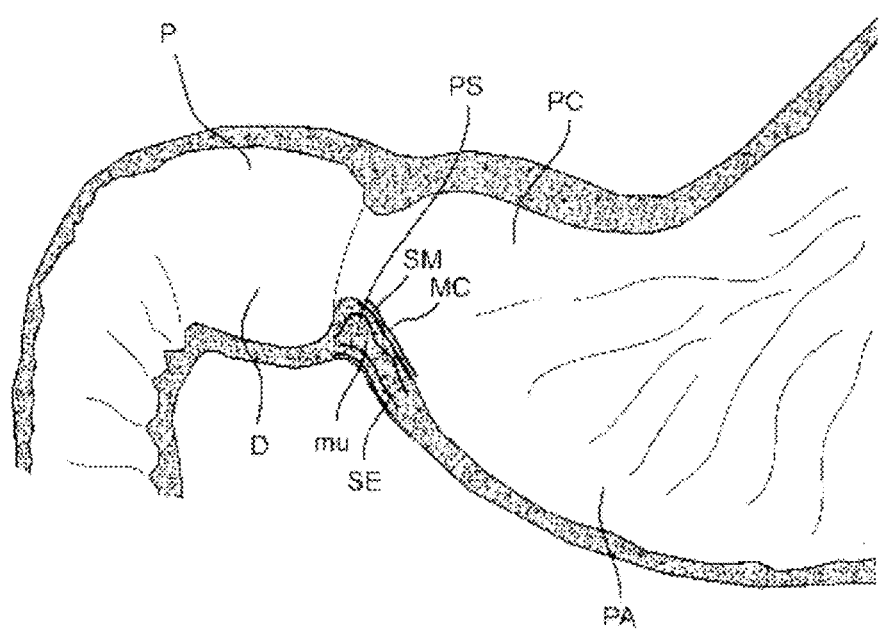

FIG. 1 schematically illustrates the stomach-duodenum junction showing the pyloric antrum (PA), the pyloric canal (PC), the duodenum (D), the pyloric sphincter (PS), the submucosal (SM), mucosal (MC), muscle (mu) and serosa (SE) layers and the Pyloric opening (PO).

Figure 2A:
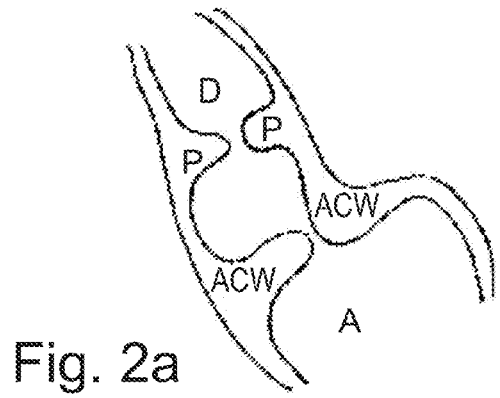
Figure 2B:
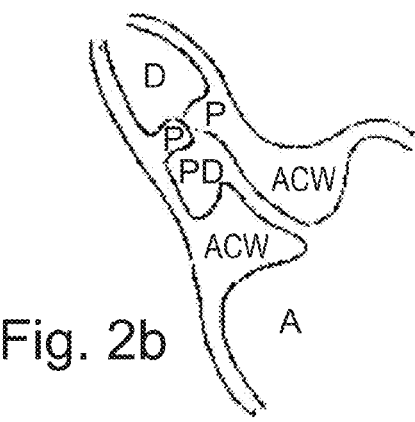
Figure 2C:
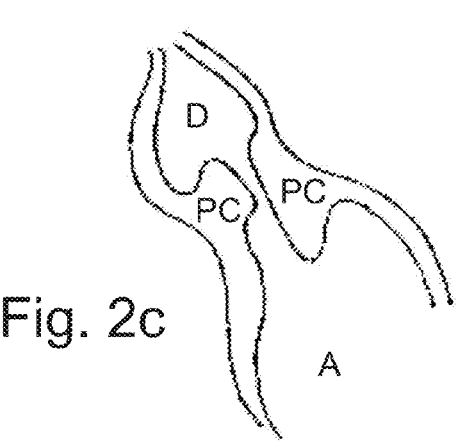

FIGS. 2a-c are prior art diagrams illustrating gastric emptying events as manifested in the antral/pyloric/duodenal regions of the GI tract.

Figure 2D:
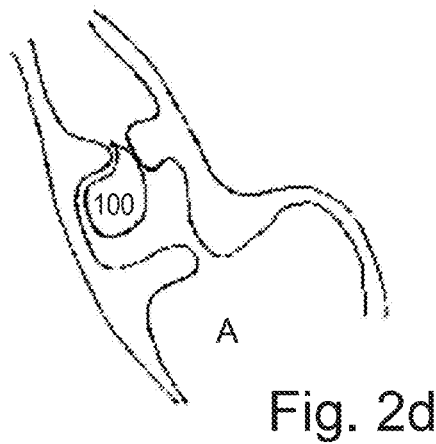
Figure 2E:
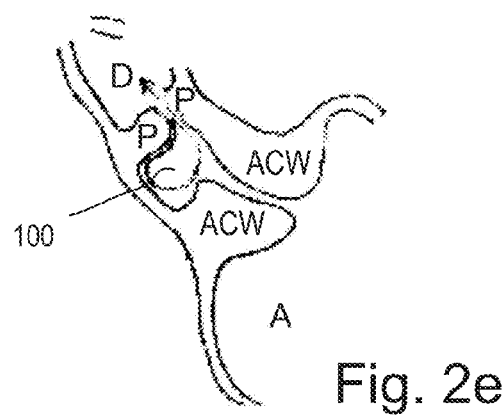
Figure 2F:
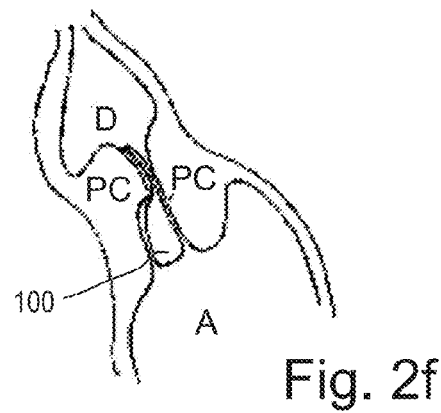

FIGS. 2d-f illustrate the effect of the device of the present invention on the three stages of gastric emptying illustrated in FIGS. 2a-c.

Figure 3A:
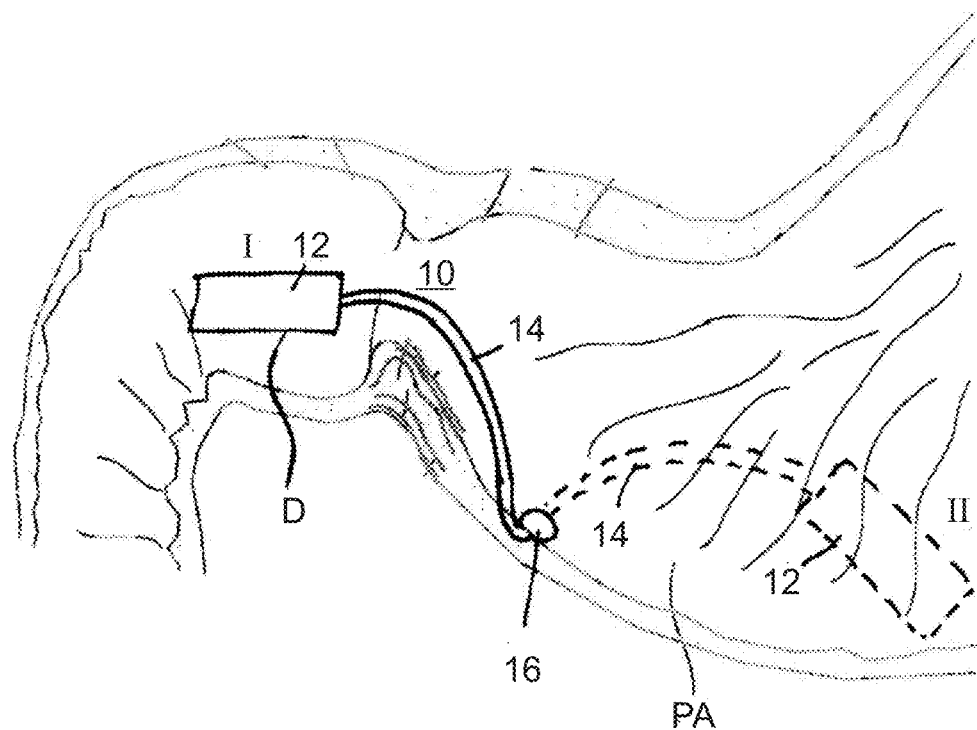
Figure 3B:
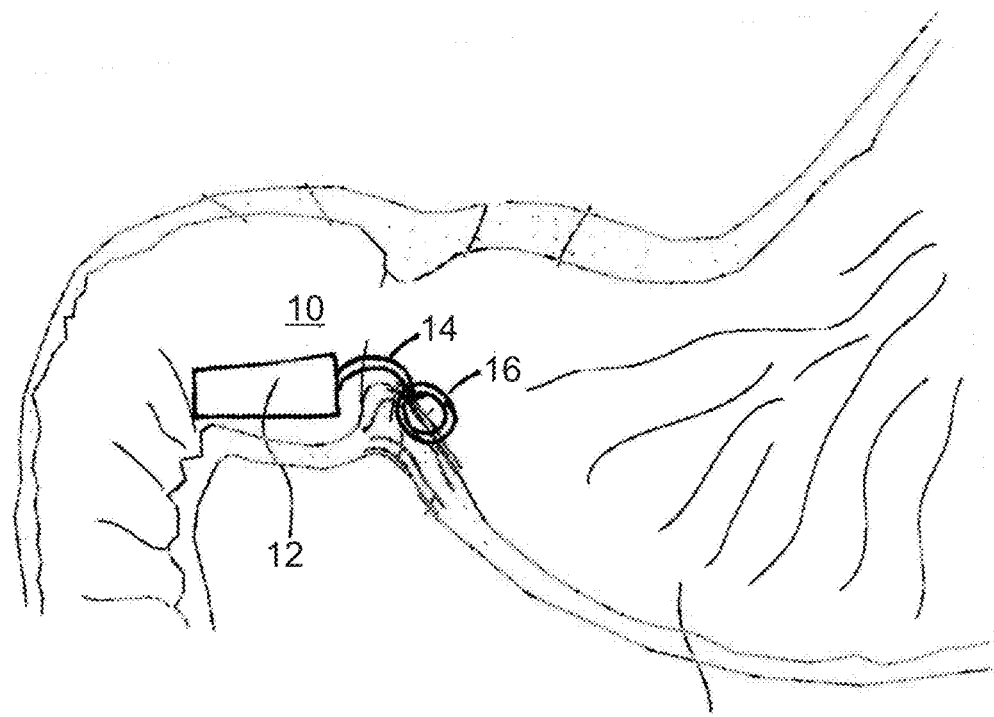
Figure 3C:
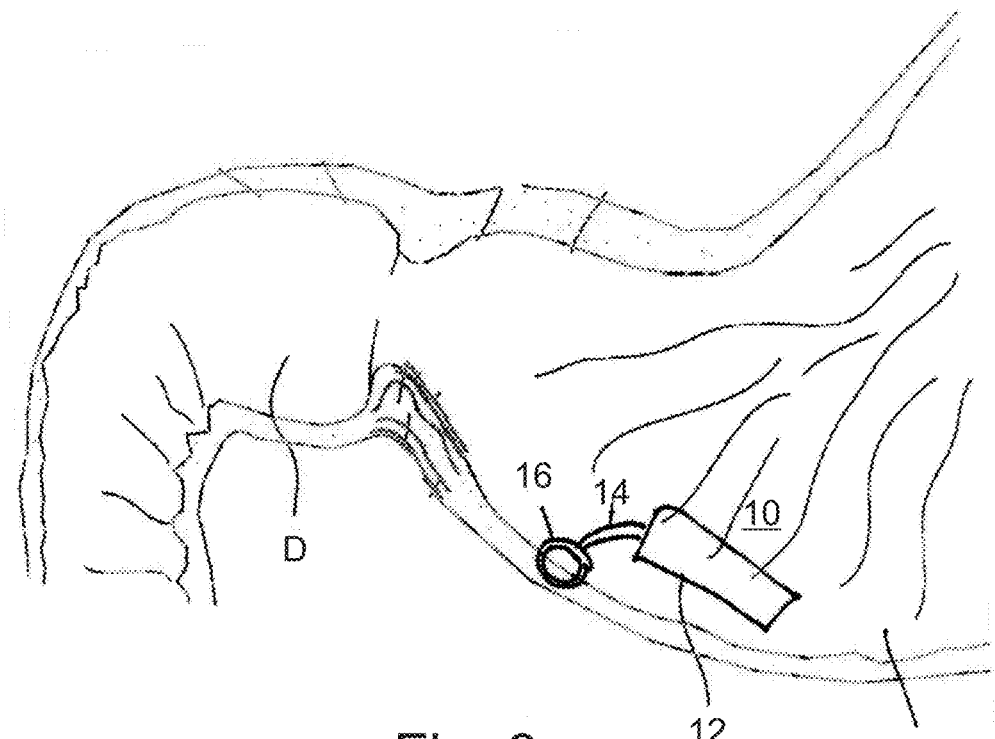

FIGS. 3a-c illustrate embodiments of the device of the present invention.

Figure 3D:
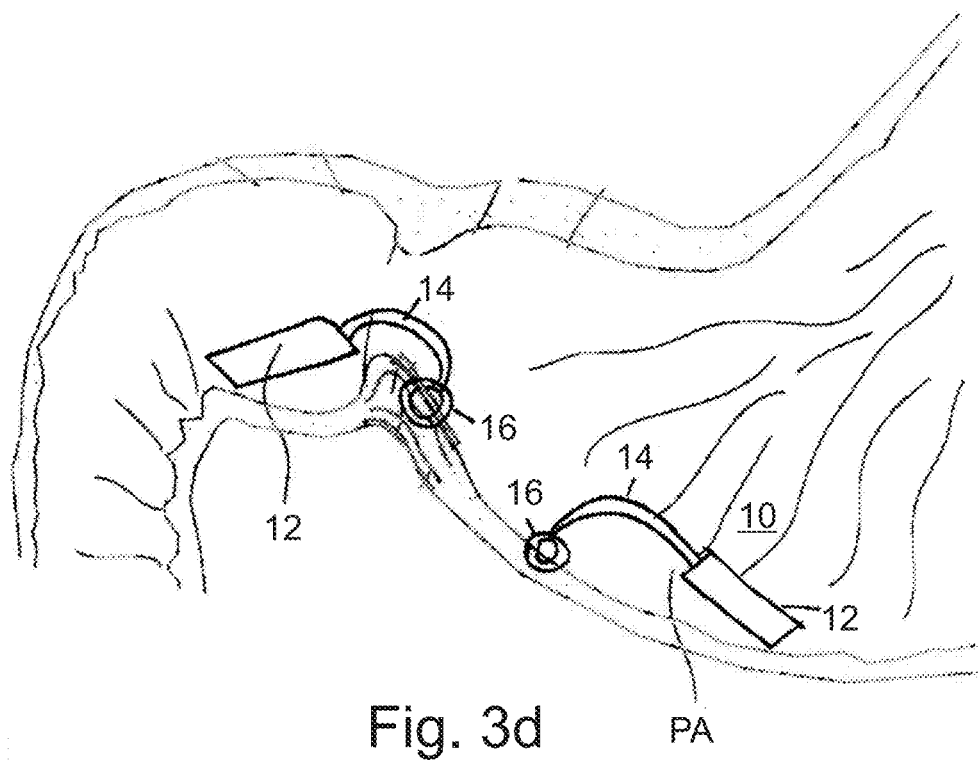

FIG. 3d illustrates an embodiment of the present invention which utilizes two implanted devices, one having a device body residing in the antrum and another in the duodenum.

FIGS. 4a-d illustrate several embodiments of the device body of the device of the present invention.

Figure 5A:
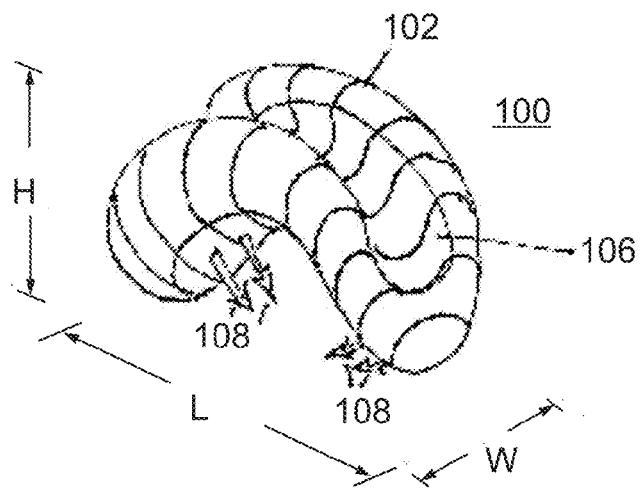
Figure 5B:
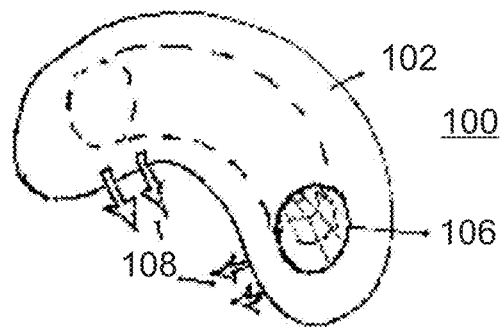
Figure 5C:
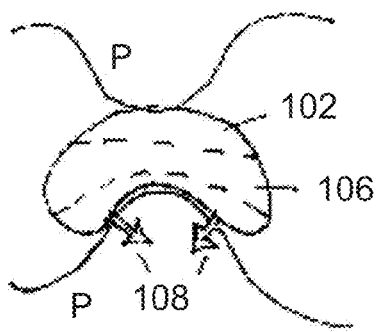
Figure 5I:
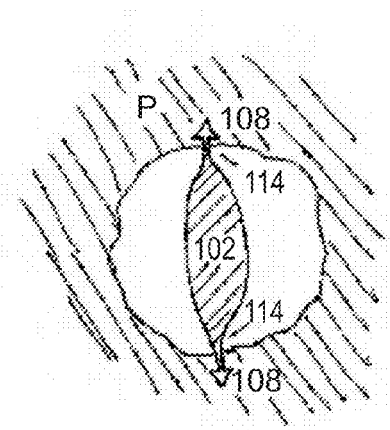
Figure 5J:
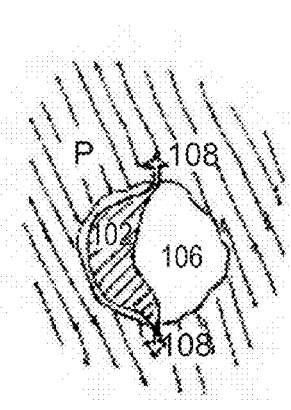
Figure 5K:
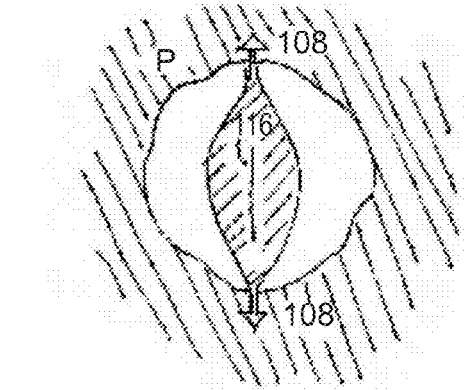
Figure 5L:
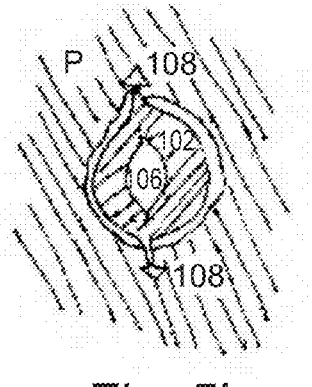
Figure 5M:
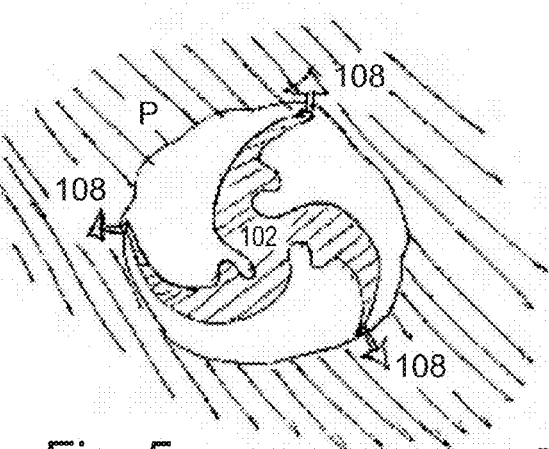
Figure 5N:
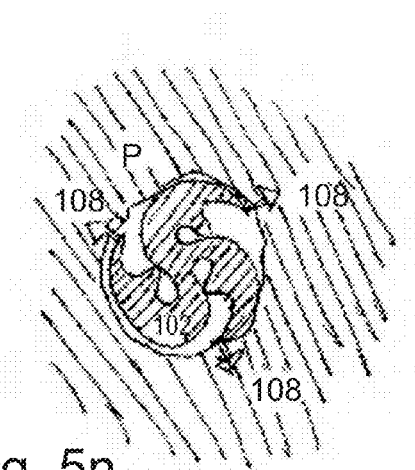

FIGS. 5a-n illustrates additional embodiments of a device constructed in accordance with the teachings of the present invention.

FIGS. 6a-g illustrates additional embodiments of a pyloric device in the duodenal/pyloric/antral regions of the GI tract.

FIGS. 7a-7c and 8a-8c illustrate the positioning and anchoring of one embodiment of the device of the present invention within the pyloric canal and other tissue of the GI system.

Figure 8A:
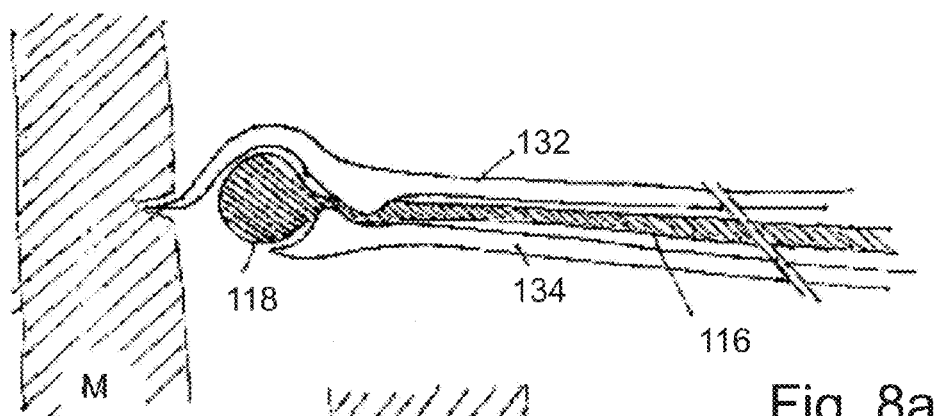
Figure 8B:
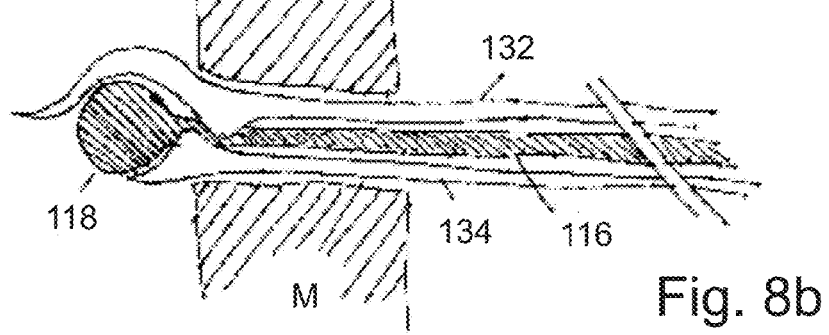
Figure 8C:
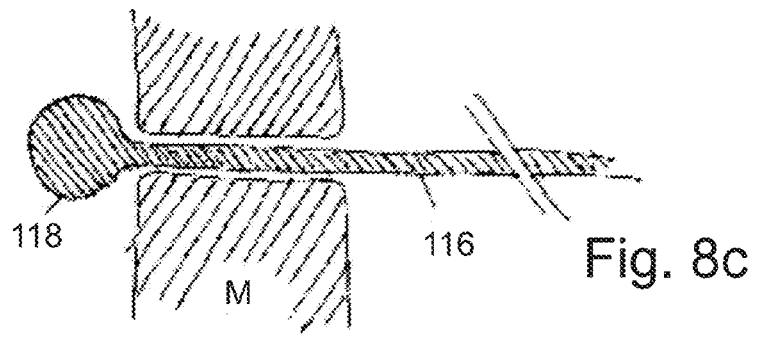
Figure 9:
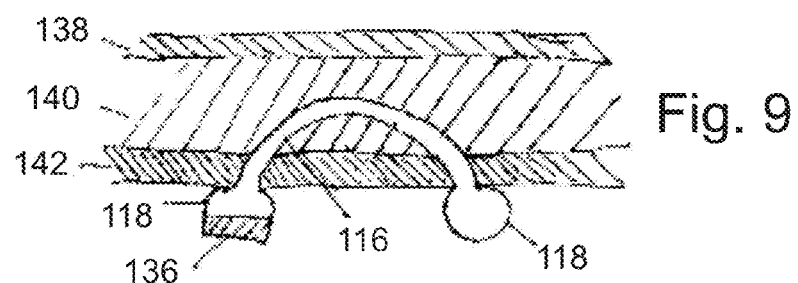

FIG. 9 illustrates the use of the anchoring technique of FIG. 8a-c to anchor a generic sensor or actuator in the stomach wall.

FIGS. 10a-d illustrate several embodiments of the present device Implanted devices were retrieved from pigs and photographed over an illustration of GI anatomy to show relative positioning of the device with respect to the stomach and duodenum.

Figure 11:
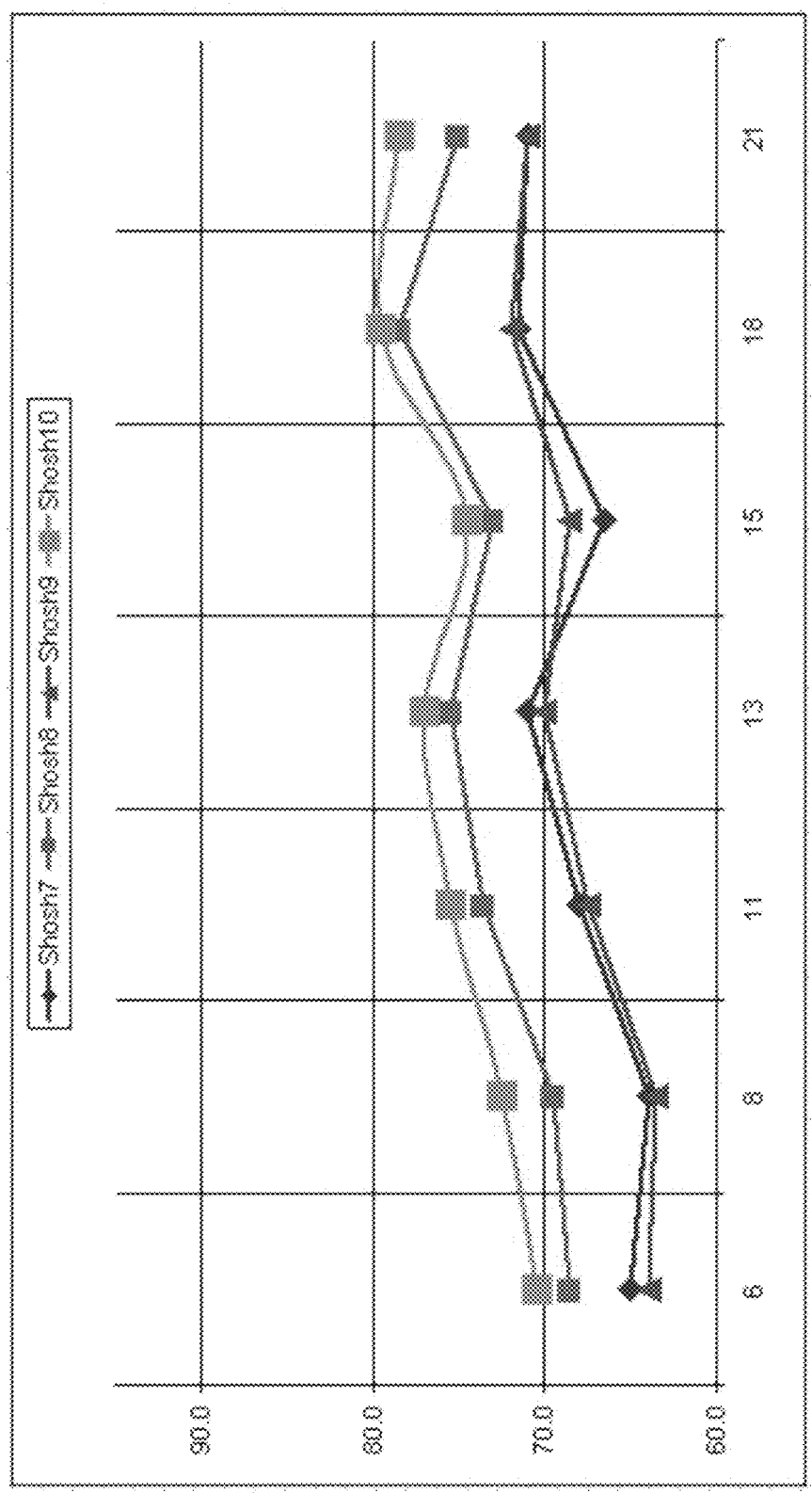
Figure 12:
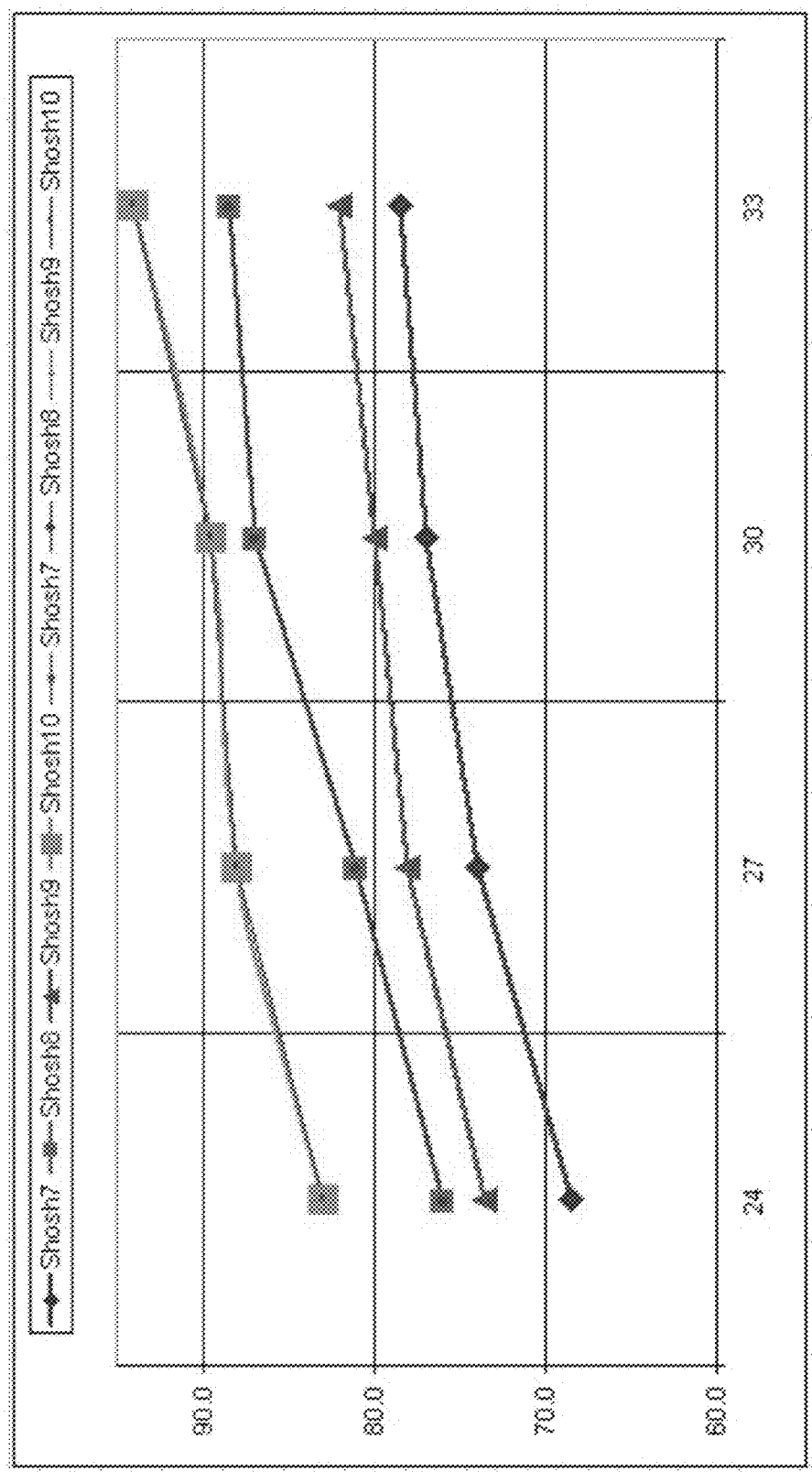

FIGS. 11-12 graphically illustrate the daily weight (in kilos) of the three pigs implanted with the present device as more fully described in the examples section.

Figure 13:
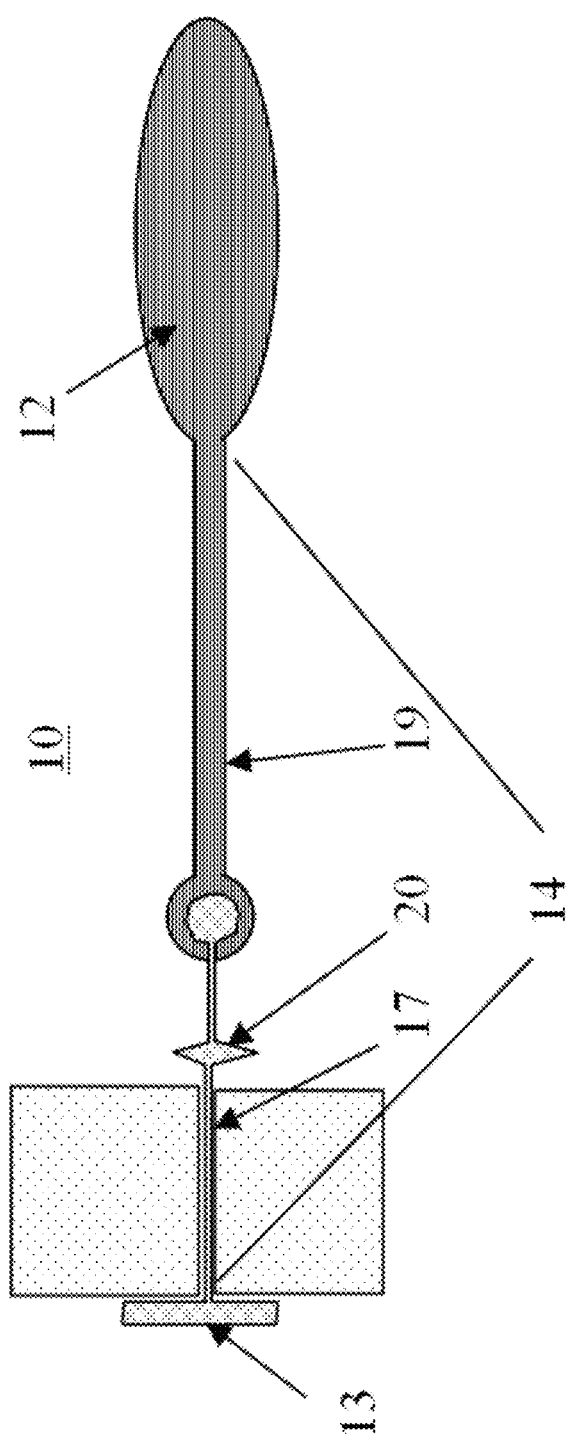

FIG. 13 schematically illustrates one embodiment of the present device as anchored in-tissue and provided with a tether-mounted stopper for preventing unwanted movement of the tether through the tissue.

Figure 14:
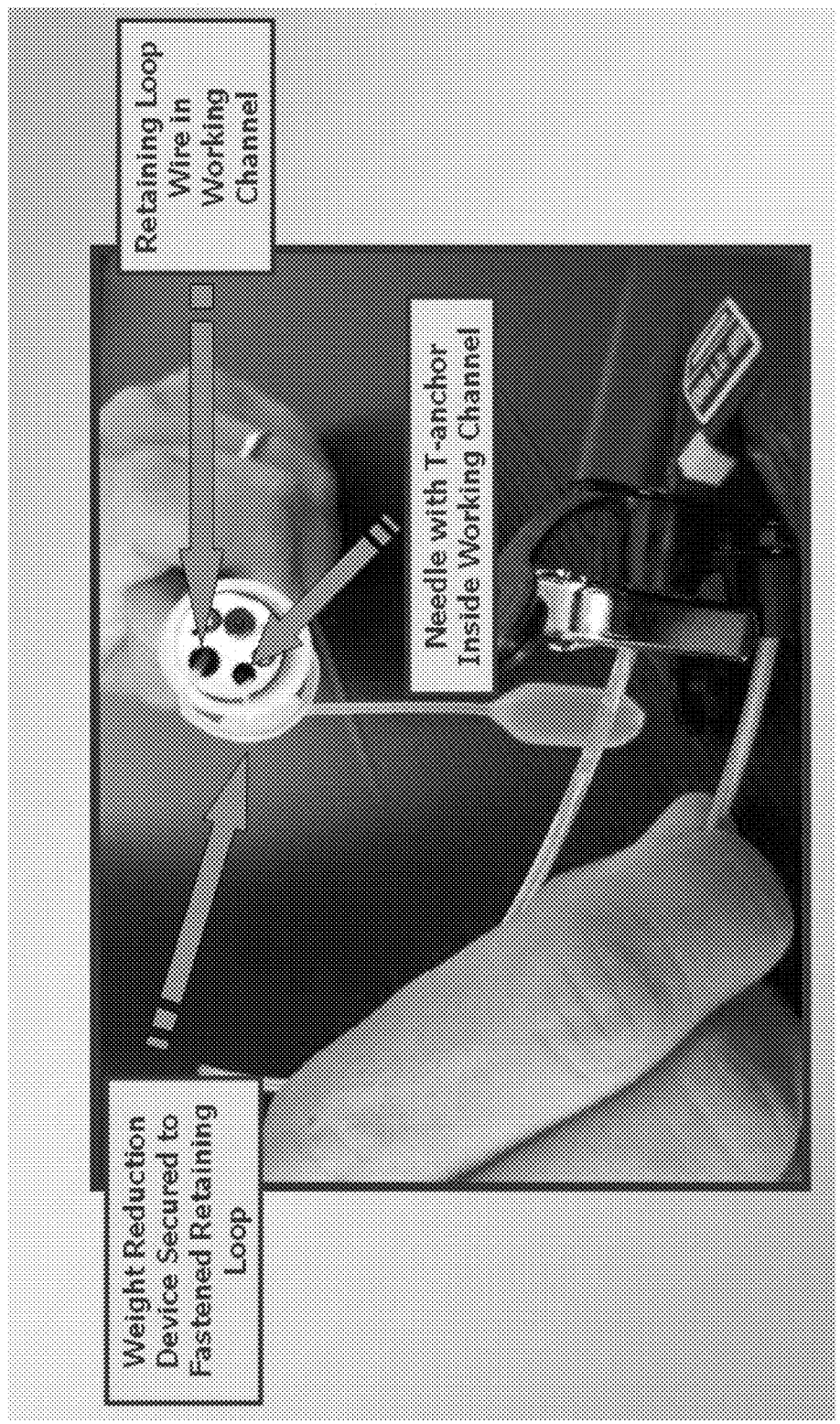
Figure 15:
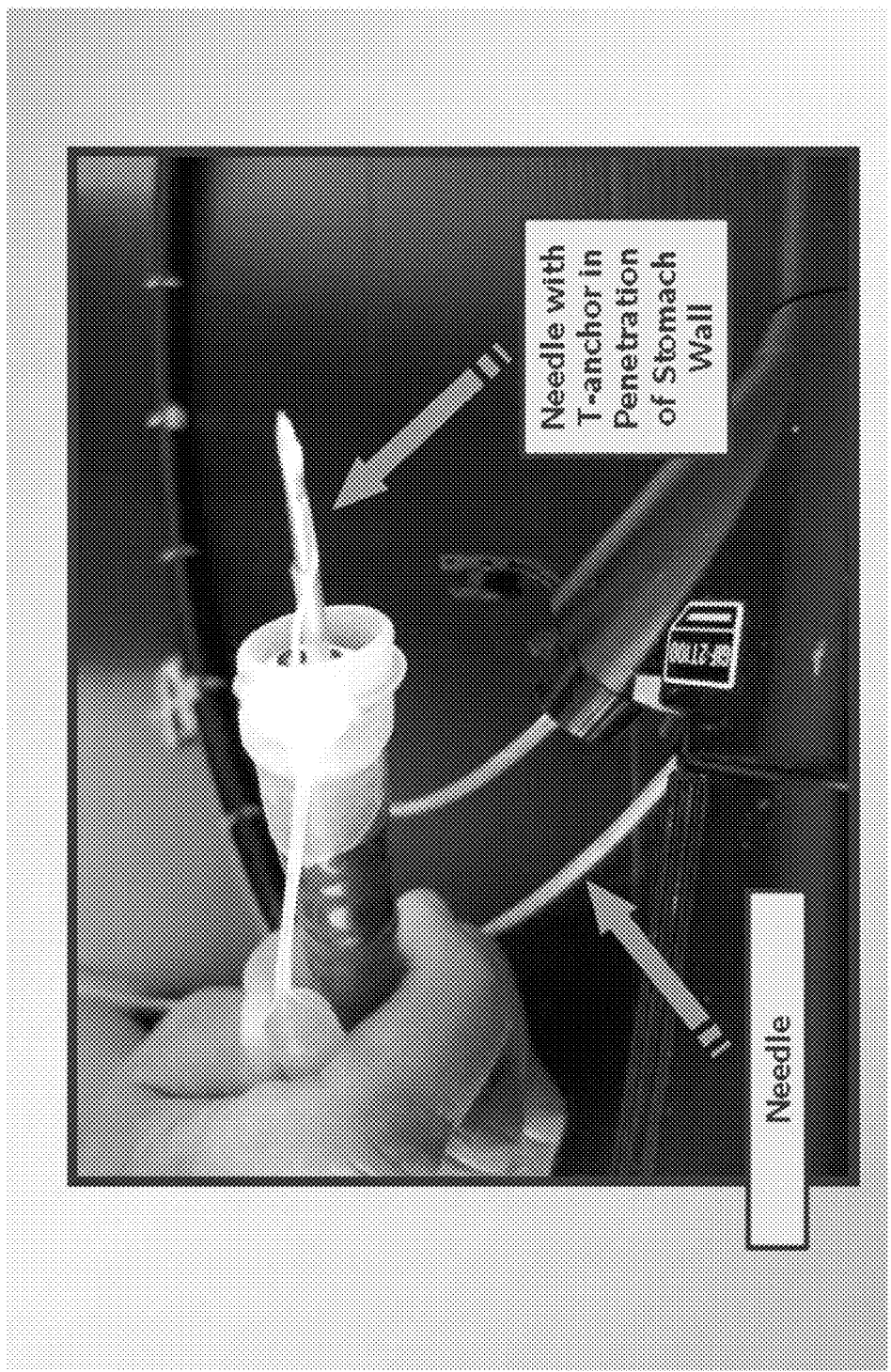
Figure 16:
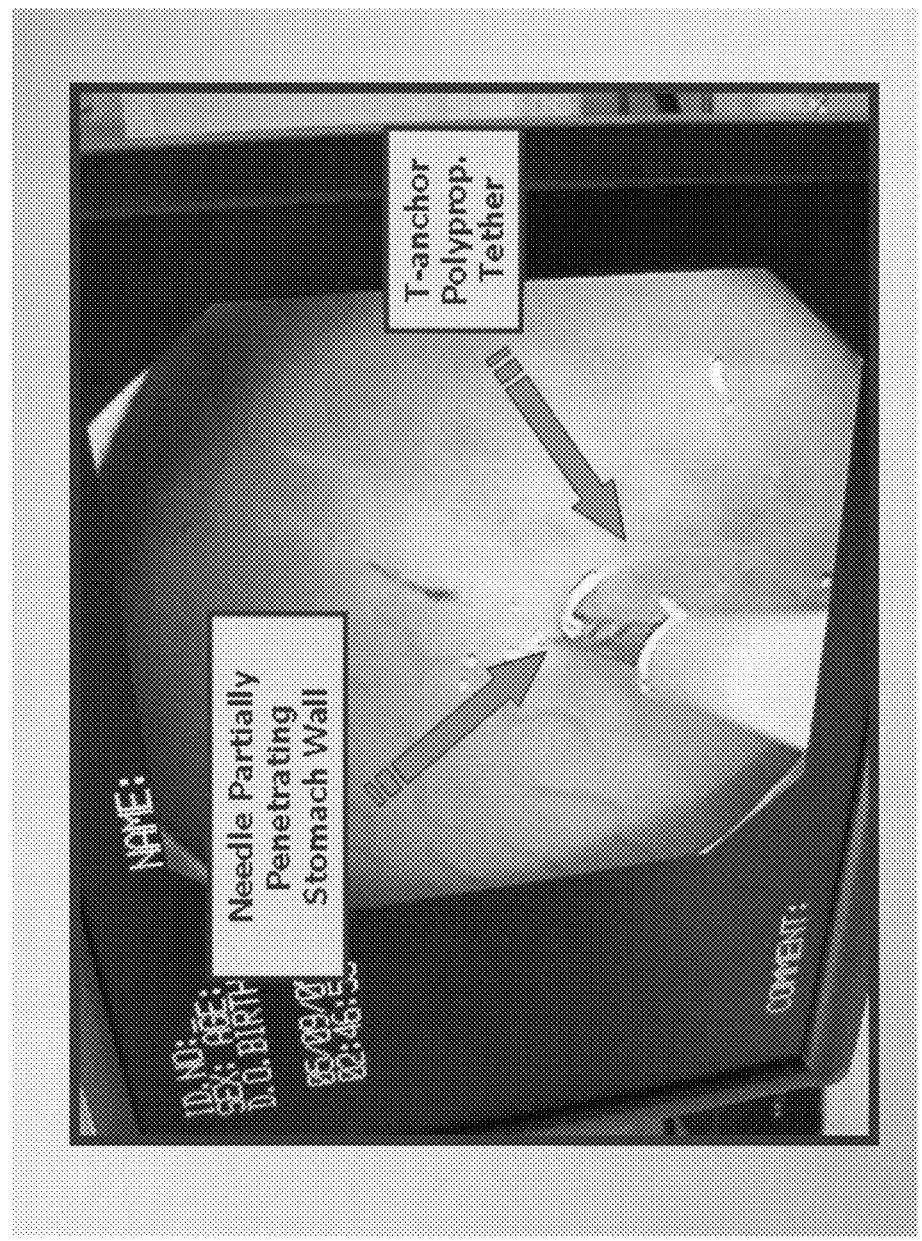
Figure 17:
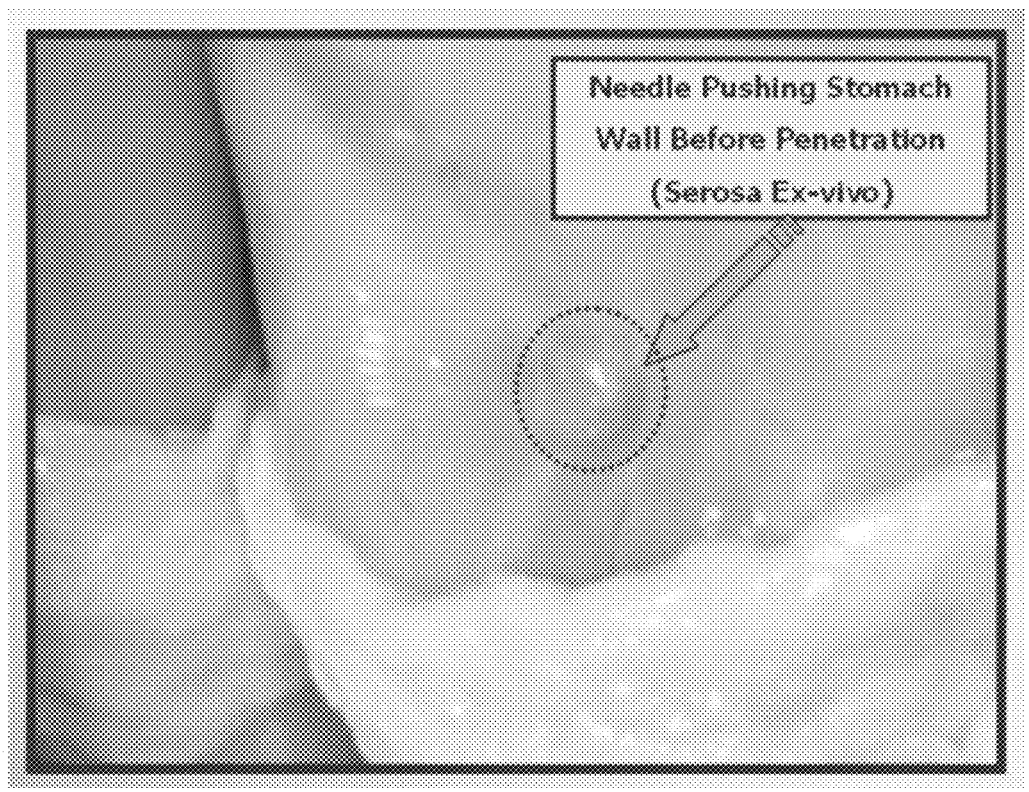

FIGS. 14-15 illustrate a system used for anchoring the satiety-inducing device of the present invention.

FIGS. 16, 17, 18 and 19a-19b illustrate anchoring of the device of the present invention in the stomach of pigs.

Figure 20A:
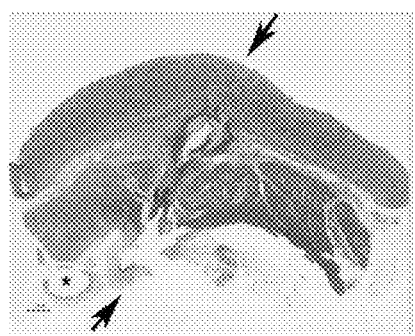
Figure 20B:
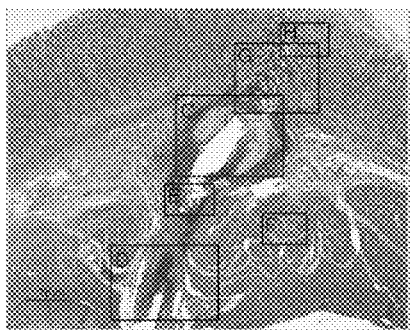
Figure 20C:
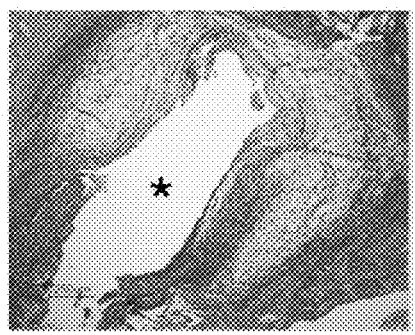
Figure 20D:
Figure 20E:
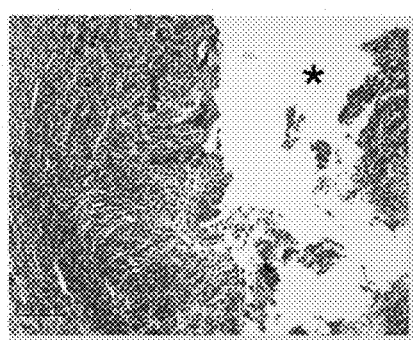
Figure 20F:
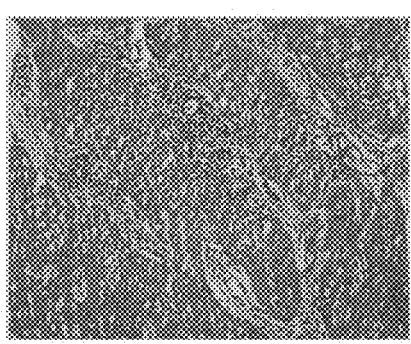
Figure 20G:
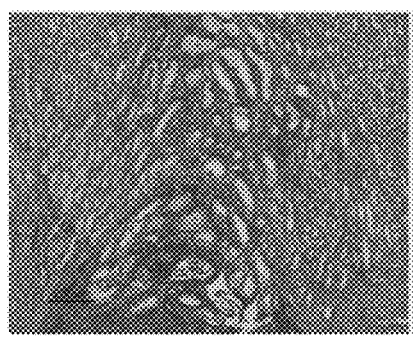
Figure 20H:
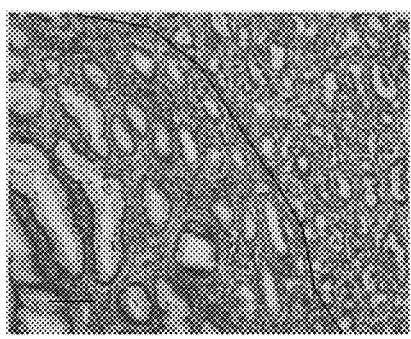

FIGS. 20a-h illustrate histology of the tissue region used for anchoring showing the benign nature of the anchor described in this invention after 6 weeks device implantation in the stomach of a pig. Note the lack of erosion and lack of severe inflammation or tissue remodeling. FIGS. 20a-b, bar=1 mm; FIGS. 20c-h, bar=250 µm; section were stained with Haematoxylin & Eosin (HE). FIG. 20a: Very low power view of the specimen. The mucosa is towards the top. Arrows point to the tract traversing the sample. An asterisk indicates the space where one of the bars of the T-shaped implant was located. FIG. 20b: Low power view of the specimen. The tract is in the center. Squares indicate the regions from which higher power views were obtained. The letter in each square refers to the relevant image. FIG. 20c: Medium power view of the tract within the submucosa. An asterisk indicates the lumen of the tract. This is where the implant was located. The lumen/implant is surrounded by loose fibrous tissue and inflammatory cells. (The latter are difficult to resolve at this magnification). FIG. 20d: Medium power view of the tract within the tunica muscularis. An asterisk indicates the lumen of the tract. In this area a small amount of fibrin adheres to the wall of the tract (small arrows) and the inflammatory infiltration is more intense—seen as the granular blue staining in the center. FIG. 20e: High power view of the wall of the tract (the lumen is indicated with an asterisk). There is lymphohistiocytic infiltration and fibrosis, typical of reaction to a foreign body. FIG. 20f: High power view of the tunica muscularis showing multifocal predominantly perivascular mononuclear infiltration and vacuolation in the smooth muscle cells. FIG. 20g: Medium power view of the mucosa in the immediate vicinity of the tract. There is mild distortion of crypt architecture with localized hyperplasia and mucous metaplasia. FIG. 20h: High power view of part of the field shown in FIG. 20g. Away from the small area with mucosal hyperplasia and mucous metaplasia (the left half of the image), the mucosa is essentially unremarkable and contains the normal complement of parietal cells. A black line indicates the interface between these two regions.

Figure 21B:
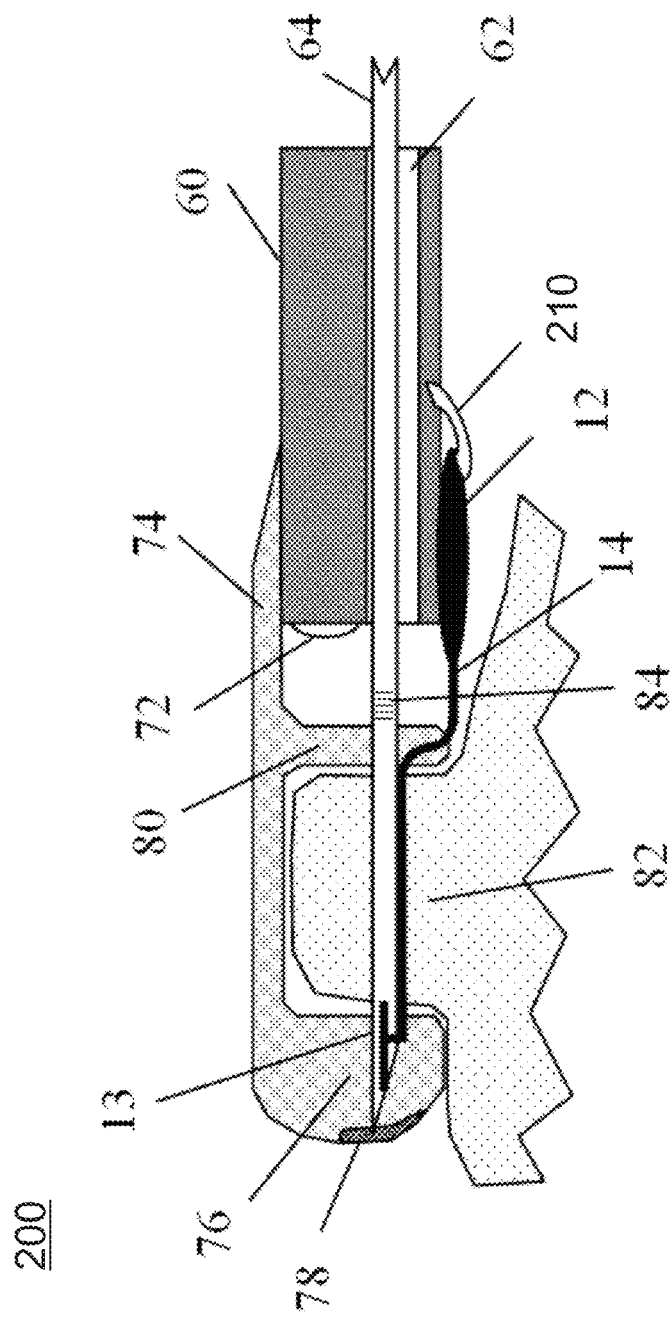
Figure 21C:
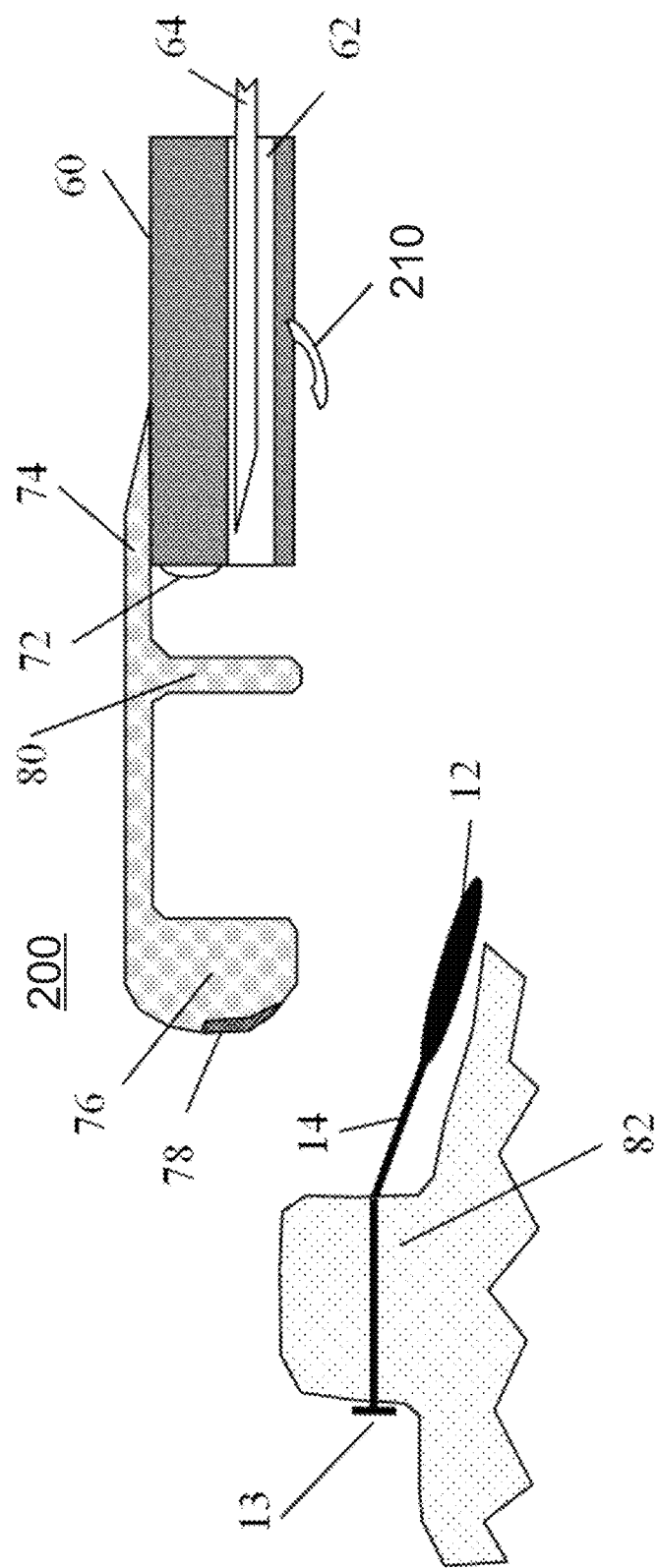

FIGS. 21a-c illustrate an apparatus for delivering and positioning a device constructed in accordance with the teachings of the present invention.

Figure 22A:
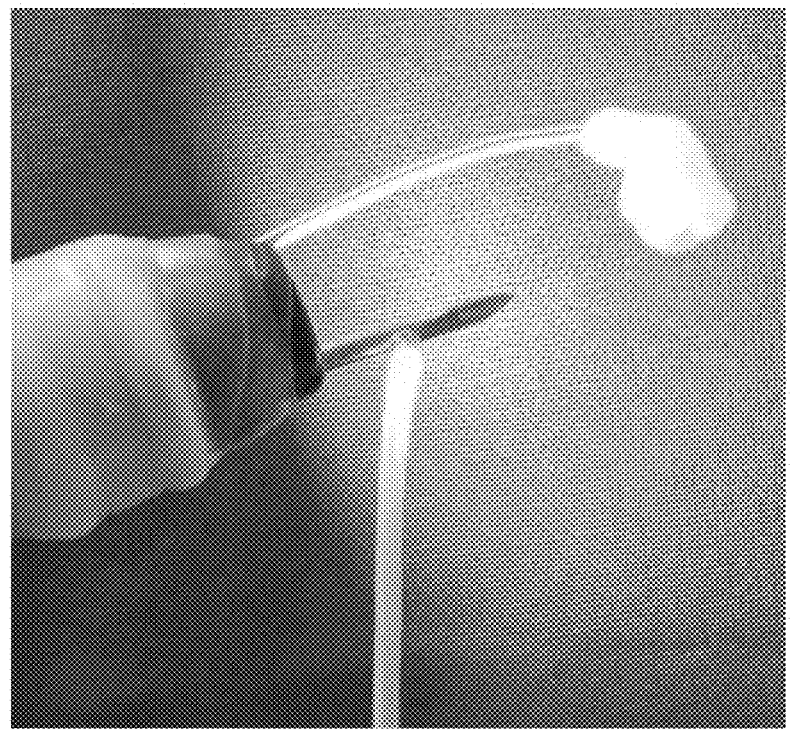
Figure 22B:
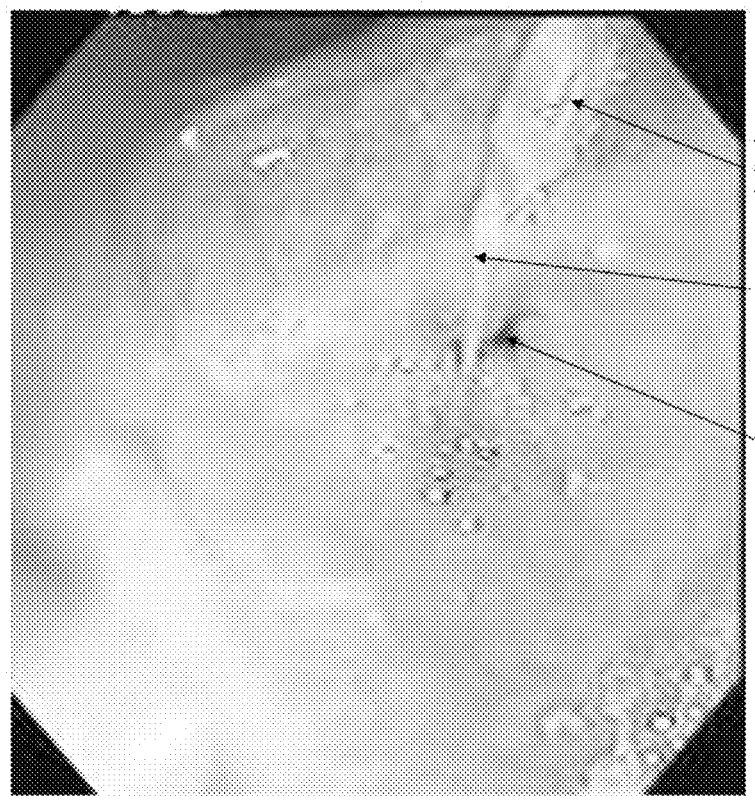

FIGS. 22a-b illustrate the delivery apparatus utilized for anchoring a gastric device in the pyloric sphincter of pigs (FIG. 22a) and the anchored device following the procedure (FIG. 22b).

Figure 23A:
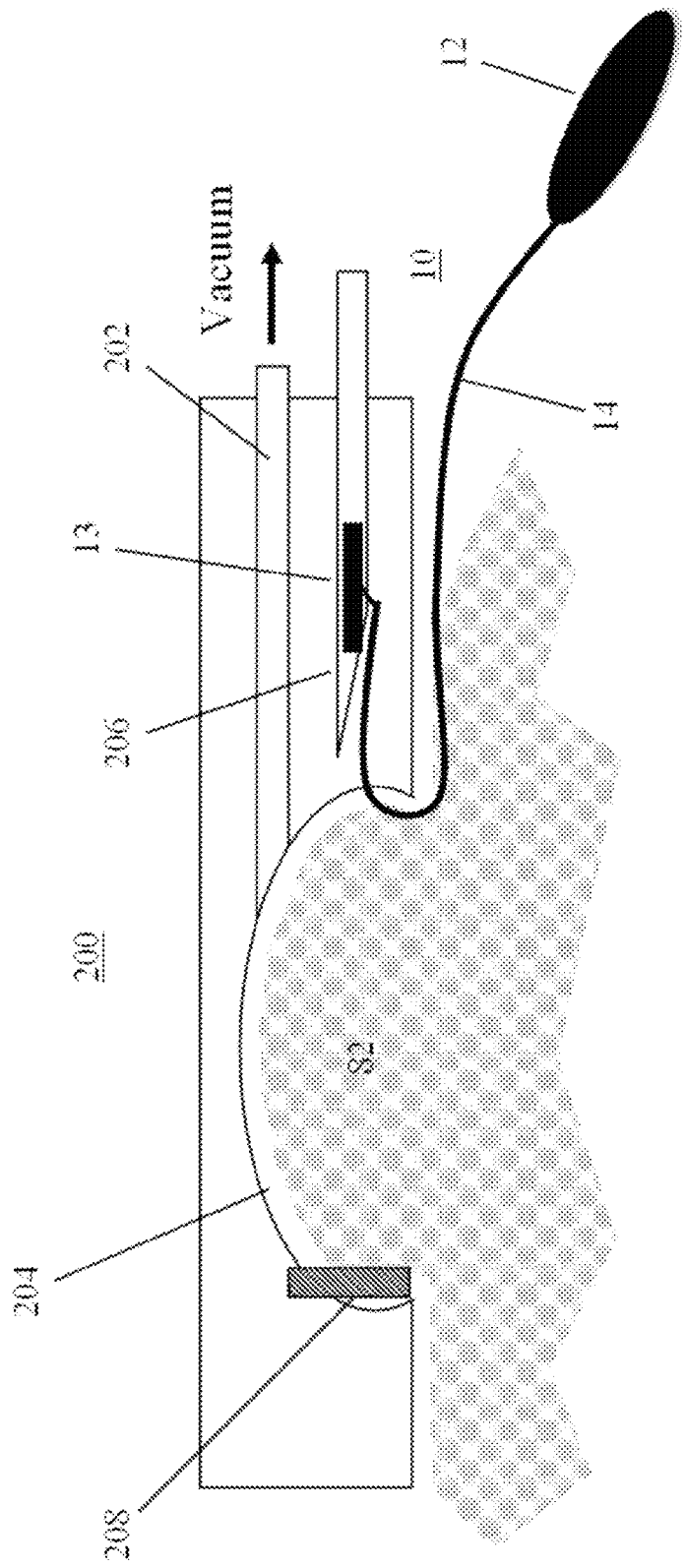
Figure 23B:
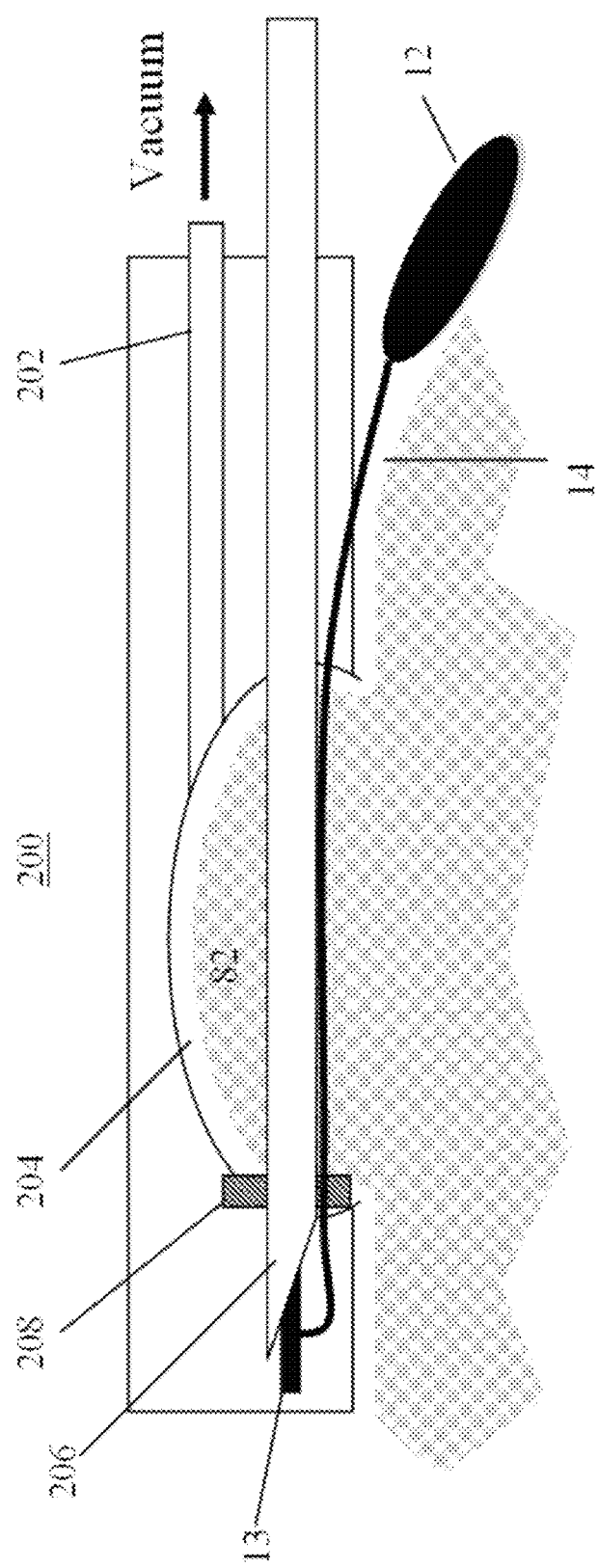
Figure 23C:
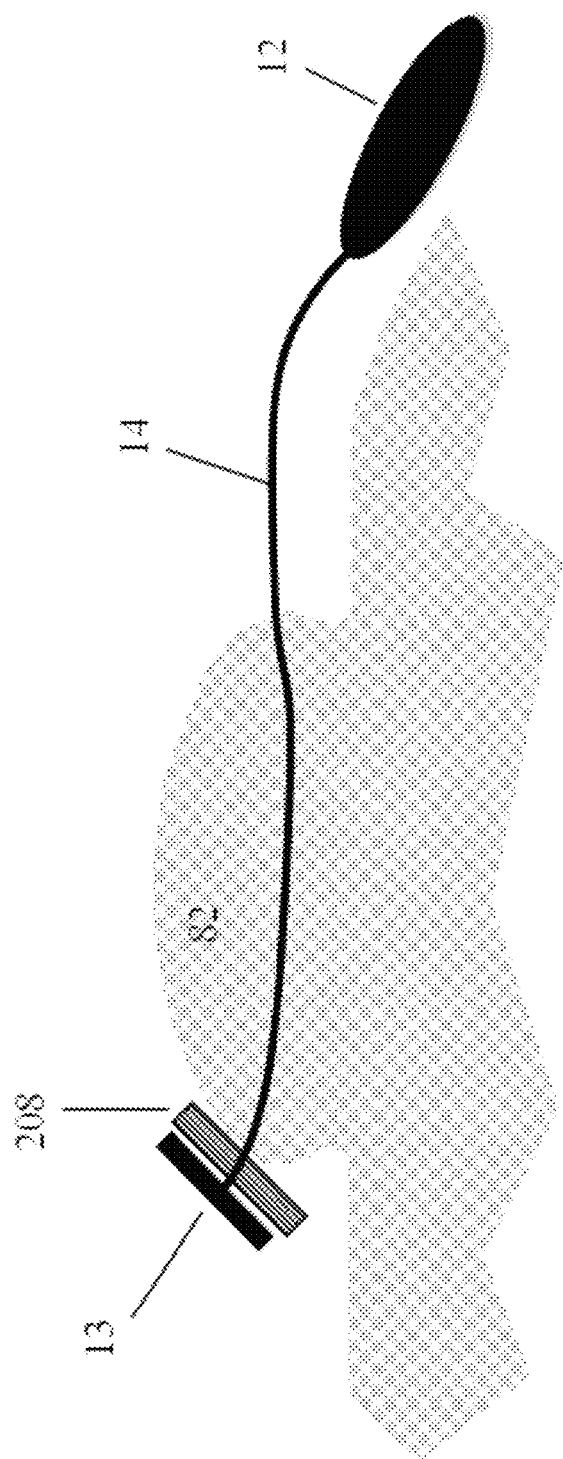

FIGS. 23a-c schematically illustrate operation of a preferred configuration of a delivery device constructed in accordance with the teachings of the present invention.

Figure 24:
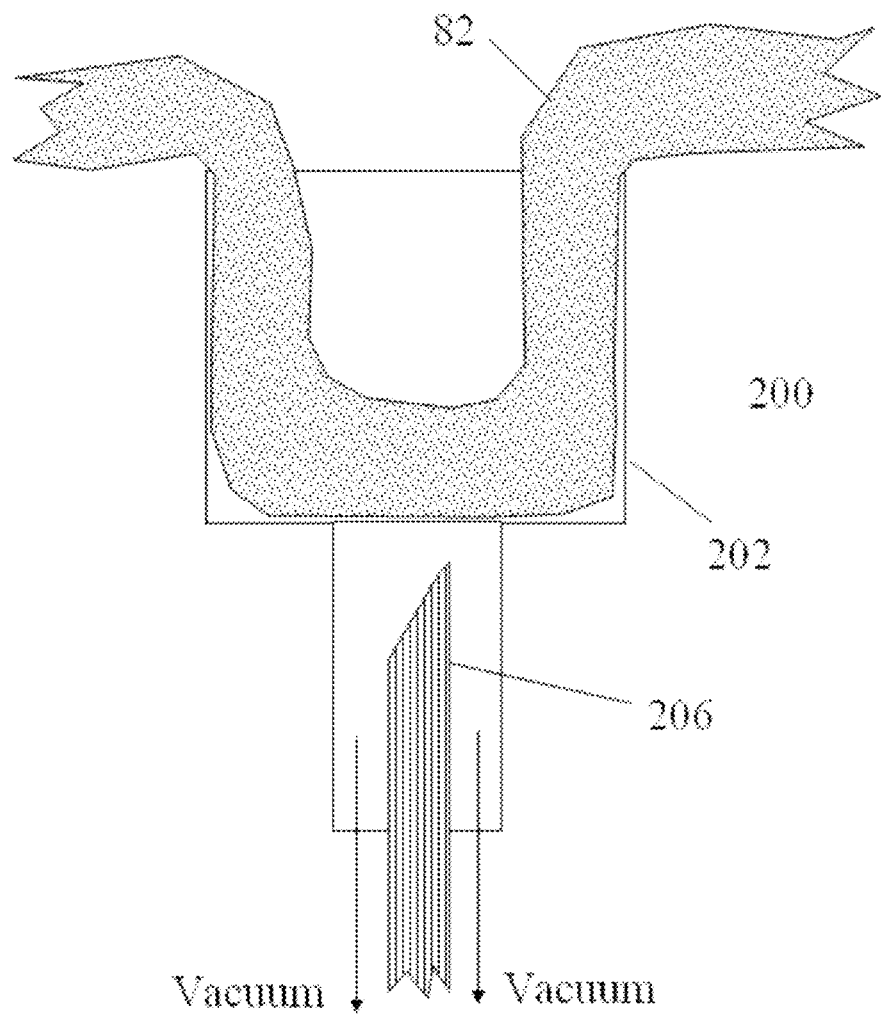

FIG. 24 schematically illustrates a preferred configuration of a vacuum cup for efficient through-anchoring and placement of an anchor outside the wall of a lumen (e.g. stomach).

Figure 25A:
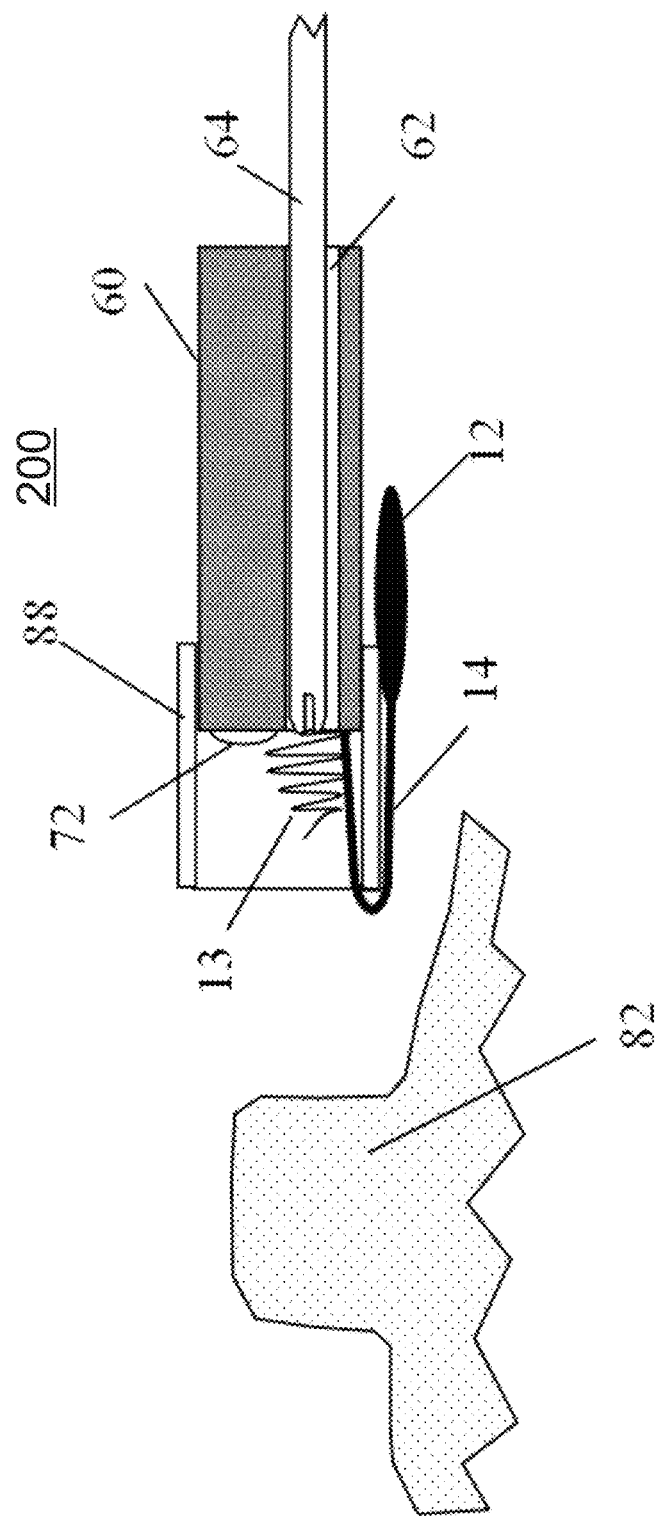
Figure 25B:
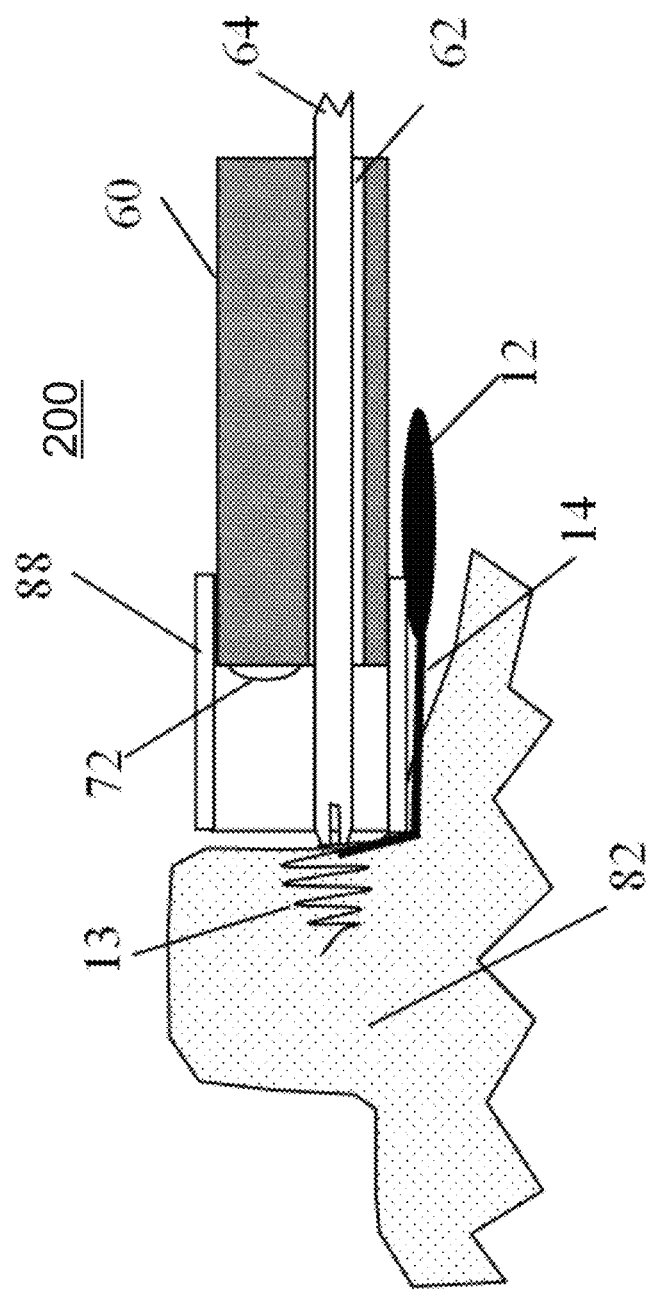
Figure 25C:
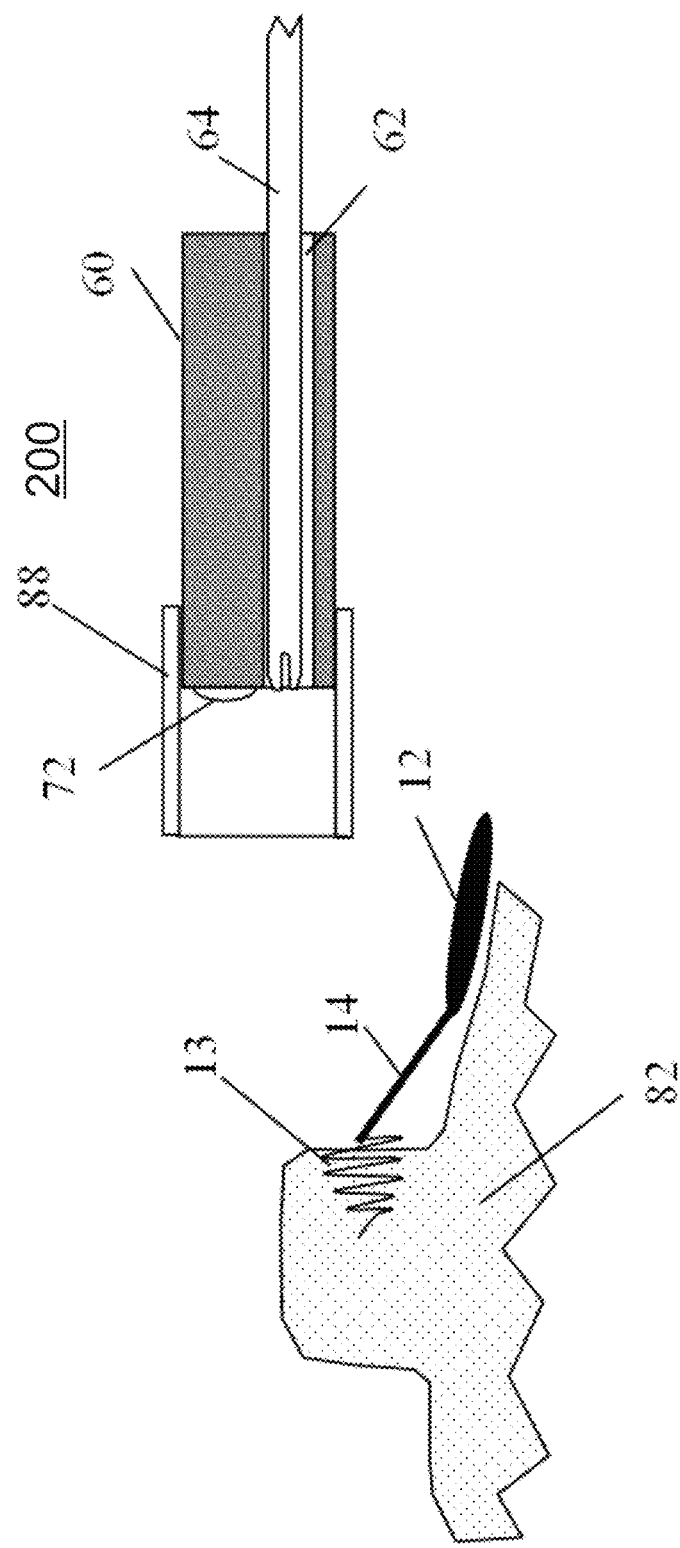

FIGS. 25a-c schematically illustrate in-tissue anchoring of the present device using a coil anchor.

Figure 26:
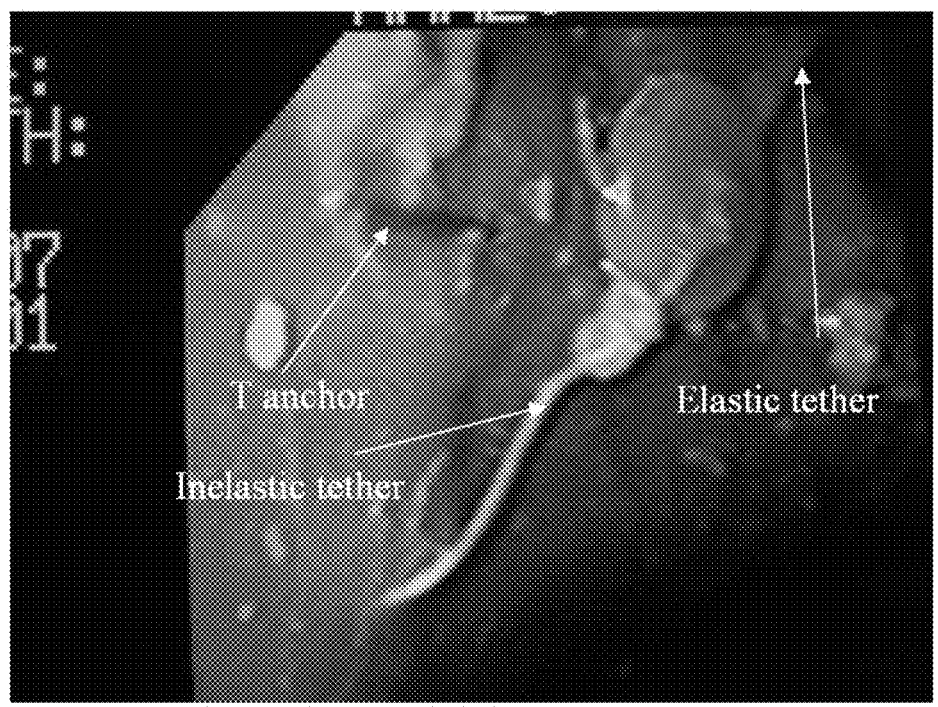

FIG. 26 illustrates anchoring of the device of the present invention in the stomach of a live pig as is described in detail in Example 7.

Figure 27:
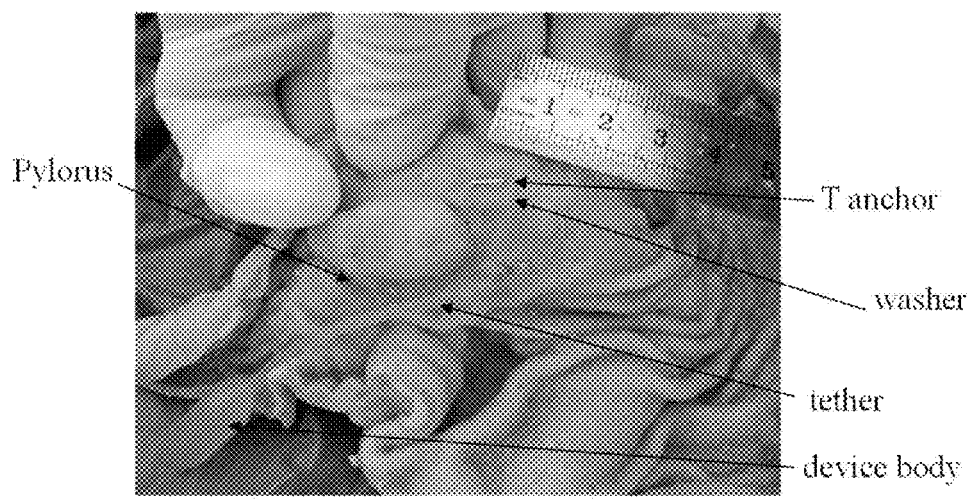

FIG. 27 illustrates pig stomach tissue recovered along with anchored device, showing that anchoring the device of the present invention using the present approach does not result in any tissue erosion or inflammation.

DESCRIPTION OF THE PREFERRED EMBODIMENTS

The present invention is of devices and methods which can be used to alter an eating behavior of a subject.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The pylorus is the region of the stomach that connects to the duodenum (FIG. 1). It is divided into two parts: the distal antrum (DA) or equivalently the pyloric antrum (PA, FIG. 1), which connects to the body of the stomach, and the pyloric canal (PC, FIG. 1), which connects to the duodenum (D, FIG. 1). The pyloric sphincter (PS, FIG. 1), or valve, is a ring of smooth muscle (mu, FIG. 1) at the end of the pyloric canal which is surrounded by the submucosal (SM, FIG. 1) and mucosal (MC, FIG. 1) layers of the GI tract. The pyloric sphincter is part of a system responsible for controlling the flow of food from the stomach to the duodenum. The pyloric opening (PO, FIG. 1) is the opening surrounded by the lips of the pyloric sphincter (PS) and under certain circumstances also includes part of the pyloric canal (PC). Its diameter varies depending mainly on the degree of contraction to and relaxation of the pyloric canal and sphincter. Studies have shown that when fully open, the diameter of the opening can vary between 5-25 mm The stomach plays an important role in the digestion of food by chemically/enzymatically breaking down food particles via secreted gastric acid and pepsin and by mechanically breaking down food particles via peristaltic contractions.

In normal digestion, as the stomach fills, digestive glands in the corpus and fundus release hydrochloric acid, a strong acid that helps digest food and facilitate the conversion of digestive enzymes into their active form. The peristaltic contractions of muscles within the stomach wall, especially in the antral region, mix digestive juices and food to produce a semi-fluid substance known as chyme. Chyme is mobilized into the duodenum through a coordinated antral-pylorus action which is triggered by the consistency of the chyme.

The antrum plays a central role in grinding the food particles into chyme. A representative sequence of gastric emptying events as manifested in the antral/pyloric/duodenal regions is illustrated by FIGS. 2a-c. Although this is believed to be an accurate depiction of gastric emptying in humans, it should be noted that the present device is not bound in function to the specific gastric emptying sequence illustrated by FIGS. 2a-c and thus will also function in the manner prescribed herein during a different gastric emptying sequence.

FIG. 2a-c illustrates the three stages of gastric emptying in the antral/pyloric/duodenal regions. Although these stages occur in one smooth integrated movement, the process is divided into distinct stages for illustrative purposes only. The timing of the closing of the distinct parts of the pyloric cylinder are crucial in determining whether food is evacuated into the duodenum or retropropulsed back into the stomach while simultaneously being ground by the antral mucosal folds. During contraction of the pylorus P (FIG. 2a) there may be an interplay between its right pyloric loop muscles (surrounding the pylorus P) and its left muscle loop (forming the antral contraction wave ACW) in the region of the sulcus intermedius. Should the pylorus (P) close first, retropropulsion and grinding of contents back into the antrum may occur; should the antral contraction wave (ACW) contract first, propulsion and evacuation into the duodenum may occur. In the early phases of digestion (shown in FIG. 2a), an antral contraction wave ACW forces food into the distal stomach against a closed or closing pylorus. In FIG. 2b, the antral contraction wave (ACW) reaches a minimum diameter two to three centimeters proximal to the pylorus (P) at which point the mucosal folds of the antrum touch and grind the food with a bolus of chyme trapped between this point and the closed pylorus (P) in a space called the pseudodiverticulum (PD) in a process called grinding and retropropulsion (see Keet et al., The Pyloric Sphincter Cylinder in Health and Disease, online edition). The contents of the pseudodiverticulum (PD) are not intended to be transferred into the duodenum at this stage. At a later phase of digestion (termed evacuation, shown in FIG. 2c), when the pylorus is patent and does not restrict flow, the antrum contraction wave (ACW), differences in static pressure between the antrum (A) and the duodenum (D), and/or the formation of a pyloric canal (PC in FIG. 2c indicates the muscles forming the pyloric canal) evacuates the contents of the pseudodiverticulum (PD) into the duodenum (D) (see Keet et al., The Pyloric Sphincter Cylinder in Health and Disease, online edition).

Physiological reflexes in the form of electrical, hormonal, chemical or muscular signals are initiated from the duodenum in response to the presence of an excess or change in the composition or characteristics of chyme. Such signals are relayed back to other regions of the GI tract (e.g. pylorus and antrum) to slow or even stop food churning and/or stomach emptying; in addition, satiety-inducing (hormonal or electrical) signals are relayed to the brain (Guyton and Hall Textbook of Medical Physiology, pages 785-6; 2006).

Thus, the antro-duodenal region of the stomach plays an important role in digestion and feedback.

While reducing the present invention to practice, the present inventors have uncovered that anchoring of a device within the stomach in a manner enabling contact between the device body and the wall of the antrum, pylorus or duodenum leads to a reduction in eating rates and weight gain in a large mammal. As is illustrated in the Examples section, implantation of one embodiment of the present device in pigs led to marked decrease in weight gain (see FIGS. 11-12 for a graphical summary of the results).

Thus, according to one aspect of the present invention there is provided a device for modifying an eating behavior of a subject. As used herein, the term subject denotes an animal, preferably a mammal such as a human, e.g. a human having an eating disorder or a weight related disorder.

A presently preferred embodiment of the present device includes a device body which is directly or indirectly attachable to tissue of an antrum or a pylorus in a way which enables the device body to intermittently contact an adjacent or opposite wall region of an antral-duodenal region when attached to said tissue of the antrum or the pylorus. As used herein, the phrase "antral-duodenal region" denotes any mucosal tissue residing within a region of the gastrointestinal (GI) tract starting at the proximal antrum and terminating at the distal duodenum.

It will be appreciated that although antrum or pyloric anchoring is presently preferred, other GI tract anchoring sites (e.g. body of the stomach, fundus, lower esophageal sphincter etc) are also envisaged.

Preferably, this embodiment of the device of the present invention is configured so as to intermittently contact mucosal tissue residing within the antrum, pylorus and proximal region of the duodenum (duodenal bulb), as well as the duodenal side of the pylorus.

FIGS. 3a-c illustrate several configurations of this embodiment of the present device which is referred to herein as device 10.

Device 10 includes a device body 12 and a tether 14. When device 10 is in use, an end 16 of tether 14 is attached to tissue of the antrum. Such attachment can be facilitated via a loop of the tether material itself, a t-bar anchor, coil, suture thread, staples, clips and the like. Preferably, an end 16 of tether 14 is inserted into the antrum tissue (through the mucosa, submucosa and optionally muscle and serosa) and either affixed to itself in a loop with a knot or other swaging device, or secured via a tissue anchor.

Tissue anchoring is classified herein as through-tissue or in-tissue anchoring. In-tissue anchoring implies that the anchor and part of the tether rests within the tissue (e.g. anchored with an in-tissue coil or barb). In-tissue anchoring is exemplified by FIGS. 25a-c. Through-tissue anchoring involves having the anchor reside outside the lumen or with the anchor residing inside the lumen and only part of the tether residing in the tissue itself. Through-tissue anchoring is exemplified by FIGS. 13 and 23a-c. Through-tissue anchoring can be effected with a needle using direct visual guidance through the working channel of an endoscope (see FIGS. 16-18). Alternatively, a vacuum cup can assist in through-tissue anchoring. With reference to FIG. 24, to apparatus 200, which includes a vacuum chamber which is symmetrically arranged around a delivery needle 206 can be used to effect the in-out anchoring scheme. Centering needle 206 in vacuum chamber 202 (cup) ensures the needle 206 follows the shortest path through tissue 82. In this manner, it is not necessary to approach tissue 82 at a normal angle which is difficult to do using an endoscope at any given position in the GI tract. Rather, the endoscope tip is positioned roughly normal and vacuum chamber 202 forces tissue 82 to be flat against the bottom of the cup and normal to the axis needle 206 penetration. If needle 206 is not centered in the vacuum chamber 202, needle 206 could go into the wall of tissue 82, but not penetrate to the other side as tissue 82 around the circumference of vacuum chamber 202 is not normal to axis of needle 206.

Suitable tissue anchors for both in-tissue and through-tissue anchoring can include t-bar or mushroom-like elements which can be buried within the tissue or juxtaposed against the tissue at the exit site. Methods of inserting such anchors include open surgery, laparoscopic or endoscopic means known in the art and developed for such procedures, e.g. natural orifice transgastric endoscopic surgery (NOTES). Additional approaches for anchoring the present device are described in Example 5.

In any case, and with further reference to FIG. 3a-d, tether 14 is attached to the tissue of the antrum in a way which ensures a secure connection which can withstand the forces acting on device body 12 and tether 14 during GI tract movements. Tether 14 or anchor 16 can be designed to degrade and detach after a set time in the acidic or bile environment of the stomach or duodenum respectively. In this manner, device 10 can be designed to remove itself after a set time and device 10, or components thereof, can pass through the GI tract and be removed from the body.

Device body 12 can be fabricated from a wide range of biocompatible materials. Examples of suitable material include polymers such as polyurethane and polypropylene, silicone, latex, Teflon™, ceramics, NITINOL, passive metals, alloys and the like.

Additional coatings for preventing biofilm formation, encapsulation, erosion and antigenic reactions can also be employed. The prior art is replete with examples of materials that can be used for such purposes [see for example, Baveja et al. Biomaterials. 2004 September; 25(20):5003-12] or Surfacine™ (www.surfacine.com).

Coatings including medicaments or pharmaceutically active agents are also contemplated herein, examples of active agents include, but are not limited to hormones such as CCK, ghrelin, motilin and the like. Alternatively, coatings which stimulate chemoreceptors (e.g. fat or fat-like substances, sugars and the like) can also be utilized. Non-releasable coatings (e.g. attached through non-degradable linkers) are preferred for prolonged effect.

Furthermore, the device of the present invention can be an endoscopically-refillable reservoir for medicaments, pharmaceutically active agents such as hormones small molecules or other peptides, as well as chemical agents such as, by way of example, hydrochloric acid, which is known to suppress motility when in contact with the duodenal mucosal surfaces.

Again with reference to FIGS. 3a-d, device body 12 is preferably sized and configured so as to minimize any direct effect on antro-pyloro and antro-duodenal flow of chyme. Preferably, device body 12 is sized and configured so as to not have any substantial direct effect on such flow. Furthermore, device body 12 is selected of a length and diameter so that it can pass safely through the duodenum if it becomes detached from tether 14 or the anchoring tissue, thereby minimizing the risk of a blockage of the small intestines.

Thus, a volume of device body 12 is typically selected from a range of 0.03-12 $cm^3$. Such volume can be distributed over a cylindrical shape, having a length of 1-4 cm and a diameter of 0.1-2 cm. Other shapes contemplated herein include spheres, ellipses (e.g. egg or torpedo-shaped), discs, cubes, triangles, protruding fingers, amorphous shapes and the like. The surface of device body 12 is preferably smooth so as to minimize any shear forces applied to mucosal tissue of the antrum, pylorus and/or duodenum and to minimize the chance of bezoar formation around device body 12, but also potentially ridged to better stimulate the tissue. The surface of device body 12 can be porous, pitted or shaped in the form of one or more cups to retain a bit of chyme on the device surface via capillary forces and therefore prolong the stimulation of the chemical sensors in the duodenum that sense the presence of chyme, hence slowing gastric motility.

Device body 12 can be fabricated using any one of several well known fabrication techniques including, but not limited to, casting, extrusion, machining and the like.

A device body 12 fabricated from silicone having a Shore A hardness range of to 5-100 is presently preferred for its biocompatibility, durability and low surface hardness. It is preferable that all parts of the device that are in contact with the submucosa of the GI tract are soft enough to bend, deform and extend elastically to a degree sufficient to not cause erosion of the mucosal surfaces despite the pressure and motion exerted on the device by the GI tract.

Device body 12 can be attached directly to the GI tissue with anchor 16 if excessive movement relative to the anchoring point is not desired. Alternatively, the length and composition of tether 14 is selected according to the intended function of device 10. The length of tether 14 can be anywhere from 0.5 cm to 10 cm and largely depends on the site of attachment of end 16 and function of device 10. Tether 14 can be rigid or elastic; a rigid tether 14 can be fabricated from a polymer (e.g. polyethylene, PTFE, or nylon); while an elastic tether 14 can be fabricated from silicone, polyurethane, latex, and the like. The elastic tether can have an elastic configuration and yet be made from a non-elastic material, e.g. a coil made from a polymer, or it can be fabricated from an elastic material such as silicon. A tether having a first portion which is elastic and a second portion which is not elastic can also be utilized by the present invention.

In a preferred embodiment, tether 14 is made of a highly elastic material such as silicone and will extend like a rubber band, thereby minimizing the forces acting to rip device 10 out of its anchored position. Typical diameter of tether 14 can be anywhere from 0.1 mm to 1 cm.

As is mentioned herein, device 10 of the present invention is configured so as to enable intermittent contact between device body 12 and wall tissue of an antral-duodenal region. Such functionality can be achieved via one of three general configurations of device 10.

FIG. 3a illustrates a configuration which enables device body 12 to move within or shuttle between the antrum and duodenum and thus intermittently contact a wall tissue of the duodenum, pylorus and/or antrum.

Tether 14 length and device body 12 size are preferably selected such that when device body 12 resides within the duodenum, it does not go more distal than the first 10 cm, preferably, first 5 cm of the duodenum.

Tether 14 and device body 12 of this configuration of device 10 is preferably to fabricated from silicone. Tether 14 length can be anywhere from 0.5 cm to 10 cm, while device body 12 can be shaped as a cylinder or torpedo having a volume of about 4 $cm^3$ or less and/or with surface area of 15 $cm^2$ or less. Attachment of device body 12 to tether 14 can be effected via gluing, pinning and the like. Alternatively, device body 12 and tether 14 can be cast as a single part and be of unitary construction.

Due to the length of tether 14 and the shape and size of device body 12, this configuration of device 10 will shuttle or move within or between the antrum and duodenum through the pylorus due to natural peristaltic and reflux forces present in the GI tract and thus intermittently contact mucosal tissue of the duodenum, pylorus and antrum.

Such intermittent contacting will be largely influenced by movements of the GI tract (e.g. peristaltic movement of the antrum and duodenum as well as sphincter movement of the pylorus) as well as flow of chyme from the antrum to the stomach body (retropropulsion) or from the antrum to the duodenum and bile reflux from the duodenum to the antrum. Flow of chyme from the antrum to the duodenum, will carry device body 12 into the duodenum (as shown by I), while retrograde flow of bile from the duodenum into the antrum may carry device body 12 into the antrum (shown by II). Such shuttling back and forth can occur 2 to 3 times per minute when the subject is feeding. Without being bound to a theory, the present inventors are of the opinion that such shuttling will activate receptors present in the duodenum and antrum and thus reduce eating rate and/or eating amount.

FIG. 3b illustrates a configuration of device 10 in which device body 12 resides in the duodenum intermittently contacting mucosal tissue of the duodenum and pylorus and does not shuttle into the antrum. In this configuration of device 10, tether 14 is attached to pylorus, antro-pylorus or duodeno-pylorus tissue (mucosa, submucosa and optionally muscle) and is long enough to allow device body to intermittently contact the wall of the duodenum and the pylorus (at the duodenal side). Device body 12 can be shrunk to dimensions of tether 14 and therefore contact of the GI tissue with tether 14 alone (or tethers if multiple devices are present) will be sufficient to create the desired change in the eating behavior of the subject.

It will be appreciated that device 10 configuration also enables application of back pressure on the pylorus wall (at the duodenal side) especially when bile flows from the duodenum to the antrum. The duodenum does not normally contain food particles, and therefore any such pressure or mechanical stimulation of a solid substance may generate a signal that solid food has managed to get into the duodenum, and that in turn may drive signaling to slow down gastric motility in general.

FIG. 3c illustrates a configuration of device 10 in which device body 12 resides in the antrum intermittently contacting mucosal tissue of the antrum and possibly the pylorus and does not shuttle into the duodenum.

In this configuration, tether 14 is attached to tissue of the antrum and is long enough such that device body can contact the walls of the antrum, as well as walls of the pylorus (at the antrum side and optionally the opening).

Device 10 of the present invention provides several advantages over prior art devices which reside in the antrum and/or duodenum.

Most antrum/duodenum devices, such as, for example, the antrum-anchored balloon described in U.S. patent Ser. No. 10/872,910, the artificial bezoar described in U.S. Pat. No. 7,066,945 or the flow reduction devices described in U.S. patent application Ser. No. 11/300,283 function by directly reducing the flow through the antrum, pylorus and/or the duodenum or by occupying a space within these regions thereby effectively reducing the volume thereof.

In sharp contrast, device 10 of the present invention is designed for leveraging innate mechanical, neurological and biochemical feedback mechanisms that control GI motility and that arise from the stimulation of the lumen of the GI tract and interference with the normal peristaltic sensations of the lumen.

It will be appreciated that the present invention can also utilize configurations which include several implanted devices.

FIG. 3d provides one example of such a multi-device 10 configuration. In this example, two devices are utilized each being separately positioned in a specific location of the antro-duodenal region. A first device 10 is positioned so as to reside in the duodenum and a second in the antrum. Such a configuration (which can also be realized using a single tether-attachment location) effectively stimulates both regions simultaneously.

Another example of a multi-device configuration includes 2-5 device 10 configurations each including device body 12 shaped as a hollow or solid sphere having a volume of about 1 cm$^3$. Each of the devices can be individually tethered to one or more tissue locations in the antrum or duodenum. The surface of such a sphere can smooth or provided with projections. In this embodiment, the effective volume and surface area of the combined devices is increased linearly with the number of devices implanted, which increases their stimulation capability, while the size of each individual device 10 is kept to a minimum to enable easy introduction into the stomach, easy anchoring, minimize the forces on each device 10, and ensure that each device 10 is small enough to safely pass through the small intestine if it becomes detached from the tissue to which it is anchored.

It will be appreciated that although the device configurations described above include a tether 14, it should be noted that direct attachment of device body 12 to the tissue, at least in the case of the device illustrated in FIGS. 3c-d is also contemplated herein. Such direct attachment can be realized using clips, staples, barbs, sutures and the like.

Since it is possible that device body 12 functions in stimulating mechano-receptors present in the walls of the duodenum antrum and pylorus, the present inventors have also devised device body 12 configurations which maximizes surface contact and stimulation of mechano-receptor and while minimizing flow obstruction.

Figure 4A:
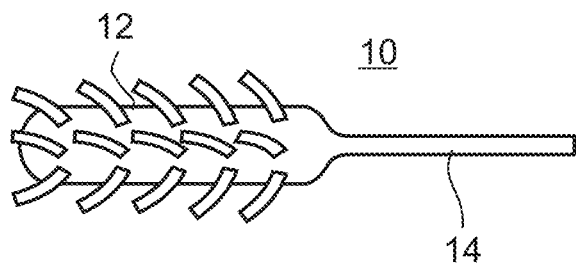
Figure 4B:
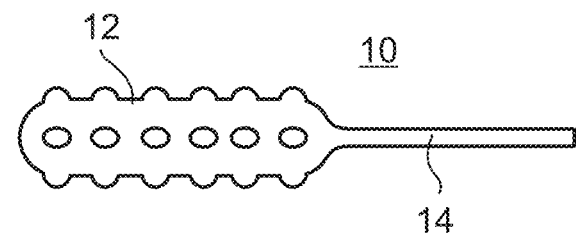
Figure 4C:
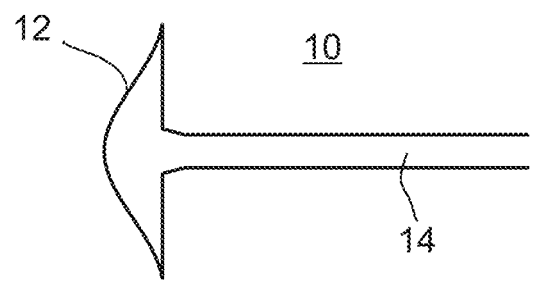
Figure 4D:
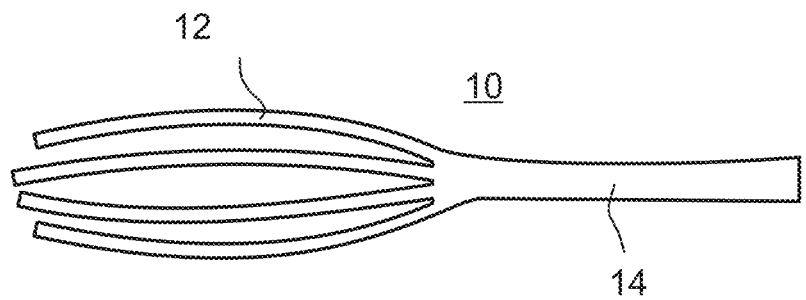

FIGS. 4a-d provide several examples of such device body 12 configurations, including a device body 12 which incorporates whiskers (FIG. 4a), soft projections (FIG. 4b), flat discs for applying back pressure on the duodenal side of the pylorus (FIG. 4c) and spaghetti- or ribbon-like extensions (FIG. 4d). The example configuration depicted in 4c can also serve as a one way flap valve to prevent reflux of GI contents from one side of a sphincter to the other, and if so engineered to resist flow in the forward direction as well. Device body 12 can also incorporate at least one concavity which can act as a surface reservoir.

Device 10 can also incorporate several other mechanisms for enhancing its effect in inducing early satiety.

For example, device 10 can include electrodes positionable on device body 12 and powered by a power source positioned at the site of tether 14 attachment. Such a power source can be a battery, or a self contained power generating device (further described hereinunder). Tether 14 can include insulated wires for carrying the current produced by the power source to the electrodes positioned on the surface of device body 12. Since device body only intermittently contact tissue, an electric current will be periodically applied to the tissue.

The power source can also be configured such that the acid in the stomach is used to generate electricity. In this embodiment, pieces of metal, for example zinc and copper are electrically isolated from one another in the antrum but both exposed to stomach acid. The electric current is generated by the chemical reaction between the acid in the stomach and the zinc. The reaction occurs according to the following:
At the anode, zinc is oxidized:

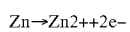

At the cathode, hydrogen is reduced:

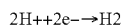

The insulated wires connected to the pieces of zinc and copper run the length of the tether and end in one of more bipolar electrodes that electrically stimulate the duodenal tissue as device body 12, or protrusions thereupon randomly contact the duodenum tissue during peristalsis and passage of chyme.

The electricity generating power source described above can stimulate the pylorus or antrum in addition or instead of electrical stimulation of the duodenum. In the antrum-only example, the stimulating electrodes can be a part of the anchoring mechanism, or as separate flexible protrusions that are free to move around and contact the mucosal surfaces of the antrum randomly, thereby providing a combined electrical and mechanical stimulation of the antral tissue.

Electrical stimulation of the GI tract tissue can also be effected using electrodes embedded in the mucosal, submucosal or muscle layers of the stomach using endoscopically-introduced electrode anchors or screws and thereby be used to alter (enhance in the case of gastroparesis or delay in the case of obesity) gastric motility using electrode positions and stimulation parameters known in the art. Many external gastric stimulators are known in the art. The device described herein can be introduced and implanted using an endoscope, which is significantly more tolerable than an open or laparoscopic surgical procedure used in existing gastric electrical stimulators.

The device described above can run open loop, i.e. only turns on when a subject is eating and gastric acid is being generated. Furthermore, the device requires no external power source with the requisite change or recharging of batteries. Alternatively, the device can have an on board battery or capacitor to store excess energy for future use, onboard electronics to regulate and condition the stimulation parameters, interface with sensors that detect parameters such as the current pH, presence and composition of food, as well as wireless communication capabilities to allow for control of the device from outside the body.

At some point, the zinc will be fully degraded and the device can be recharged with new zinc, or the entire device can be replaced. For example, the metals can be replenished orally using the magnetic retention mechanism describe elsewhere in this patent application Material substitutions are possible. Carbon can be used instead of copper for example. Other metals can be also be used. For example, using a piece of magnesium instead of zinc approximately doubles the current produced by the device (approx. 240 μA with zinc to about 400 μA with magnesium in 5% citric acid) and increases the voltage (0.97 V with zinc to 1.6 V with magnesium in 5% citric acid). Even higher voltages and currents are anticipated in the hydrochloric acid environment of the stomach with a concentrated pH of 0.8 and a diluted pH of 2-3. Two or more such devices can be wired in series to increase the voltage or in parallel to increase the current they supply to whatever level needed to provide effective stimulation.

Studies have shown that the presence of acid in the duodenum can trigger satiety feedback signals and/or slow gastric emptying and motility. Thus, device 10 can also include a mechanism for carrying gastric acid from the antrum to the duodenum, thereby bypassing the pyloric valve. Such a mechanism can include a collector positioned at the site of tether 14 attachment. Such a collector can be a gel or porous polymer (such as porous PTFE or polypropylene) which imbibes the gastric acid without getting clogged by food particles or chyme. Tether 14 can include a conduit for relaying collected gastric acid through the pylorus to the surface of device body 12 present in the duodenum. Contact of device body 12 with duodenal tissue can release the acid, or alternatively contractions and increased pressure within the antrum can create a pressure difference to delivery the acid through the conduit. In addition to acid, the conduit described above can convey liquid chyme, which can include sugars, fats and other components that can cause a dumping effect which will reduce eating to rate and eating amount. In an alternative embodiment, device 10 can contain solid tether 14 shaped so that it will not allow the pylorus to seal properly in order to allow chyme to be transferred prematurely into the duodenum to induce a slight dumping effect.

In a further embodiment, device 10 comprises an anchorable balloon that resides in antrum and is filled with a gas or liquid. Tether 14 forms a conduit to transfer the fluid or gas to body 12 on device 10 that is present in the duodenum. When the antrum contracts the balloon in the antrum, fluid or gas is transferred through the conduit in tether 14 and inflates body 12 which then mechanically stimulates the duodenum, thereby affecting the eating behavior of the subject.

As is mentioned hereinabove, device 10 functions to modify an eating behavior of a subject by possibly activating mechano-receptors which induce early satiety and/or a slowing of gastric emptying and motility.

Several approaches for implanting device 10 are contemplated herein, including open surgery, laparoscopic surgery and endoscopic surgery.

In the open surgery approach, a physician gains access to the antro-pyloro region through a full incision and anchors/sutures end 16 of tether 14 to the antral or pyloric tissue. Following anchoring the physician places device body 12 within an antral or duodenal region and closes the stomach and skin incisions.

The laparoscopic approach is largely similar with the only major difference being replacement of the open incision with three or more small incision through which the device can be guided into position using laparoscopic equipment.

A combined laparoscopic and endoscopic procedure can be used as well. A laparoscope can be introduced and positioned so that it impinges on the external surface of the stomach where the anchoring is desired. The impingement can be viewed from inside the stomach using an endoscope and the endoscope maneuvered to anchor the device at the point of impingement. The laparoscope can then be used to manipulate the anchor on the external surface of the stomach (for example guide it back into the stomach) or simply to confirm that the anchor site has no long term bleeding or other complications.

Endoscopic placement of device 10 of the present invention can be facilitated using an endoscope-mounted/delivered guide. The endoscope can be temporarily anchored against the distal end of the pyloric sphincter using an inflatable balloon in to order to facilitate placement and anchoring of device 10 using the endoscope-mounted guide. Alternative methods known in the art for determining the position of the guide include direct visual feedback, fluoroscopic guidance, and potential or pH differences between the pyloric antrum and the duodenum. The guide can be advanced through the working channel of a GI endoscope.

Device 10 can then be advanced to the site of implantation, or it can be preloaded onto the endoscope end. Alternatively, device 10 can be configured for ingestion such that it is temporarily located in the stomach or trapped there by virtue of its size to not pass through the pylorus. Device 10 in such a configuration can be wrapped with an acid-sensitive coating that protects the esophagus of the subject swallowing the device and then the coating dissolves and device 10 unfolds and exposes its anchoring mechanism. Following ingestion, an endoscope mounted guide can be used to capture the device, position and anchor it in the relevant tissue. It will be appreciated that in such a delivery approach, device reconfiguration following capturing is preferred since once device 10 is attached to the tissue it should be capable of passing through the pylorus (i.e. achieve shuttling if need be, or be passed down the GI tract and excreted without causing blockage in case tether 14 detaches from the tissue). An example of a device configuration which can be delivered via ingestion is a multi-device configuration which includes several devices attached to antrum tissue. In such a scenario, the devices can be ingested as a single unit which is large enough not to pass through the pylorus. Once trapped in the antrum, a guide can be used to separate and individually position each of the devices. Following positioning and antral tissue attachment each device is now capable of shuttling through the pylorus (if so desired) or passing through the GI tract if accidentally detached.

Regardless of the approach used for delivering device 10, once device 10 is positioned, tether 14 is attached to the mucosa/submucosa and optionally muscle using sutures, staples, clips or by running end 16 of tether 14 through the tissue and anchoring it within the tissue or providing or deploying a back stop (e.g. t-bar) at the site end 16 exits the tissue. Such attachment can be facilitated by a mechanism disposed on the end of the guide. The mechanism can be an auto-suturing or an auto-stapling mechanism. Following implantation the guide and endoscope are retracted.

Any of the above surgical approaches can be effected using a two separate procedures. In a first procedure, an anchor for tether 14 is established, while in the following procedure, device 10 is reversibly or permanently attached to the anchor point.

The anchor point can be a loop of silicone (configured like an O-ring) which is implanted into an incision made in antrum tissue; the incision is closed such that a portion of the loop remains exposed in the antrum. Once the tissue heals around the silicone, device 10 is attached onto the exposed loop portion via a device positioning procedure. The configuration described above can allow for rapid installation, removal or exchange of different sized or configured device bodies based on the need of the subject, without needing to place additional anchors or make any further incisions or punctures into the tissue.

The above described devices can be anchored to stomach tissue using non-elastic or elastic tethers. Preferably, the device of the present invention is anchored to stomach tissue via at least one tether configured for elastic compliance. Human tissues are dynamic and the forces and strains generated by tissue movement can be large enough to cause non-compliant sutures or tethers to cut through or rip out of tissue or erode surfaces such as mucosa. This is especially true if a non-compliant suture or tether attempt to constrain the normal motion of the tissue or is in a geometry that does not allow for relative motion between itself and the tissue. Therefore, compliant anchoring as taught by the present invention is preferred as it does not constrain the tissue from its natural movement and thus minimizes the chances of anchor failure and tissue erosion.

Anchoring of the device body is effected using an elastic tether which is attached to a tissue anchoring element suitable for providing in or through—tissue anchoring capabilities. Examples include t-bar structures, barbs, coils, pig-tail structures (e.g. anchoring elements which form coiled pig tail structures when relaxed and linearize when forcibly pulled), umbrellas, balls (expandable, static, hollow, solid or wire) screws, augers, or any other structures capable of residing in or against a tissue and opposing a force applied thereto in one or more directions, whether designed to be permanent or removable.

The tissue anchoring element can be fabricated from any material including metals, alloys, polymers and the like. The anchoring element structure can be rigid, compliant or elastic in nature. The anchoring element can be constructed from a combination of materials which provide the rigidity necessary for resisting forces applied to the anchor while maintaining a soft non-traumatic interface with the tissue, thereby minimizing tissue abrasion. For example, a t-bar anchoring element can be constructed by overmolding a rigid plastic or metal bar or wire with silicone to form a T which has a silicone covered cross bar and a silicone tether stem. The use of overmolded metal also provides the anchoring element with radio-opacity and thus enables identification thereof using imaging techniques. Alternatively part or all of the anchor, tether and body of the device can include a radio-opaque material during fabrication, such as barium sulfate.

The loading capabilities of the anchoring element are determined by a combination of structure, size and choice of materials. It will be appreciated that such loading capabilities can be designed into the anchoring element according to use and site of anchoring.

As used herein, the phrases "elastic properties" or "elastic compliance" are used interchangeably to refer to the ability of the tether or a portion thereof to reversibly increase in length under a pulling force. Such an increase in length can be at least 10%, preferably at least 25%, more preferably at least 50%. The elastic properties of the tether can be provided by the tether structure, cross sectional and axial geometries and/or tether material.

The tether can be a hollow or solid thread or string-like structure which includes one or several adjoined portions. The tether can be made out of a twisted or braided set of smaller elastic filaments, much like a bungee cord. Such a braided design will allow cell ingrowth and better integration into the host tissue, A tether constructed from two adjoined portions can be used to provide a unique elastic profile, wherein one portion elastically stretches and another does not, or where both portion stretch, each to a different degree. A multi-portion tether configuration can also be used to simplify construction of the anchor of the present invention. For example, the anchoring element and a first portion of the tether can be molded from a single material and attached to a second and elastic portion of the tether via gluing, press fit, over-molding and the like. A multi-portion tether configuration can also be used in cases where different portion are exposed to different environments, for example, when a first portion of the tether resides within a tissue and another in a lumen. The tether material can be inelastic and yet the tether can be configured to provide elasticity, e.g. an elastic coil structure. For example, the tether can be inelastic and be wound around a rotary-spring-loaded drum in the device body to allow for an elastic effect with inelastic materials.

FIG. 13 illustrates one preferred configuration of the present device as anchored into tissue.

Device 10 includes a device body 12 which is anchored into tissue of the GI tract.

In a preferred configuration of device 10, tether 14 (which in this case is composed of an elastic portion 17 and an inelastic portion 19) is provided with an anchoring element 13 which enables, through-tissue anchoring. To enable through-tissue anchoring, anchoring element 13 and attached inelastic portion 19 of tether 14 are delivered from within the stomach through stomach wall tissue or a GI sphincter (as described hereinbelow) and anchor element 13 is deployed and juxtaposed against the outermost tissue layer (serosa) of the stomach, through and against the inner luminal surface of an invaginated tissue fold in the lumen of a GI tract, or against the backside of a sphincter such as the duodenal side of the pyloric sphincter or the stomach side of the lower esophageal sphincter.

Through-tissue anchoring is preferred for its anchoring strength. While experimenting with several tissue anchoring designs, the present inventors have discovered that devices anchored within stomach tissue (e.g. through stomach wall, a tissue fold or through a sphincter) using through-tissue t-bar anchoring and elastic tethers resulted in consistent anchoring results while minimizing tissue necrosis and damage at the site of tissue penetration (see FIGS. 20a-h).

Anchoring through a sphincter or a tissue fold is advantageous in that the anchoring element is maintained on the luminal side of the GI tract. This feature ensures that the anchoring element is released into the GI tract when disconnected from the tether and can be recovered or harmlessly passed out of the body. Keeping the anchoring element on the luminal side of the GI tract can also be achieved with stomach wall anchoring by simply delivering the anchoring element and attached tether out of the stomach through a first hole and back in through a second hole. This can be effected by forming a tissue fold from the stomach wall or by utilizing a device that provides stitch-like functionality (see for example FIG. 23a-c). The tether can be anchored to the tissue using an anchoring element or the tether can be secured via knotting or the like.

The tether can also include a stopper structure for limiting movement of the tether and/or anchoring element in an unwanted direction. For example, with reference to FIG. 13, in cases where tether 14 is anchored through the stomach wall, e.g. when anchoring element 13 is positioned outside the stomach against the serosa or in cases where tether 14 is secured through the tissue in an in-out-in configuration, a stopper 20 can be provided on the tether to prevent movement of the tether in the direction of the tissue, particularly as it has been discovered by the present inventors that the omentum tends to pull any objects, such anchor 13, away from the serosa surface of the stomach. Additionally or alternatively, a washer can be used for preventing an anchor positioned against a tissue (e.g. a t-bar anchor) from burying into and eroding out of the tissue under the pulling forces of the tether. One configuration of such a washer is shown in FIGS. 23a-c which is described in Example 5.

Another embodiment of the present device includes a device body configured for at least partially residing within a pyloric canal and capable of contacting a tissue region of the canal and/or modifying an opening size (as defined by, for example, cross sectional area or volume) of the pyloric canal when a pyloric sphincter is open. Preferably, the device body is also capable of modifying an opening size of the pyloric canal when the pyloric sphincter is closed.

Such a device functions in activating mechanoreceptors present in the pyloric canal; reducing a maximal opening size of the pyloric canal when the pyloric sphincter is fully open and/or increasing the opening of the pyloric canal (i.e. preventing complete closure) when the pyloric sphincter is fully closed.

FIG. 5a illustrates a pyloric device 100 (also referred to herein as device 100) which includes a device body 102 which is curved with opposing concave and convex surfaces (similar to a cashew nut) and attached anchoring mechanism (hooks shown).

Device body 102 has dimensions selected from a range of 1-4 cm in length (L, FIG. 5a), 0.5-2 cm in width (W, FIG. 5a) and 0.3-2 cm in height (H, FIG. 5a). Device body 102 can be fabricated from a variety of materials including silicone, polymers, ceramics and alloys or combinations thereof. Device body 102 can be solid or hollow; a hollow configuration can be filled with a gas, liquid (e.g. saline), gel or different hardness solid. Preferably, device body 102 is made from a material soft enough to not cause erosion in the area of the pylorus, for example low hardness silicone.

An inflatable configuration of device 100 can include a port for filling device body 102 which can be fabricated from a thin silicone shell, and as such at least one dimension thereof (e.g. height) can be adjusted before, during or following anchoring of device 100. Device 100 can be made from a combination of flexible, inflatable and rigid components. For example, conduit 106 can be constructed from an inflatable inner tube or bladder placed inside a rigid and non-collapsing outer tube to variably set the minimum conduit diameter through the pylorus while body 102 can be inflatable to adjustably block the maximum opening of the pylorus when open or the displaced volume of the region proximal to the pylorus, otherwise known as the pseudodiverticulum. This adjustability allows the doctor to optimize and balance the effects of premature gastric emptying and slowed or less productive gastric emptying for each patient post implantation. Alternatively, body 102 can consist of removable insert elements that reside axially in conduit 106 and outside body 102 that when removed endoscopically increase the inner diameter of conduit 106 or decrease the outer diameter of body 102 post implantation.

Device body 102 serves to activate mechanoreceptors in the pyloric canal by applying (intermittent) pressure thereto, and/or to reduce the volume in the pyloric canal thereby reducing the opening of the canal when the pyloric sphincter is open. Such reduction can be in a range of 10-80%, preferably, 15-50%, most preferably 20-40%. Such a reduction of volume slows down stomach emptying and contributes to a feeling of satiety in a subject.

As is mentioned hereinabove, device 100 can also function in modifying the opening size of the pyloric canal when the pyloric sphincter is closed. When food enters the stomach, the antrum facilitates breakdown of food particles via repeated contraction waves, at the same time, the pyloric canal is closed to prevent passage of partially digest food into the duodenum until the food is broken down by the mechanical action of the antrum. As is described hereinabove, it is believed that premature stomach emptying (dumping) also contributes to early satiety. Device body 102 is preferably also configured to facilitate such dumping by maintaining the pyloric canal partially open when the pyloric sphincter is closed. To enable such to functionality, device body 102 is provided with a conduit 106 which runs axially along the top, convex surface of device body 102. Conduit 106 can be a partially open groove or channel (as shown in FIG. 5a) or it can be a through-hole orifice (as shown in FIG. 5b). In any case, conduit 106 maintains an opening through the pyloric canal when the pyloric sphincter is closed (as shown in FIG. 5c from a side view in the narrow portion of the pylorus muscle P).

It will be appreciated that in the case of an open groove or channel configuration of conduit 106, the material of device body 102 surrounding the groove is preferably rigid enough to resist buckling when pressure is applied thereupon by the tissue. Such rigidity can be achieved via use of materials such as hard silicones, polymers, ceramics or alloys or a combination of such hard materials coated with soft shells fabricated from, for example, silicone rubber, PTFE and the like. Some elasticity and a curling motion in a region of device body 102 surrounding the groove can be tolerated as long as an orifice is maintained within the pyloric canal upon closing of the pyloric sphincter.

One distinct advantage of having an open groove/channel design is substantial reduction in blockage. In cases where such groove is blocked by food particles when the pyloric sphincter is closed, subsequent opening of the sphincter and pyloric canal will release food particles trapped within the groove/channel of conduit 106.

As is mentioned hereinabove, device 100 further includes an anchoring mechanism which in this configuration is attached to device body 102. The anchoring mechanism serves to anchor device body to tissue within and/or adjacent to the pyloric canal. Anchoring mechanism can be used to anchor device body 102 to tissue within the pyloric canal and/or antrum, preferably anchoring is to the submucosa and or muscle layers.

The anchoring mechanism can be any mechanism which can be used to anchor device body 102 to tissue such as mucosa, submucosa and/or muscle. Hooks 108 are shown in the device depicted in FIG. 5a. Although four hooks are shown in FIG. 5a, it will be appreciated that any number of hooks arranged in any pattern along the concave surface of device body 102 can be used for tissue anchoring. Other anchoring configurations which can be used by device 100 include one or more pins 109 which can be inserted through guides disposed within device body 102 and tissue (shown in to FIG. 5d from a side view in the narrowest portion of the pylorus P), sutures which can be used to suture device body 102 to the tissue, elastic tethers (further described hereinbelow), deployable anchors such as those shown in U.S. patent application Ser. Nos. 11/172,082; 10/726/011 and 09/871297 or any combination thereof. Pin 109 can be made of a flexible/elastic material, examples including silicone-covered NiTinol wire, or a braided polyester suture material. Anchors 108 can be a fabricated from a tissue-penetrating material that that swells after implantation and more firmly anchors itself in the tissue with minimum trauma. Anchors 108 can have ends that are inflatable to prevent dislodging. Anchors 108 can interlock with one another in the tissue to increase the strength of the anchor mechanism. Such anchors can be coated with fibrosis-inducing agents so as to induce local tissue fibrosis and enhance anchoring and/or with anti-microbial agents in order to prevent possible infection of anchor site. Anchors 108 can be coated with an elastic or tissue adhesion material to encourage sealing of the submucosa around the anchor thereby reduce the inflow of acid or gastric juices from entering the underlying muscle layers and causing ulceration.

Device 100 can be anchored to one side of the pyloric canal through one or more anchors which can attach to tissue of the pylorus and/or antrum. Such unilateral or tangential anchoring is advantageous in that the device is not subjected to multiple radial forces applied by the opening or closing of the pyloric canal, thus, device 100 simply rides with the pylorus tissue through opening/closing cycles and does not affect pyloric sphincter function rather only pyloric canal opening size. FIG. 5e shows device 100 from the perspective of looking at the pylorus P opening from the stomach in an open pylorus and in FIG. 5f in a closed pylorus. Note that device 100 doesn't experience significant radial forces when the pylorus is open and therefore is more likely to stay implanted without eroding out or causing damage to the surrounding tissue.

FIGS. 5g-h illustrate from a similar perspective an alternative configuration of device 100 of the present invention. In this configuration, device body 102 includes three semi circular members 110 which can be separately anchored or interconnected through a unified anchoring support into the pylorus P tissue and optionally extending into the antrum and/or duodenum as parallel volume occupying elements. Each member 110 is positioned at a different radial region of the pyloric canal. When the pyloric canal is open as in FIG. 5g, members 110 limit flow through the canal to a to region between members 110. When the pyloric sphincter is closed as in FIG. 5h, members 110 contact each other and an orifice is formed between members 110 thus maintaining the canal slightly open. In this embodiment, much of the grinding and rubbing in the pyloric region is transferred to the members 110 which rub against each other and not the pyloric tissue directly, thereby minimizing erosion of the tissue in the area.

In an embodiment related to that shown in FIGS. 5g-h, device 100 consists of up to 1,000 members 110 that are effectively like little spaghetti noodles 1-7 cm long that are tethered at one end of the pyloric muscle and at the other end at the distal antrum using anchors 108. Alternatively members 110 can be anchored at only one end, either the pyloric or antral and stretch or compress freely with the stomach contents and normal peristaltic motion. Movement of members 110 through stomach activity can activate mechanoreceptors present in the antrum/pyloric canal/duodenum leading to feedback control over eating. Members 110 can be made from a flexible material, such as, silicone, and be anchored at on end only in the submucosa or in the muscle layers with a single anchor 108 each or tether 116 and ball 118 as is described hereinbelow. Each member 110 can have a round, oval, square, rectangular, triangular or irregular cross section and also vary in width, shape and/or thickness along their length. Members 110 can be hollow and filled with a gas, liquid or a gel to increase their volumes and/or compliance along all or part of their length. The gaps between the members 110 may allow for chyme to pass through a closed pylorus and may also serve to partially block the pyloric aperture and fill the pseudodiverticulum volume when the pylorus is open. The advantage of multiple members 110 is that the force on each member 110 is relatively small and therefore the anchoring can be shallower, perhaps into the submucosa layer only, and hence simpler. Furthermore, should any anchor 108 fail, there will remain sufficient members 110 in the region to perform the function of device 100. Dislodged member 110 will pass harmlessly through the digestive system. Furthermore, device 10 including a plurality of members 110 will not be blocked by food particles because members 110 will be free to spread apart and rearrange themselves as the pylorus opens and closes and based on the prevailing axial flow of food through the pylorus. Assuming that each member 110 is 1 mm in diameter and that the maximum pyloric opening on average is 10 mm in diameter, then a quantity of approximately one hundred members 110 would fill the pyloric opening and effectively completely block it. In practice, one would only want to partially block the pyloric opening, so perhaps only 25 to 50 such members 110 would be needed to block the pylorus by 25% or 50% respectively. Anchor 108 can take the form of T anchor or a ball 118 which can be inserted via a punch across the submucosa layer, which is not connected rigidly to the stomach muscle layer. Anchor 108 can also take the form similar to the anchoring system of a tape worm which has miniature teeth at the head of the tape worm that bite into the submucosa at varying angles and prevent dislodgement. Such anchors could be preloaded and activated only once inside the stomach, allowing a subject to swallow a capsule containing members 110 that are then activated to anchor to the stomach lumen without further intervention. Anchor 108 can also be a rigid needle-shaped element that swells upon implantation and provides anchoring support. Anchor 108 can be forcibly projected or shot into the tissue, or sutured or clipped in place. Anchor 108 can take the form of a screw/helix made of a biocompatible or bioresorbale material, PLGA for example, which is screwed into the submucosa or underlying muscle layer. In the case of a bioresorbale material, the screw head of anchor 108 can dissolve and leave behind an elastic ball 118 which keeps element 110 permanently in place. Element 110 or tether 116 can have elastic consistency and therefore provide a seal around the hole in the submucosa layer and prevent acid or gastric juices from leaking into the underlying muscle layers. Implantation of device 100 in this embodiment can be effected endoscopically by pushing in all of the anchors 108 of members 110 simultaneously into the tissue proximal to the pylorus preassembled in a radial pattern around the pyloric opening or else served up in a "magazine" format inside the stomach and anchored one at a time. In the latter embodiment, once hundred members 110, each 2 cm long and 1 mm in diameter, can fit single file end-to-end into a hollow tube, say 1.2 mm inner diameter and 2 meters long that fits into the working channel of a standard gastroscope and are presented with the anchor side first to the tip of the working channel. Anchor 108 is secured into the tissue, the endoscope is then retracted 2 centimeters, member 110 is pulled out of the tube and remains tethered to stomach tissue by anchor 108, and the next member 110 is presented to the tip of the working channel of the endoscope and the cycle repeated until sufficient members 110 have been delivered into the pyloric region. Alternatively, member 110 can be a continuous rod of elastic material, for example silicone, that is introduced within the working channel or a gastroscope or alongside it in a separate tube and each member 110 has a portion of itself inserted and anchored into muscle tissue by a needle in the working channel of the gastroscope that works like a sewing machine, and that also cuts the continuous rod into smaller segments after inserting them, and then grasps the cut end to insert in the next location. The elastic force of the stomach tissue surrounding member 110 may be sufficient to anchor member 110 in the tissue without the need for anchors 108 or tethers 116 and balls 118. As a peristaltic wave flows through the tissue and the tissue tightens, it may also sufficiently compress and tightly grip member 110 to avoid member 110 from being pulled out of the tissue. Furthermore, member 110 can protrude just slightly outside the stomach lumen, in which case the omentum surrounding the serosal surface of the stomach will likely latch on to the end of member 110 external to the stomach and anchor it in place. Experiments done by the inventors have shown that the omentum acts to pull objects protruding through the stomach wall away from the stomach surface. Member 110 can have a protrusion or feature on it to prevent it from being pulled out of the stomach altogether by the omentum, thereby creating stable anchoring of member 110 or the entire device in general.

FIGS. 5i-j illustrate another alternative configuration of device 100 of the present invention. In this configuration, device body 102 is shaped as a pillar/column which is sized and configured for spanning a diameter of an open pyloric canal (1-2 cm) and is designed for flexible attachment at one or preferably two ends 114 through anchors or hooks 108 into the pylorus P tissue. Such a configuration is fabricated from relatively soft materials (shore A hardness 5 to 60) which can bend/buckle upon application of radial force or from hard material fabricated with a bending/buckling mechanism (e.g. hinge). In such a configuration, device body 102 bulks the pyloric canal when open (FIG. 5i) and bends/buckles to maintain the canal open when the pyloric sphincter is closed (FIG. 5j).

The design of FIG. 5i can be modified with a slit 116 which is closed when the canal is open (FIG. 5k) and open to create a conduit 106 (FIG. 5l) when the pyloric sphincter closes.

FIGS. 5m-n illustrate yet another embodiment of device 100 of the present invention. In this embodiment, device body 102 is shaped as a spiral spring-like element with attached hooks 108. Device body can be fabricated from any elastic material or material combination (e.g. NiTinol covered with silicon). Such a spiral configuration can be configured such that device body 102 moves and accommodates any movement of the tissue attached thereto. Thus, when the pyloric canal is open, device body 102 can be stretched across the pyloric canal distancing each spiral from the next, while when the pyloric sphincter is closed, the spirals can compact to form a hollow tube with conduit 106. Bulking would be provided by the thickness of the material forming the spiral (FIG. 5l), while conduits 106 are formed by features on the compacted spirals (FIG. 5m).

Figure 6A:
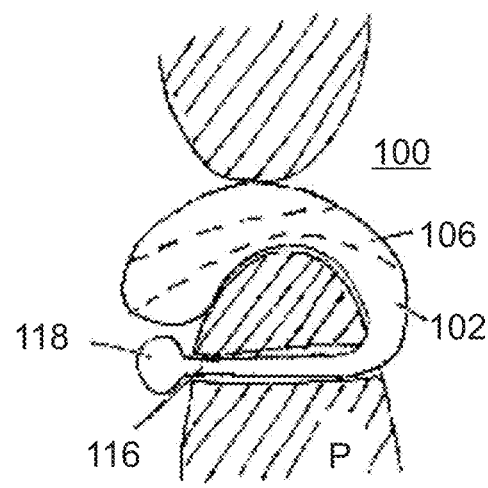

FIG. 6a depicts in a cross section of the narrowest portion of the pylorus device 100 which is made from a soft material, such as silicone rubber. In this embodiment, device 100 having body 102 and optionally conduit 106 is anchored to the tissue through a single elastic or inelastic tether 116 with an anchor (e.g. ball 118 shown in FIG. 6a) at the end. Based on the length, stiffness and shape of tether 116 and the size and shape of body 102, device 100 is designed to either stay in the duodenum, stay in the pyloric canal, stay in the antrum, or shuttle between any and all of these locations. Device 100 in this embodiment can be made from a single material, for example silicon rubber. Tether 116 is implanted through the stomach side of the pylorus P submucosa and/or muscle and ball 118 emerges at the duodenal side of the pyloric canal and keeps tether 116 from pulling out of the pyloric tissue and hence device 100 localized to the pyloric region. Tether 116 is preferable elastic and therefore stretches and contracts inside the pyloric muscle. Tether 116 can also be textured or be covered with a material that will increase adhesion to the pylorus P submucosa and/or muscle. Inside body 102, tether 116 and/or ball 118 can be a stiffer frame material, such as NiTinol, that increases the rigidity of all or part of device 100.

Figure 6B:
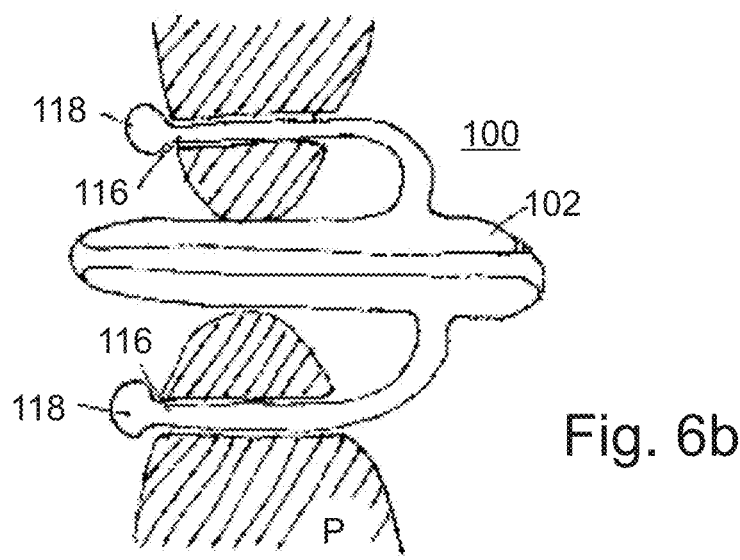

FIG. 6b depicts a further embodiment of device 100 in which body 102 is supported by two (or more) distinct tethers 116 with balls 118. Tethers 116 are flexible enough to not constrict the pylorus P muscle from fully opening, but act only to keep body 102 aligned in the pyloric region. Body 102 can be solid, have a through hole conduit or consist of invaginated conduits 106, as shown in a head-on perspective in FIG. 6c that allow for passage of food even when the pylorus is closed. Body 102 can vary in axial dimensions from the thickness of a membrane, approximately 1 mm thick, to a long tube approximately 5 cm long that extends from the distal antrum into the duodenum as shown in FIG. 6b, or any length in between. The second tether 116 can additionally or alternatively anchor device 100 to the distal antral region of the stomach.

Figure 6C:
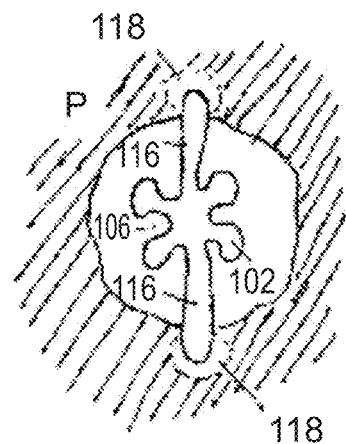
Figure 6D:
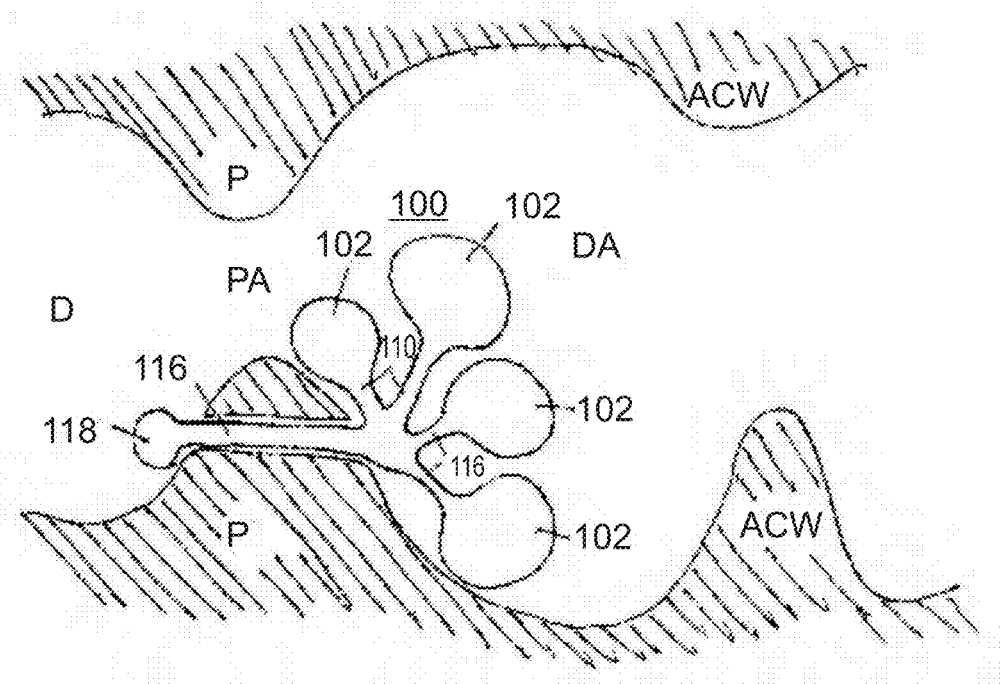
Figure 6E:
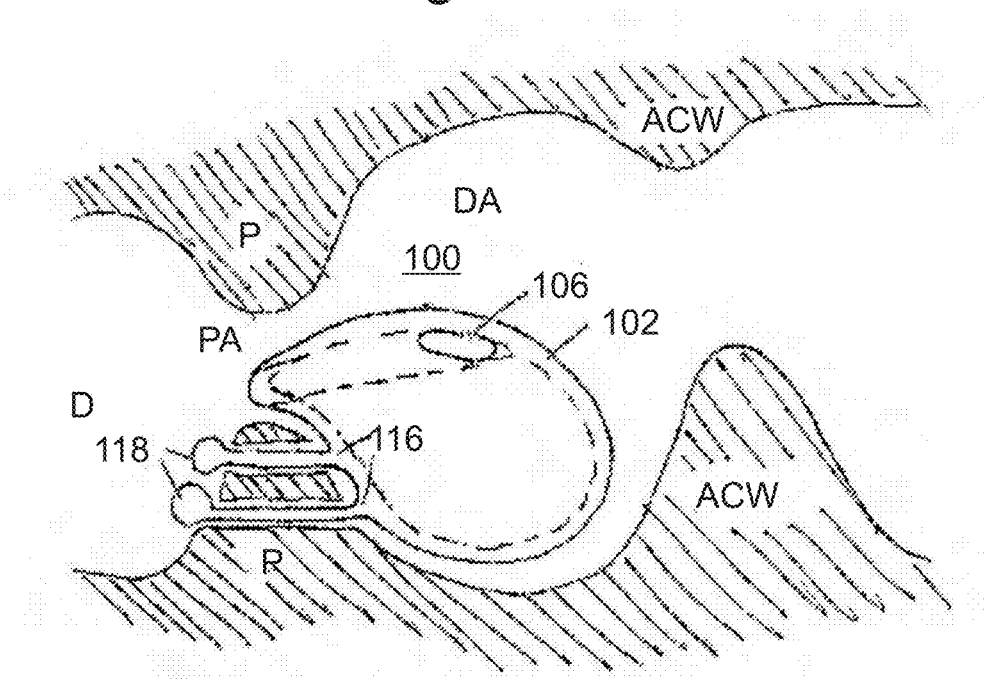
Figure 6F:
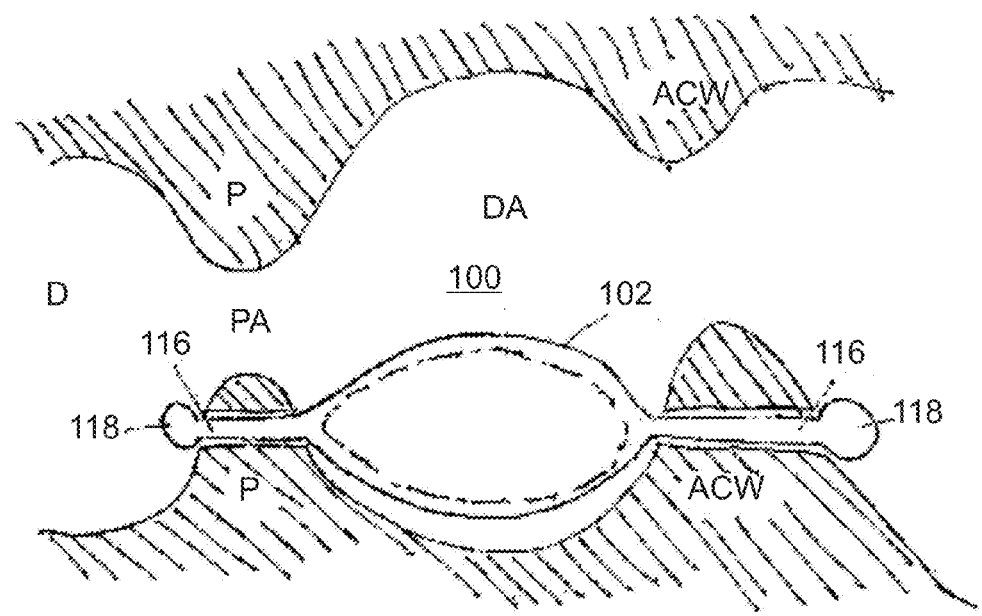

FIG. 6d depicts a further embodiment of the present invention where device 10 comprises multiple volume-occupying bodies 102 flexibly interconnected via tethers 116 and ball 118 to pylorus muscle P and resides in the distal antrum DA. Bodies 102 occupy space in the volume distal to the antral contraction waves (ACW) and partially obstruct the pyloric aperture (PA) or shuttle through the pyloric aperture into the proximal duodenum (D). FIG. 6e is yet another embodiment wherein body 102 is a space occupying entity that is anchored through two tethers into the pylorus muscle P, separated either radial or circumferentially, and resides in the distal antrum DA. Body 102, which ranges in size from 0.5 cm to 10 cm in diameter, preferably approximately 2 cm in diameter can be made of medical grade silicone, for example, and can be solid or hollow (hollow shown in FIG. 6e), in which case it can be filled with a gas, liquid, gel or a different solid used to provide body 102 with the proper flexibility to adjust to the complex and dynamic geometry of the GI tract in this vicinity. Body 102 can be sized to be approximately 2.5 cm or larger so as to not pass through the pyloric aperture (PA) in which case it will be intermittently pushed up against and effectively seal the aperture or pyloric canal in each attempt of the antrum to empty a bolus of chyme into the duodenum. Alternatively, body 102 can be small enough, approximately 1 cm diameter or smaller, to pass readily through an open pylorus and then "snap" back into the duodenum due to the force of elastic tether 116, thus being shuttled between the duodenum and antrum. Body 102 can optionally contain conduit 106 to allow chyme to pass through the closed pylorus as described elsewhere in this application. Tethers 116 and ball 118 can also be made of flexible material such as silicone so that the anchors keep body 102 in the proper position against the forces of normal peristaltic motion. FIG. 6f depicts a further embodiment wherein device 100 comprises a hollow volume-occupying body 102 which is anchored into the distal antrum in at least one location in order to resist migration through the distal antrum DA through the pyloric aperture PA. In FIG. 6f, two such axially distinct anchoring locations are shown. Body 102 is elastically/flexibly anchored to the pylorus muscle (P) and a section of the antrum, in this example the antral muscle (AN) through elastic tethers 116 and balls 118. Device 100 can consist of a plurality of such devices implanted in parallel that rub up against each other and against the canal when the pyloric canal is closed and then are separated when the canal is open. Body 102 can consist of a solid "tail" or hollow conduit 106 that extends distal through the pyloric aperture PA and may even extend into the duodenum to facilitate dumping as described elsewhere in this application.

Figure 6G:
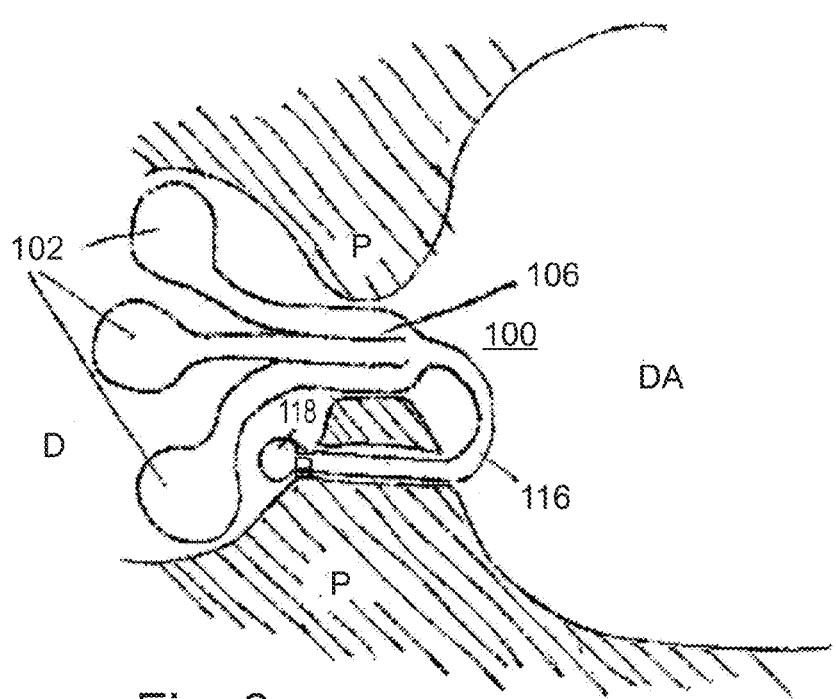

FIG. 6g depicts yet a further embodiment where device 100 is made of tubular body elements 102 that extend from the distal antral (DA) side of the pylorus (P) into the duodenum (D). Device 100 can be solid or alternatively have invaginated conduits 106 (similar in cross section to the device of FIG. 6c) to enable chyme to pass through a nominally closed pylorus. Device 100 is anchored using one or more flexible tethers 116 with or without an anchoring ball 118 to further anchor device 100. Tether 116 can be implanted endoscopically using the methods depicted elsewhere in this patent. Once device 100 is anchored into the pylorus muscle, body elements 102 are pushed through the pylorus individually using the endoscope or by normal peristaltic action. Once on the duodenal side of the pylorus, body elements 102 are too big to collectively pass back through the pylorus towards the antrum or alternatively they apply gentle pressure against the duodenal wall or the duodenal side of the pylorus and prevent device 100 from migrating back into the antrum, even in the case of duodenal reflux into the antrum. At the same time, tether 116 prevents device 100 from passing further into the duodenum against peristaltic motion and keeps device 100 in the pylorus region. Device 100 can therefore bulk the pyloric aperture thereby slowing down gastric emptying (based on the solid volume of device 100) and also prevent the pylorus from sealing properly therefore inducing dumping (based on the size and number of conduits 106). Device 100 in this embodiment can be removed by simply pulling it out with the aid of a grasping tool introduced through an endoscope. Device 100 of this embodiment can made of a single piece of flexible material, for example silicone rubber and be either solid or hollow. Device 100 can also be anchored in the distal antrum using through and through anchoring or an anchoring scheme totally internal to the GI system as described elsewhere in this patent.

In a further embodiment, an additional approach for anchoring device 100 is to utilize a magnetic clasp. For example, and referring to FIGS. 6a-g, tether 116 can terminate on the side distal to body 102 with an embedded or exposed magnetic element or metal plate. Body 102 also has on its distal side a magnetic element or to metal plate. When the two magnets or alternatively the magnet and metal plate are in proximity, tether 116 and body 102 latch together and stay adhered, thereby looping device 100 around the tissue. This latching can occur blindly without the need for exact alignment in the duodenum. Furthermore, the magnetic or metallic element in tether 116 can be sharpened and used as a self boring trocar that goes through the tissue when pushed from behind. Such a magnetic clasp can be instead of or in addition to ball 118 used for anchoring.

Alternatively, in a further embodiment, tether 116 can latch onto body 102 with a self-aligning latch, much like the tongue of a tie-wrap enters into a one-way latch mechanism. A jig can be used to align tether 116 to latch mechanism attached to body 102.

Alternatively in a further embodiment, tether 116 has a wire or other tension member running through it that when pulled from the antral side compresses a hollow ball 118 and flattens it, essentially increasing the cross-sectional area of ball 118 and preventing it from being pulled through the tissue.

Alternatively, in a further embodiment, tether 116 is introduced from the duodenal side using a back-facing needle and then pulled forward towards the antrum and connected to body 102 using any of the magnetic clasps or latching mechanisms described above or known in the art.

Since device 100 can maintain the pyloric canal partially open when the pyloric sphincter is closed, device 100 of the present invention can also include a valve mechanism to prevent backflow from the duodenum to the stomach. Such a valve mechanism can employ one or more soft flaps which are positioned within conduit 106 or incorporated into device body 102. Such a flap can be designed capable of resisting reflux (from the duodenum to the antrum) and yet substantially not obstruct flow from the antrum to the duodenum.

For the purpose of demonstrating the function of one embodiment of the anchored device of the present invention, a representative sequence of gastric emptying events as manifested in the antral/pyloric/duodenal regions is illustrated by FIGS. 2a-c described above. The function of device 10 with respect to these events is illustrated in FIGS. 2d-f.

The invaginated cross section of device 100 as show in FIG. 2e can act to make the pylorus "leaky" and force some of the undigested contents of the to pseudodiverticulum (PD) into the duodenum (D) prematurely (designated by the arrow in FIG. 2e) thereby reducing the lag time of satiety feedback signals and providing duodenal biochemical, neuronal and hormonal feedback signals that slow gastric emptying. Alternatively or additionally, the bulk of the flexible body of device 10 can project into the pseudodiverticulum PD as shown in FIGS. 2d and 2e (corresponding to the same stages of FIGS. 2a-b without device 100), thereby reducing the effective volume of chyme in the pseudodiverticulum. The bulk or volume of device 100 takes the place of chyme in the pseudodiverticulum PD and therefore causes less chyme to enter into the duodenum D, making each evacuation cycle less productive and hence slowing gastric emptying.

During this evacuation stage, the bulk of the cross section of device 100 positioned in a patent pylorus acts to partially block or restrict the flow of chyme through the pylorus and therefore slow gastric emptying. The body of device 100 is flexible enough, for example a soft silicone shell filled with a gas or saline, to conform to the narrow geometry of the pyloric canal PC. Device 100 can be anchored using any method described in this patent application to the pylorus (P) and/or distal antrum (A) to keep device 100 positioned in the pyloric canal (PC) without being forced into the duodenum D. When the cycle of FIGS. 2a-c repeats itself, device 10 reforms into its original shape shown in FIG. 2d and the cycle is repeated.

The device of the present invention can be effective at both the evacuation and retropropulsion phases of digestion. By controlling the geometry or cross section of a device, one can control the amount of dumping by, for example, increasing the extent of intentional mismatch between multiple devices, increasing the invagination of the device body cross section, or increasing the diameter of a hollow straw-like passageway of chyme through a closed pylorus). Likewise one can slow gastric emptying during evacuation by increasing the cross sectional area or bulk of the device to decrease flow or partially displace the volume of chyme in the pseudodiverticulum. The proper tradeoff for these two effects can provide the optimal effect in a patient. Furthermore, the device can be adjustable, say with inflatable chambers, so that the proper geometry will be set only after implantation and adjusted in real time for each patient.

As a further feature of the device, the blockage of the pylorus by the body of the device could block and better seal the pylorus thereby reduce the amount of bile to reflux resulting from bile acids flowing into the antrum through a patent pylorus. This device could help relieve ulcerative gastritis or change the chemical properties of the chyme in such a way as to cause malabsorption or trigger a duodenal feedback resulting from less well digested chyme entering the duodenum.

Device 100 of the present invention can also be configured capable of affecting stretch receptor function at the pylorus region thereby further facilitating early satiety.

Studies have shown that stretch receptors have an especially high density in the pylorus, and respond at lower levels of stretch than those of the antrum [Ramkumar and Schulze et al. Neurogastroenterol Motil (2005) 17 (Suppl. 1), 22-30]. Motor fibers of the vagus mediate stretch-mediated pyloric responses by releasing enkephalins and acetylcholine and inhibitory responses through the vasoactive intestinal peptide (VIP) and nitric oxide (NO). Thus, device body 102 can also effect stretch receptors present in pyloric canal tissue by physically opening and stretching the pylorus and the close by duodenal and antral tissues, which in turn can trigger the feedback mechanisms listed above to alter gastric emptying.

Device 100 can be inserted into the pylorus using a variety of techniques. Example 1 provides further description of one possible positioning and anchoring approach which can be used along with device 100 of the present invention.

As seen in FIG. 9, the general method of anchoring a soft tether described in Example 1 can be useful for anchoring other devices, including element 136, which can be a sensor, actuator, electrical mechanical or chemical stimulator, drug depot, or a magnetic/paramagnetic attachment point (as described more fully hereinunder), is attached to ball 118 on a tether 116 and is anchored inside muscle layer 140 between the serosa 138 and submucosal layer 142. The anchoring can also be through submucosa 142 without penetrating muscle layer 140 to allow the implanted device to move with submucosa 142. Alternatively, the anchoring can be through the serosa 138 as well. Such anchoring can be effected with a curved version of punch 132 and 134 as described in Example 1. Such anchoring can also be effected by the methods and devices described in FIGS. 21-25. Element 136 can be any device known in the art that is useful when positioned long term in the stomach.

The configuration shown in FIG. 9 can be used as a part of a system designed for retaining active agents in the GI tract. Such a system can include three components, an anchored retention element residing in the GI tract (as shown in to FIG. 9), a carrier that is taken orally and is designed for interacting with the anchored retention element, and an active agent contained in or formulated with the carrier. As an example of this embodiment, the device body can include a magnetic or paramagnetic retention element to which would automatically attach themselves magnetic or paramagnetic carriers that are introduced orally and that can be coated or filled with an active agent as above. In this embodiment, the device is anchored to the GI tissue of interest using any of the techniques described herein, at any point along the GI tract from the mouth to the anus where the release of an active agent is required. Following anchoring of the retention element, the subject swallows a carrier composed of magnetic or paramagnetic particle or particles, preferably any size from nanometers to a centimeter in size, which attach onto the device body due to magnetic forces. By way of example, the anchored retention element can be a sintered steel disc and the active compound coated onto micro or nano-particles of magnetic material that will fill the pores of the steel disc. The active agent contained in or around carrier would elute off into the GI system in a closed-loop or open-loop manner and over a time period longer than would be achievable if the active agent was swallowed without being attached to device body. The active agent is replenished by having the subject swallow another such carrier at a later time that would also attach itself to the device body.

The release of the active agent from the carrier could be controlled via open (no device feedback) or closed (device feedback) loop feedback mechanisms using a variety of sensors, actuators, extended release drug formulations, and passive and active drug depot technologies known in the art. Control of release can be effected from within the retention device, the carrier, or from a separate command issued from within or from outside the body by the subject, health care professional or any other sensor. For example, a satiety hormone could be released into the duodenum in a controlled manner any time stomach acid production is sensed. Alternatively, the packaging or polymer containing the active agent could degrade in a controlled fashion thereby releasing the active agent in the presence of acid so that no sensor would be required. Such a device, when anchored in the small intestine for example, can be used to release a drug (e.g. an immune modulator) for a disease (e.g. Crohn's disease) in an open loop continuous manner over a long period of time where such a drug might not easily survive the passage through the stomach (e.g. a peptide) and to when repeated administration is inconvenient or not practical. Another example would include diabetes therapy effected by insulin released into the small intestine using a controllable depot of insulin attached to the device body with the release triggered using an implanted or external glucose sensor or manually controlled by the subject.

The present invention envisions that any drug, regardless of the current form of delivery, can be formulated to reside in a carrier to be retained by an anchored retention device for extended or controlled release in a convenient and safe manner. In addition to magnetic or paramagnetic forces, other forces can be used to attach the active agent to the device body such as hydrophobic interactions, van der waals, electrostatic, colombic, antibody, biotin-avidin, covalent, crosslinking, size exclusion, affinity, electromagnetic or mechanical interactions (e.g. a form of Velcro™). The method of attachment can be reversible in a controlled or uncontrolled manner. For example, the active agent could be contained in a carrier capsule or particle that attaches to the device body for a set period of time and then detaches automatically (due to known off-rates of the attachment mechanism, the action of a timer or the acid degradation of a linker for example) or via remote control actuation, making room for the next carrier capsule introduced into the GI tract. Alternatively, new carrier particles can accumulate on top of old and depleted carrier particles as would be the case of magnetic forces. Once treatment ceases or once the binding sites on the device body are fully occupied, the carrier capsule, the entire device or just the device body can be removed from the GI tract using techniques described elsewhere in this patent application. Furthermore, instead of an active agent, the retained carrier can include a temporary biosensor or camera for example for measuring a parameter of the GI system for a period of time longer than would be permitted if the biosensor or camera would be subject to the normal peristaltic forces in the GI tract. Other devices, such as RFID, identifying tags, space occupying devices, stimulators with fixed battery life or flow reduction elements, can be attached to the anchored retention device using such a reversible linking scheme and replenished through a simple oral ingestion of a new carrier. It is also envisioned that such an active agent retention system can be utilized for other lumens in the body for similar effects, for example for long term release of an active agent, alteration of flow or measurement of parameters in the vascular system.

The present invention can be used for treating a variety of conditions and disorders which are associated with eating. As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Conditions and disorders associated with satiety include, but are not limited to, obesity and obesity related disorders such as for example anorexia and bulimia. Furthermore, use of the present device could precondition patients that are candidates for bariatric surgery as a simple way for weight reduction prior to surgery, and by providing an adjustment period for managing dumping syndrome symptoms.

Example individuals who may benefit from the present device for conditions other than eating disorders or obesity are described below.

Gastroparesis is abnormal functioning of the stomach without any physical evidence of obstruction, a debilitating condition which is mainly a complication of diabetes. Other etiologies include: (a) Parkinson and other neurological conditions (b) post vagotomy with pyloroplasty and other gastric surgeries (c) immune diseases such as lupus and scleroderma; and (d) gastric scaring due to past ulcers. Current treatments of these conditions vary from extensive life style and diet modification through pro kinetic medications and electrical stimulation. Keeping the pylorus open using the device illustrated in FIGS. 5a-c would serve to accelerate gastric emptying in these patients and significantly ameliorate the symptoms of the disorder.

Peptic ulcer disease (PUD) is an ulcer occurring near the pylorus that may cause strictures as a result of the inflammation. These patients after eradicating the cause of the ulcer may benefit from a device that keeps the otherwise narrowed pylorus open.

Post major abdominal surgical patients often complain of delayed gastric emptying symptoms. They may benefit from an open pyloric sphincter that keeps the flow of gastric secretions and food. In such patients, the need for the device may be temporary, and therefore the ability of removing the device or having it degrade and detach over time would be beneficial.

Hypertrophic pyloric stenosis (HPS) patients suffer from mechanical gastric outlet obstruction, and may benefit from a device capable of keeping the pylorus open.

To treat the above described disorders, the device of the present invention can to be implanted in the stomach of a subject using one of the approaches described herein. The device is implanted for a time period which is determined according to parameters assessed by the treating physician. Such parameters can include, the condition of the subject (e.g. severity of obesity), the eating habits of the subject, the intended purpose of the device (e.g. degree of weight loss desired) as well as other parameters. In any case, treatment is terminated by simply removing the device as described herein, or by enabling device self removal (e.g. using an anchor which is degradable over a predetermined time period).

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above description, illustrate the invention in a non limiting fashion.

Example 1

Anchoring of a Pylorus-Attached Device

Figure 7A:
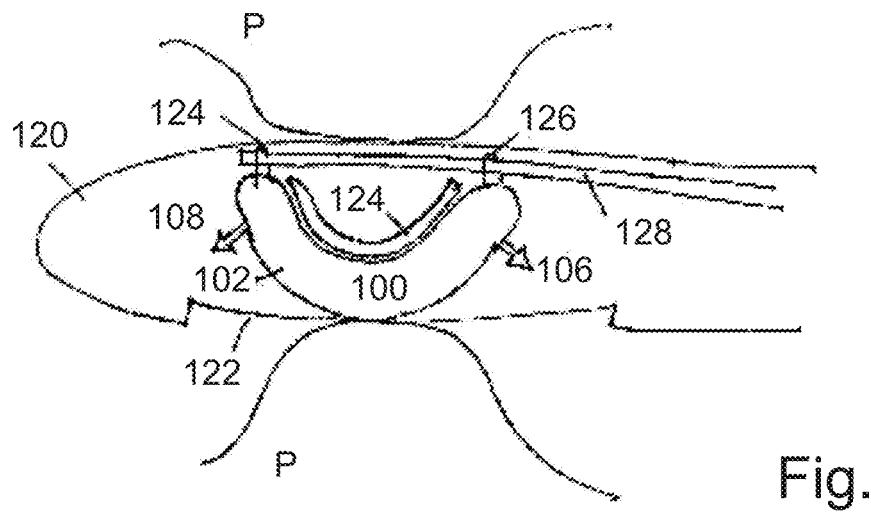
Figure 7B:
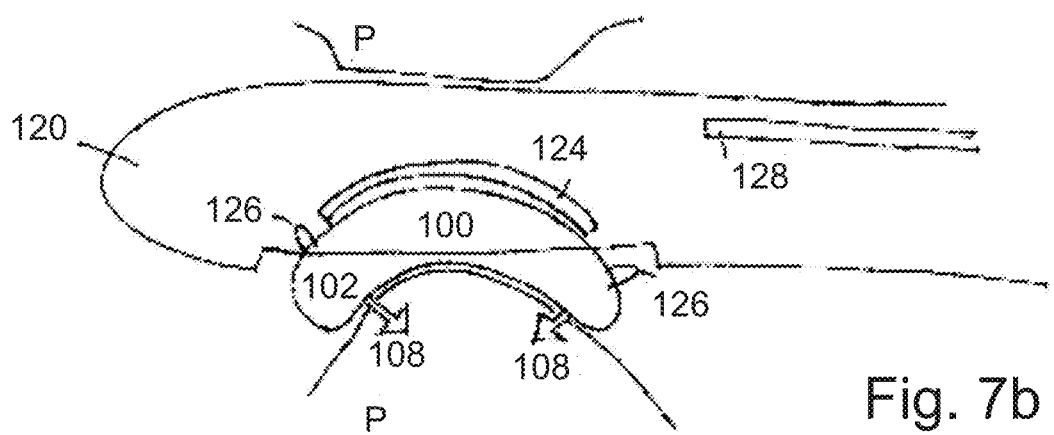
Figure 7C:
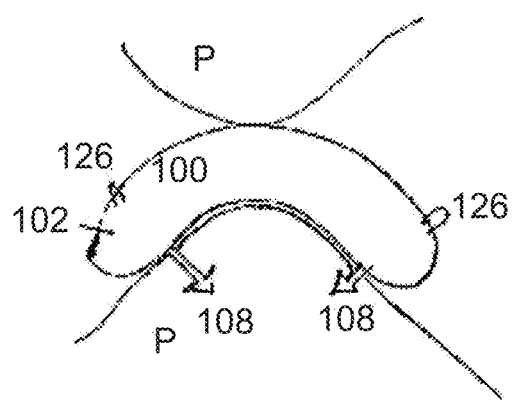

Device 100 can be inserted into the pylorus using a variety of techniques. For example, with reference to FIG. 7a, device 100 as depicted in FIG. 5b can be delivered at the end of an endoscope in a tube 120 with an open bottom 122 wherein the body 102 of device 100 is loaded against spring 124 that naturally concaves downwards but is held concave upwards by pin 128 running in a constrained channel through tube 120 and through retaining loops 126. Tube 120 (with anchors 108 retracted in tube 120 so that they cannot damage surrounding tissue) is positioned in the narrow apex of the pylorus P and pin 128 is pulled to release retaining loops 126 which in turn releases body 102 and spring 124 to the concave downward position, wherein anchors 108 are forced to bite into the pylorus tissue and anchor device 100 in the pylorus P (FIG. 7b). Tube 120 is retracted leaving device 10 anchored and positioned in the pylorus (FIG. 7c). The same technique can be used to anchor devices in other GI tissue areas, such as the lower esophageal sphincter.

In the case of the embodiment described in FIG. 6a-c, the insertion of a tether 116 can be effected via an endoscopic procedure by using the device shown in FIG. 8a-c. Tether 116 and ball 118 are supported by a two piece punch 132 and 134 made from a hard material such as steel. Punch 132 and 134 penetrate tissue layer M (FIG. 8a) all the way through the tissue, taking ball 118 and tether 116 along with them (FIG. 8b). Section 132 of the punch is then retracted followed by section 134 of the punch leaving tether 116 and ball 118 inserted into the tissue M (FIG. 8c). The process is repeated if more than one tether 116 is used.

Removal of device 100 can be effected using one of several approaches. Device 100 is removed (if needed) by simply pulling it out by detaching or overpowering ball 118, or any other anchor design used. Alternatively, ball 118 or tether 116 can be clipped via a clipping instrument mounted on an endoscope and the device removed via a grasper.

Example 2

Implantation of the Present Device in Pigs

Figure 10A:
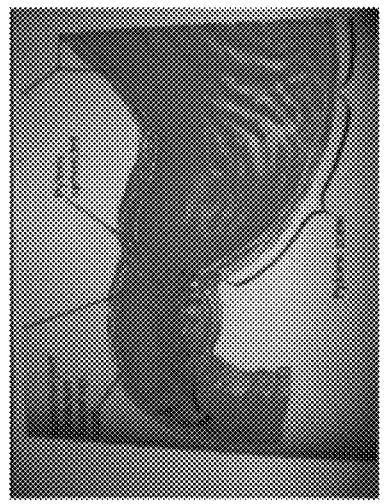
Figure 10B:
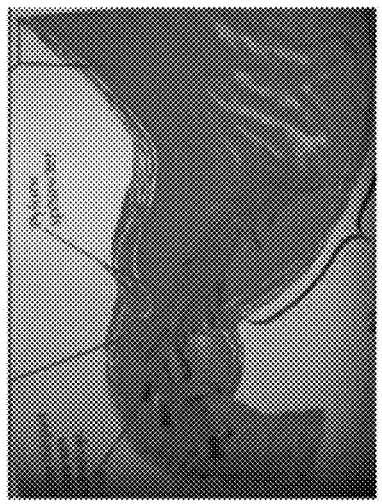
Figure 10C:
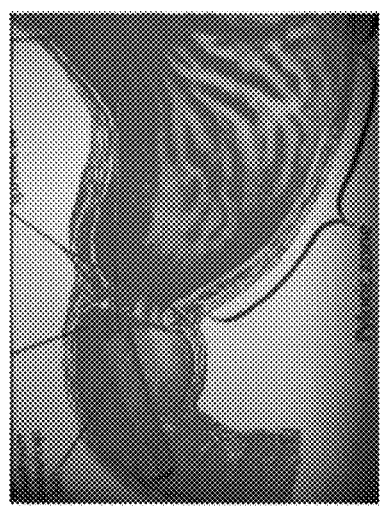
Figure 10D:
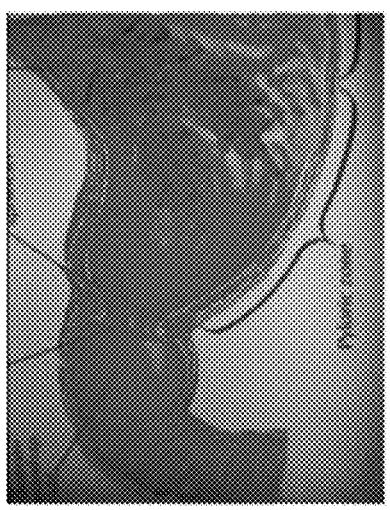

Four female pigs marked Shosh 7 to Shosh 10, approximately 3-4 months old weighing between 60-70 kilograms were selected for the implantation of 4 different configurations of the device of the present invention made of silicone. FIGS. 10a-d illustrate the four configurations of the present device as implanted in the four pigs. Each device shown in the figures was anchored to antrum tissue of a pig to achieve the anchoring positioning shown therein. Thus, FIG. 10a, depicts implantation in a first pig (designated as Shosh 7 in this study) of a 40 mm long 1 cm diameter cylindrical device body which was anchored in the antrum with an anchoring position and tether having a length enabling movement of the device body into the duodenum. FIG. 10b represents similar positioning in a second pig (designated as Shosh 8 in this study) of a device body which includes a plurality of brush-like projections with an anchoring to position and tether having a length enabling movement of the device body into the duodenum. FIG. 10c depicts antral positioning in a third pig (designated as Shosh 9 in this study) of two device bodies having brush-like projections with an anchoring position and tether having a length enabling movement of the device body in the antrum, while FIG. 10d illustrates antral-duodenal (trans-pyloric) positioning in a fourth pig (designated as Shosh 8 in this study) of a 100 mm long device body having brush-like projections with an anchoring position, device body and tether having a length enabling movement of the device body all the way from the antrum into the duodenum.

Prior to device implantation, each pig was anesthetized and a standard electrosurgical scalpel was used to make a 20 cm incision along the midline of abdomen to expose the stomach. The stomach was elevated to the surface of the skin and an incision was made on the side surface of the stomach midway between the lesser and greater curvature starting 3 cm proximal to the pylorus and extending for 5 cm along the antrum.

A curved taper-cut needle attached to a number 5 Ethibond™ braided polyester suture was inserted into the stomach cavity through this incision and passed into the antral tissue on the exposed opposite wall of the stomach through the muscosa, submucosa and partially through the muscle layer and re-emerging into the stomach cavity through a 1.5 cm tunnel. The end of the braided suture was tied to an elastic tether made of shore A 60 silicone 2 mm in diameter. The suture was used to pull the tether through the tissue tunnel. The suture needle was then inserted through a 1.5 cm diameter 2 mm thick "washer" made from shore A 60 silicone and the tether was pulled through this washer as well. The tether was attached on its other end to the device (whose geometry was described above). The device was located in the desired location in the antrum, duodenum or both, and the washer slid on the tether until it touched the antral tissue on the proximal end of the tissue tunnel. The elastic tether was then tied into 4 simple knots and the excess tether cut and removed. The stomach and abdomen were sutured closed with standard absorbable sutures using standard operative techniques. The external skin wound was closed with metal clips.

Results

The 4 pigs were provided with 4 days of recovery from the surgical intervention prior to entering a solid feed consumption trial. The pigs were provided commercial solid feed in the form of pellets (Ambar, Israel), identical to the feed provided to commercially grown pigs.

The feeding regime of the 4 pigs throughout the trial was as follows:
  (i) Pigs were fed twice a day, the first time at 06:00 and the second time at 14:00.
  (ii) In each feeding, every pig received 2 kg of feed, an amount which exceeds their feeding capacity in one session. Thus actual feed consumption is limited only by the appetite of the pig.
  (iii) Starting from time zero (providing the 2 kg feed to the pig), the feed quantity consumed was measured and recorded at 10 minutes, 20 minutes, 30 minutes, 45 minutes and 60 minutes.
  (iv) Starting from day zero, the weight of each of the 4 pigs participating in the trial was measured twice a week.
  (v) On day 21 of the trial, an endoscopic procedure was performed on each of the pigs, and the device was released from its anchoring site, and then endoscopically retrieved from the pig's stomach through their mouths.
  (vi) The same feeding protocol used during days 0-21 of the study, was used during days 22-33 of the study, when the devices were no longer present in the pigs' GI system
  (vii) On day 34, the 4 pigs were sacrificed and the study ended.

Observations of control female pigs (same genetic origin, same age and weight, with and without a sham operation) uncovered that the typical daily weight gain pattern of a commercially grown pig at a weight of 60 Kg. is 600-700 grams per day, while the typical daily weight gain pattern of a commercially grown pig at a weight of 90 Kg. is 900-1,100 grams per day.

Post implantation weight gain pattern of Pigs 1-4 (Shosh 7-Shosh 10) are graphically illustrated in FIG. 11 (with the device present in the GI tract of the pigs) and in FIG. 12 (following endoscopic removal of the device). During the period between days 0-21 with the devices implanted in their stomachs, the 4 pigs average daily weight gain was 460 grams per day, 24%-36% lower than untreated, commercially grown pigs in the same facility (see FIG. 11). During the period to between days 22-33 without the device in their stomachs, the 4 pigs average daily weight gain was 1,166 grams per day, 6%-29% higher than untreated commercially grown pigs in the same facility (see FIG. 12). Therefore the presence of the device in the GI tract of the pigs significantly slowed down their weight gain.

Example 3

Implantation of a Through-Stomach Antrum-Anchored Gastric Device in Live Pigs An eating behavior modification device with a silicone tether and a polypropylene T-anchor was anchored in an antral wall region of stomachs of female pigs using a dual-channel gastroscope. The delivery apparatus and attached device are shown in FIGS. 14-15. As is shown in FIG. 15, the device is secured to the applicator head of the delivery apparatus and the anchoring element of the device is secured within a groove formed in the delivery needle. The needle is disposed within working channel 1 of the gastroscope while the tether is secured against the applicator head by a snare-like element (retaining loop wire) which is disposed within working channel 2.

To deliver the device, the delivery apparatus and loaded device were guided through the mouth of an anesthetized pig through the esophagus and into the stomach.

Figure 18:
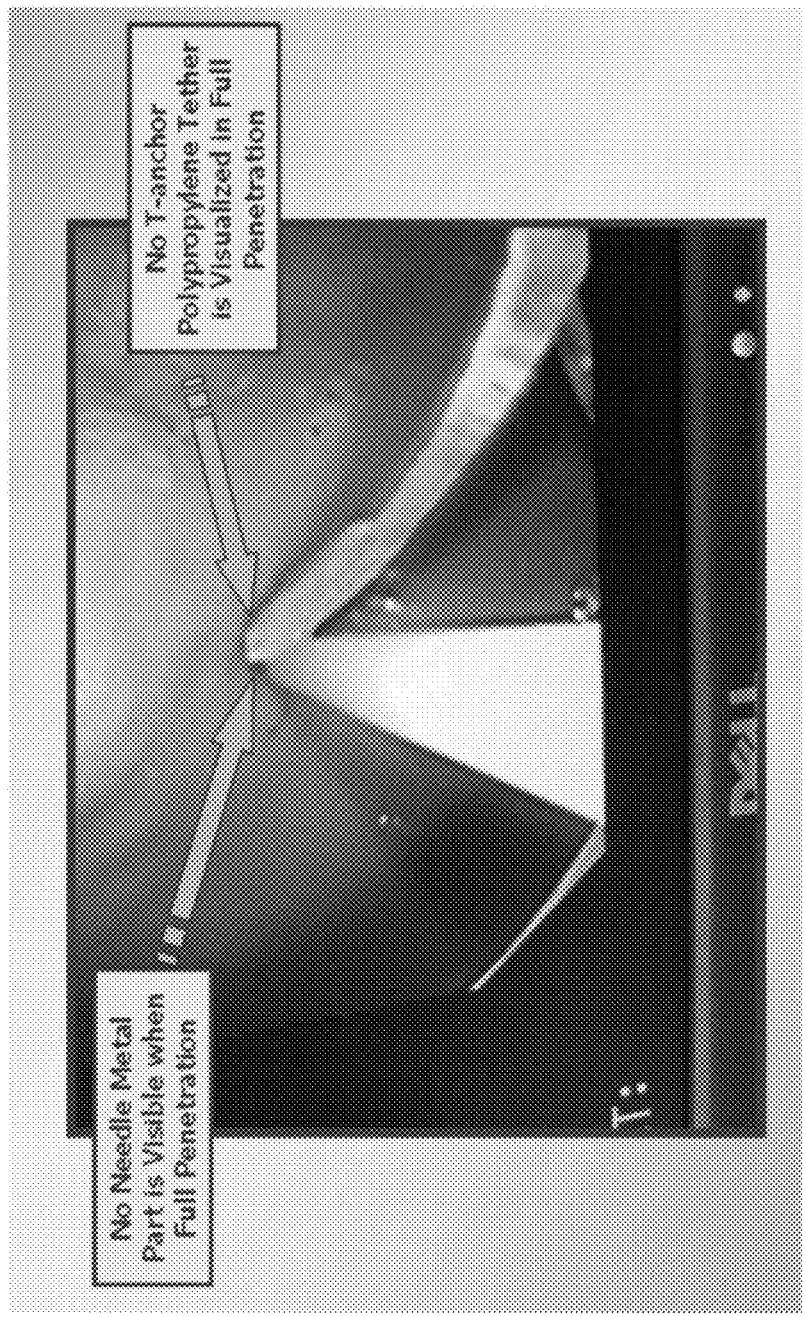

Once the applicator apparatus and loaded device are positioned within the stomach, the needle is pushed through the stomach wall (FIG. 16) under direct visual guidance and the anchoring element and tether of the anchor are advanced through the wall tissue and the anchoring element is deployed. In the configuration shown in FIG. 15, the 16 gauge hypodermic needle is 10 mm long and the anchoring element is a t-bar made out of a polypropylene cylinder 1 mm in diameter and 6 mm long. Deployment is effected via a plunger (push wire) disposed within the needle emerging at the operator end of the gastroscope. Once the needle and loaded t-bar anchor are pushed through the stomach wall (FIG. 17), the plunger is deployed to eject the t-bar anchor from the needle. Tension on the tether against the t-bar anchor aligns it against the tissue (serosa) and locks it into place (FIG. 18).

After the anchor is deployed, the needle is retracted back into the working channel, and the device is released in the stomach.

Figure 19A:
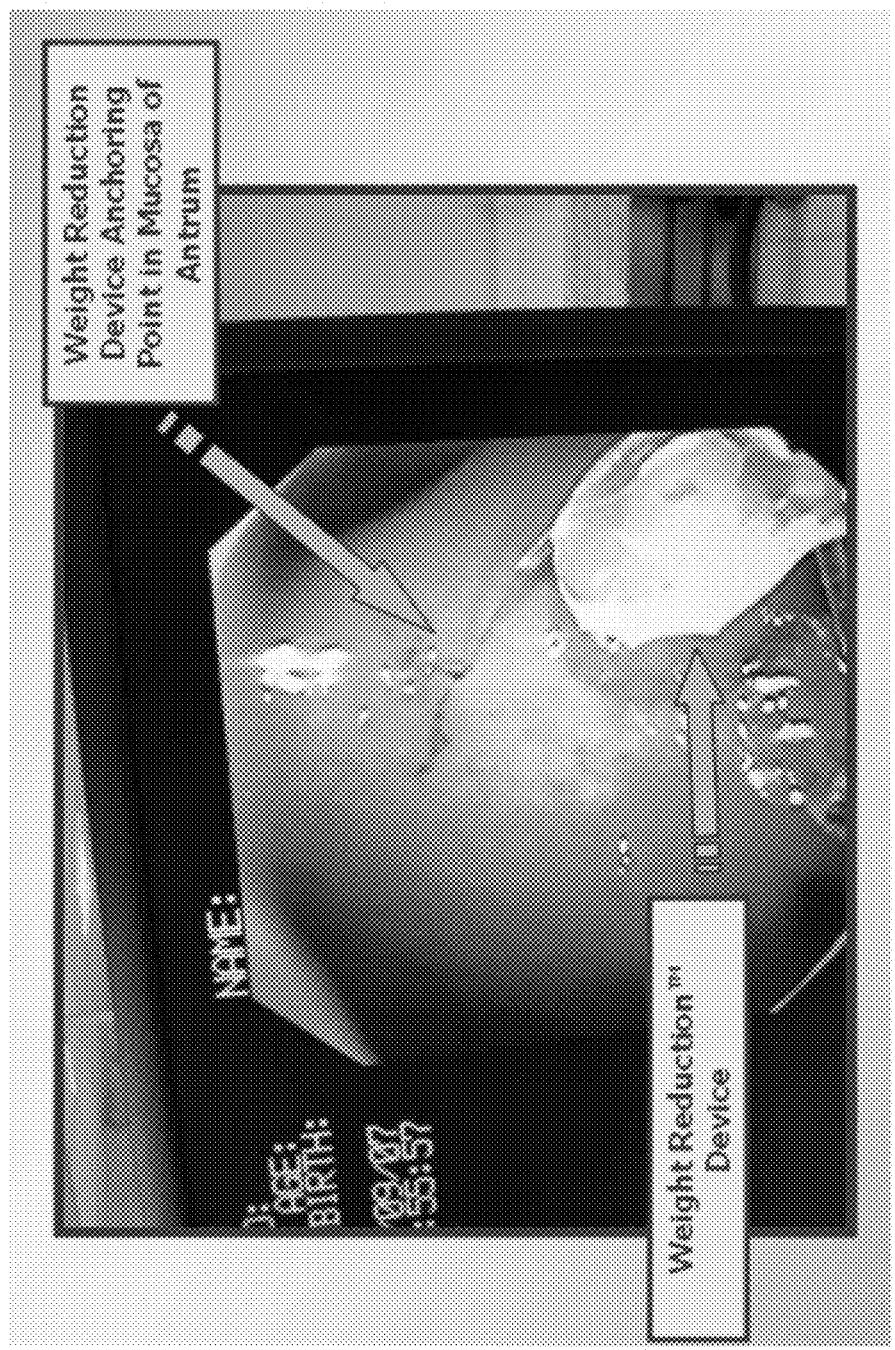
Figure 19B:

The above described procedure was successfully conducted on several pigs, in which the device was anchored to the stomach wall (FIG. 19a) for 16 weeks from to delivery to withdrawal. FIG. 19b shows three such devices anchored in the stomach of a single pig that resided with no complications in the stomach for 16 weeks.

The animals were sacrificed at the end of the 16 week period and tissue samples from the tissues around the anchoring sites were harvested, sectioned and mounted on slides.

FIG. 20a is a microscopic image of a mounted tissue section showing the region of anchoring (arrows); FIG. 20b illustrates regions of the tissue section shown in FIG. 20a which were further examined using higher magnification (FIGS. 20c-h). The histological features are typical of reaction to inert foreign matter. The degenerative changes observed in the mucosa and the tunica muscularis are mild and within the expected range for an area with low-grade inflammation. Thus, long term anchoring using the present anchor produces minimal tissue reaction and no adverse affects.

Example 4

Implantation of a Pyloric-Anchored Gastric Device in Live Pigs

The delivery apparatus described in FIG. 21a-c and FIG. 22a was used to anchor an eating behavior modification device of the present invention to the pyloric sphincter muscle of an anesthetized 40 kilo female pig. The delivery apparatus, designated 200 in FIGS. 21a-c, includes an endoscope 60 (only distal tip shown) having one or more working channels 62 and preferably a camera 72 and/or a camera which can curve back (~180°) out of a separate endoscope working channel. Apparatus 200 includes a delivery device 64 (needle in FIGS. 21a-c) which functions in carrying anchoring element 13 and delivering it through GI wall tissue or sphincter tissue. Delivery device 64 is deployed and operated through working channel 62.

Delivery device 64 can be constructed such that when sequestered within the working channel of an endoscope it does not substantially prevent bending of the working tip of an endoscope. This can be achieved by using a short needle (e.g. 10 mm) attached to a flexible pushrod or by fabricating the needle from an elastic alloy such as Nitinol.

Apparatus 200 further includes an optional alignment head 74 which is mountable on distal end of endoscope 60.

Alignment head 74 has several functions. First, it allows the operator of apparatus 200 to see the path that delivery device 64 will take when pushed out or working channel 62. Second, it prevents delivery device 64 from unwanted perforation of the lumen. Third, it provides a positioning aid and control over the depth and length of the insertion path for anchor 13 and tether 14 through tissue 82. In this way, device 10 can be positioned at a known distance from the narrowest portion of a sphincter opening for example. Fourth it provides a counter force to the pushing of delivery device 64 given the endoscope 60 may not be rigid enough to resist such a pushing force without moving and therefore losing the control and alignment of the insertion path of anchor 13 and tether 14 into tissue 82.

Alignment head 74 is preferably flat (e.g. 1-3 mm thick) and optionally transparent so as to not interfere with the operator's field of view as viewed through camera 72. Alignment head 74 is also flat in order to easily enter a sphincter and enable alignment head 74 to fit all the way against the annular ridge of a sphincter tissue without forcing the sphincter open. Delivery device 64 slides alongside alignment head 74 until it reaches needle stop 78. Alignment head 74 can have a distal arm 76 and optionally a proximal arm 80 used to position endoscope 60 around tissue 82 (in this case the ridge of a sphincter). Alignment head 74 can be positioned against tissue 82 passively using the twisting and axial positioning of endoscope 60 along with manipulation of the alignment wheels of endoscope 60 and/or through vacuum means or other tissue approximation means such as pullable helical or temporary anchors connected to alignment head between distal arm 76 and proximal arm 80. In some areas of the GI tract, there are natural convex tissue folds, such as along the angulus of the lesser curvature of the stomach, that can be used as a site of anchoring through the submucosa or through the muscle with the anchor and the device both being present in the GI tract using the techniques described herein. The distance between distal arm 76 and proximal arm 80 (or the distal tip of endoscope 60 in case no proximal arm 80 is used) determines the path length of delivery device 64 in tissue 82. Likewise, the length of distal arm 76 and proximal arm 80 determines the depth of insertion through the tissue of interest. A short depth (e.g. short arms of approximately 2-5 mm) would allow for sub-mucosal anchoring while a deep depth (e.g. long arms of approximately 5 mm or more) would allow for anchoring through muscle or even penetration outside the serosa. The importance of the proximal arm 80 is that the entry point of delivery device 64 into the tissue can be visualized by camera 72 until delivery device 64 either hits needle stop 78 or marker 84 on delivery device 64 is aligned with proximal arm 80 to (see FIG. 21*b*). Without proximal arm 80, tissue 82 can press up against camera 72 and the operator of apparatus 200 may not be able to visualize the insertion point of delivery device 64. All parts of alignment head 74 are atraumatic with rounded corners and optionally flexible side to side to prevent tissue damage while being manipulated in the GI lumen. Examples of suitable materials for alignment head 74 is molded plastic or silicone covered metal wire.

Device 10 (made up of anchoring element 13 tether 14 and device body 12) can be pulled along the outside of endoscope 60 from outside the body through the mouth and esophagus into the region of interest using a friction fit between anchor element 13 and the delivery device 64. Lubricant such as KY can be used to minimize friction of endoscope 60 and device 10 through the passageway to the implantation site. Apparatus 200 optionally includes an element 210 for securing device 10 to endoscope 60. Although device 10 can be introduced into the stomach separately from the introduction of endoscope 60, using endoscope 60 to carry device 10 into the stomach is preferred. Element 210 can be a snare or sheath which is deployable from working channel 62, an alternative working channel or actuator means running alongside endoscope 60. For example, a snare configuration can be realized by looping a wire out of channel 62. Such a loop can be pulled from the operator end of endoscope 60 through holes around the outside of a cup placed on the distal end of endoscope 60 (such cups are used for polyp snares and band ligation for example) and used to secure (ensnare) tether 14 or device 50 against the body of endoscope 60 or the distal cup attached thereto. Once anchoring element 13 of device 10 is delivered by delivery device 64, element 210 can be released to release device 10 from apparatus 200.

To deliver device 10, alignment head 74 of apparatus 200 is positioned around the ridge of tissue 82 as is illustrated in FIG. 21*a*. Delivery device 64 is pushed through tissue 82 until reaching needle stop 78 or until marker 84 was aligned with proximal arm 80 as viewed by camera 72 as in FIG. 21*b*. Anchor element 13 is pushed out of delivery device 64 using a flexible pushrod (not shown) running along the inside lumen of delivery device 64 and operated at the operator end of endoscope 60. Delivery device 64 is withdrawn back into working channel 62 of endoscope 60 and apparatus 200 is removed from the stomach leaving device 10 anchored in tissue 82 as in FIG. 21*c*.

The delivered device (10) functions in stimulating the antral and duodenal regions of the GI tract and is free to pass back and forth through the pyloric opening on an elastic tether that anchors the device within a few cm of the pyloric opening. The device body (12 in FIGS. 21*a-c*) is a molded cylinder with rounded ends made of silicone 10 mm in diameter and 25 mm long. The anchor and tether are made from one piece of silicone shore A 60 hardness. The tether is 1.5 mm in diameter and 4 cm long and the T anchor is 1 mm in diameter and 6 mm long with a Nitinol wire 4 mm long and 300 microns in diameter running through the center of the silicone T to stiffen it and to provide a radio-opaque marker of the anchor's position.

In the pig experiments described herein, delivery apparatus 200 employed a slotted 16 gauge 4 cm long hypodermic needle for delivering the device and an alignment head for guiding the trajectory of the needle through the tissue (FIG. 22*a*). The needle was delivered through a working channel of a standard endoscope (Olympus GIF 130) while the alignment head was mounted on the tip of the endoscope. The alignment head was positioned in the duodenum against the pylorus sphincter and the delivery needle was pushed through the pyloric sphincter to the distal end of the alignment head as per the technique described in FIGS. 21*a-c* (but without the proximal arm on the alignment head). The anchor was released and positioned on the duodenal side of the pyloric sphincter while the tether emerges on the antral side and connects to the device body. The anchored device is pictured in FIG. 22*b*. The procedure was repeated on a separate 40 kilo female pig with similar results.

Example 5

Anchoring Approaches

FIGS. 25*a-c* illustrates in-tissue anchoring of the present device via screw in coil anchors. Anchor element 13 in this case is a spring coil or soft tissue screw or auger made of metal or a polymer that is affixed to tether 14 and device body 12. Cup 88 protects the tissue from the sharp point of anchor element 13 and can also serve as a vacuum cup to help affix the tip of endoscope 60 to tissue 82 using vacuum means. FIG. 25*a* shows apparatus 200 approaching the anchoring position of tissue 82. FIG. 25*b* shows cup 88 in contact with tissue 82 and delivery device 64 having to screwed in anchor element 53 into tissue 82. FIG. 25*c* shows delivery device 64 detached from anchor element 53 and withdrawn back into working channel 62 of endoscope 60. Device 10 (which is comprised of anchor element 13, tether 14 and device body 12) is now anchored into tissue 82. Anchor element 13 can also be sized to fit completely within working channel 62 of endoscope 60, obviating the need for cup 88. Device 10 can be removed by cutting tether 14 or unscrewing anchor element 13 using the reverse of the endoscopic procedure as that described above. Anchor element 13 can be made out of PLA, PGA or the like and designed to biodegrade over time leaving only tether 14, with perhaps some protrusion or other anchoring feature, anchoring tether 14 and therefore device 10 in tissue 82.

FIGS. 23*a-c* illustrates a through-tissue anchoring of device 10 having a t-bar anchoring element 13. In the case depicted in these Figures, tissue anchoring is effected through a tissue fold created by a vacuum chamber 204. Device body 12 is not shown.

Apparatus 200 is designed for mounting on an endoscope (not shown) and includes a vacuum conduit 202 for communicating a vacuum force from a vacuum device positioned outside the body to vacuum chamber 204. Apparatus 200 further includes a movable tissue piercing element 206 (e.g. needle) which is designed for carrying tether 14 and anchoring element 13 through the tissue fold.

Apparatus 200 is used as follows. A device 10 is loaded onto apparatus 200 by placing anchoring element 13 within a groove in tissue piercing element 206, optionally coupling device body 12 to apparatus 200 or the endoscope onto which its mounted and running tether 14 along tissue piercing element 206 and body of apparatus 200. Device body 12 can be coupled to apparatus 200 or endoscope using an attachment mechanism which can be released by a cable running through a channel of the endoscope. Optionally, a soft (e.g. silicone) disc-shaped washer 208 is mounted within chamber 204 in the path of tissue piercing element 206. The washer serves to prevent tissue erosion or rip-through of the small t-bar anchoring element 13 into the submucosal due to the tension on tether 14.

FIG. 23a illustrates apparatus 200 with mounted device 10 as configured prior to advancement of apparatus 200 into a stomach of a subject. Once in the stomach, apparatus 200 and attached device 10 are maneuvered into position (e.g. wall of the antrum) using the endoscope mounted camera. Alternatively, apparatus 200 can be without visualization means and a separate imaging gastroscope (e.g. a "baby scope") inserted in parallel can used to image the position and function of apparatus 200. Vacuum chamber 204 is juxtaposed against the mucosa of the antrum and 650 mm Hg of vacuum is created therein using a 10 gage Teflon tube inserted through a second working channel of the gastroscope or parallel to a single channel gastroscope and connected to a vacuum pump. Vacuum chamber 204 can optionally contain multiple vacuum channels running along the top or sides of the chamber or multiple vacuum ports to allow for uniform distribution of vacuum along the entire length and breadth of the vacuum chamber. Such channels or multiple ports will not be sealed by the tissue upon it being sucked into the vacuum chamber and therefore allow for the suctioning of a uniform volume of tissue into the vacuum chamber. Alternatively, the top and sides of vacuum chamber can be formed from channels or tubes with a screen or porous mesh material to allow for uniform distribution of the vacuum force along the vacuum chamber volume without having any one point of vacuum entrance sealed by the tissue and therefore block the vacuum reaching other parts of vacuum chamber 204. A tissue fold 82 1-15 mm deep, preferably 5-10 mm, is pulled into vacuum chamber 204 under the negative pressure of the vacuum and tissue piercing element 206 is pushed by the operator to drive anchoring element 13 and attached tether through tissue fold 82 and through washer 208 to the distal end of vacuum chamber 204. Following tissue piercing, anchoring element is ejected from tissue piercing element 206 using an internal pushrod (not shown) and piercing element 206 is retracted back into the working channel of the endoscope. Vacuum in chamber 204 is released and apparatus 200 is removed from the stomach leaving behind device 10 anchored with anchor 13 through washer 208 in tissue fold 82 as shown in FIG. 23c. It is also envisioned that washer 208 can have the tether and device body attached to it and that both ends of tether 14 terminate with anchor element 13, thereby leading to a "forward anchoring" configuration.

Example 6

Implantation of an Antrum-Anchored Gastric Device in Live Pigs

Three female pigs approximately 2-3 months old weighing between 45-50 kilograms were selected for implantation of the device shown in FIGS. 23a-c. The pigs were anesthetized and apparatus 200 described above fitted on an Olympus GIF to 2T100 dual channel gastroscope which was used to implant device 10 in antrum tissue. The piercing element 206 was an 18 gauge needle 3.5 cm in length. Anchor element 13 was a t-anchor made of 21 gauge hypodermic tubing 6 mm in length attached to 25 mm of 00 Ethibond™ polyester braided suture which was run through a hole ground into the center of the t-anchor, run out one of the sides and then heat molded into a ball that would not fit back through the open end of the t-anchor tube. On its other end, the braided suture material was attached to a smaller t-anchor in a similar fashion which was in turn over-molded onto a silicone elastic tether 6cm in length 1.5 mm in diameter attached to a silicone torpedo-shaped device body 2.5 cm in length and 1 cm in diameter.

The devices were implanted using the implantation sequence described in FIGS. 23a-c and Example 5 above. The three pigs were provided with 4 days of recovery from the surgical intervention prior to entering a solid feed consumption trial. The pigs were provided commercial solid feed in the form of pellets (Ambar, Israel), identical to the feed provided commercially to pigs grown for meat production.

In all three pigs, no movement of the anchoring element or tissue erosion was detected, the devices remained in their original anchoring position showing that through tissue anchoring using a t-bar anchoring element and anti-erosion washer can be used to maintain a device within the stomach for extended time periods.

Example 7

Implantation of the Present Device in Pigs

Three female pigs (designated as 295 296 and 299), approximately 3 months old, each weighing between 42-46 kg were selected for the implantation of 2 different versions of the device of the present invention. Prior to device implantation, each pig was anesthetized.

Two anchoring configurations were deployed in this study, a bare stainless steel t-bar anchor without a washer (endoscopically implanted in pig 295), and a t-bar anchor with a washer (silicone disc) interposed between the t-bar anchor and the sub-mucosal layer of the stomach (implanted in pigs 296 and 299). The washer functions in reducing potential erosion and burrowing of the t-bar anchor through the mucosal, submucosal and muscle layers.

The t-bar anchors in both experiments were each attached to a Johnson and Johnson Ethibond™ braided polyester suture (00) which was attached to a 60 mm long silicone tether having a diameter of 1.5 mm The device body attached to the tether was a 25 mm long silicone torpedo-shaped cylinder 10 mm in diameter.

The devices were maintained in the stomach of the pigs for 2 weeks, following which, each of the 3 pigs was anesthetized, and a diagnostic endoscopy was performed. Following imaging, the pigs were sacrificed, and their stomachs were harvested for histological examination.

Results

During the 2 week study, there were no problems or adverse events associated with the 3 pigs in the study. FIG. 26 illustrates the anchor and attached device in Pig #295 (t-bar anchor without a washer). All three devices remained anchored and no signs of erosion or inflammation were evident at the site of implantation throughout the 2 week study.

Device anchoring was also examined in the harvested stomachs of the sacrificed animals. The devices anchored using both of the above described approaches remained in place with no sign of erosion or inflammation at the anchoring sites. FIG. 27 illustrates harvested stomach tissue with an attached device anchored via a t-bar anchor and a silicone washer (anchored in a live pig using the technique of Example 5 and FIGS. 23a-c). The sub-mucosal tissue around the anchoring site appears normal and free of any signs of erosion or inflammation.

The harvested stomach tissue was sectioned around the site of anchor implantation to reveal that anchoring depth ranged between 3.5-5 mm, demonstrating that the anchoring approach of the present invention enables in-muscle anchoring without perforation of the serosa (i.e. extrusion of the anchor through the wall of the stomach). If desired, a deeper cup can be used to suction a larger fold of the tissue in order to enable passing of the tether outside of the serosa and back into the stomach lumen.

It is appreciated that certain features of the invention, which are, for clarity, described in the context of separate embodiments, may also be provided in combination in a single embodiment. Conversely, various features of the invention, which are, for brevity, described in the context of a single embodiment, may also be to provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of altering eating behavior of a subject comprising:
    (a) providing a device body configured for partially blocking a pyloric aperture and sized for shuttling through a pylorus, said device body being attached to a tether having a length;
    (b) selecting a tissue position in the stomach for anchoring an end of said tether, said tissue position being selected such that said length of said tether enables at least a portion of said device body to shuttle between a duodenum and said stomach;
    (c) anchoring said end of said tether by penetrating tissue of said stomach at said tissue position.

2. The method of claim 1, wherein said tether is axially elastic.

3. The method of claim 1, wherein said penetrating is through a tissue fold of said stomach.

4. The method of claim 1, wherein (c) is effected by delivering a t-bar anchor attached to said tether into or through said tissue.

5. The method of claim 1, wherein said device body includes one or more discs.

6. The method of claim 1, wherein said shuttling is due to peristaltic forces in a gastrointestinal tract.

7. A method of altering eating behavior of a subject comprising:
    (a) providing a device body sized for shuttling through a pylorus, said device body being attachable to a tether having a length;
    (b) selecting a tissue position in the stomach for anchoring an end of said tether, said tissue position being selected such that said length of said tether enables said device body to shuttle between a duodenum and said stomach when attached to said tether;
    (c) anchoring said end of said tether by penetrating tissue of said stomach at said tissue position; and
    (d) attaching said device body to said tether.

8. The method of claim 7, wherein (c) and (d) are effected concomitantly.

9. A method of altering eating behavior of a subject comprising:
    (a) providing a device body configured for partially occluding a duodenum and being attached or attachable to a tether having a length;
    (b) selecting a tissue position in the stomach for anchoring an end of said tether, said tissue position being selected such that said length of said tether enables at least a portion of said device body to reside within said duodenum;
    (c) anchoring said end of said tether by penetrating tissue of said stomach at said tissue position.

10. The method of claim 9, wherein said device body includes a plurality of discs.

11. The method of claim 10, wherein at least one of said plurality of discs applies back pressure on the duodenal side of the pylorus.

12. The method of claim 9 wherein said device body is concomitantly or subsequently attached to said tether after step (c).

* * * * *